United States Patent [19]

Vitols et al.

[11] 4,047,154
[45] Sept. 6, 1977

[54] OPERATOR INTERACTIVE PATTERN PROCESSING SYSTEM

[75] Inventors: Visvaldis A. Vitols, Orange; John P. Riganati, Yorba Linda, both of Calif.

[73] Assignee: Rockwell International Corporation, El Segundo, Calif.

[21] Appl. No.: 722,306

[22] Filed: Sept. 10, 1976

[51] Int. Cl.² .............................................. G06K 9/00
[52] U.S. Cl. .................... 340/146.3 E; 340/146.3 ED
[58] Field of Search .............. 340/146.3 E, 146.3 ED, 340/172.5, 149 R

[56] References Cited

U.S. PATENT DOCUMENTS

| 3,271,738 | 9/1966 | Kamentsky | 340/146.3 ED |
|---|---|---|---|
| 3,292,149 | 12/1966 | Bourne | 340/146.3 E |
| 3,611,290 | 10/1971 | Luisi et al. | 340/146.3 E |
| 3,832,682 | 8/1974 | Brok et al. | 340/146.3 ED |
| 3,959,884 | 6/1976 | Jordan et al. | 340/146.3 E |

OTHER PUBLICATIONS

McMahon et al., "A Hybrid Optical Computer Processing Technique for Fingerprint ID.", *IEEE Tran. on Computers*, vol. C-24, No. 4, 4/1975, pp. 358-369.

*Primary Examiner*—Leo H. Boudreau
*Attorney, Agent, or Firm*—H. Fredrick Hamann; Harry John Staas

[57] ABSTRACT

An operator interactive pattern processing system is described which combines high speed recognition and processing abilities of an automatic portion with the estimating and recognition abilities of a human operator to extract correct data from patterns, such as poor quality unidentified latent fingerprint patterns and achieve rapid identification thereof. The automatic portion reads the unidentified pattern and extracts specific information therefrom such as ridge contour data describing the epidermal ridge flow and minutial data principally describing ridge endings and bifurcations. Topological data, identifying singularity points such as triradii and cores as well as ridge flow line tracings related to those points are automatically extracted from the ridge contour data. The extracted information is then utilized by the automatic portion to perform classification of the unknown fingerprint previously identified fingerprint patterns having the same classification type as they are selectively retrieved from a main file. The automatic portion contains circuitry for making value judgments as to its own functions at intermediate stages of its operation. The value judgment circuitry allows the automatic portion to communicate with an operator through an interactive controller whenever: it doubts the accuracy of its automatically identified singularity points; is unable to classify the unknown fingerprint pattern; obtains no matches to the unknown fingerprint; or obtains too many matches to the unknown fingerprint. At the request of the automatic portion, the operator then analyzes the specific data for which the automatic system determines it is having difficulty and either verifies or corrects the data stored in the automatic portion through the use of the interactive controller. The automatic portion then continues in its processing of the extracted data until identification of the unknown fingerprint is achieved.

35 Claims, 42 Drawing Figures

NO. OF PEAK ARRAY (32×32) AFTER MASKING

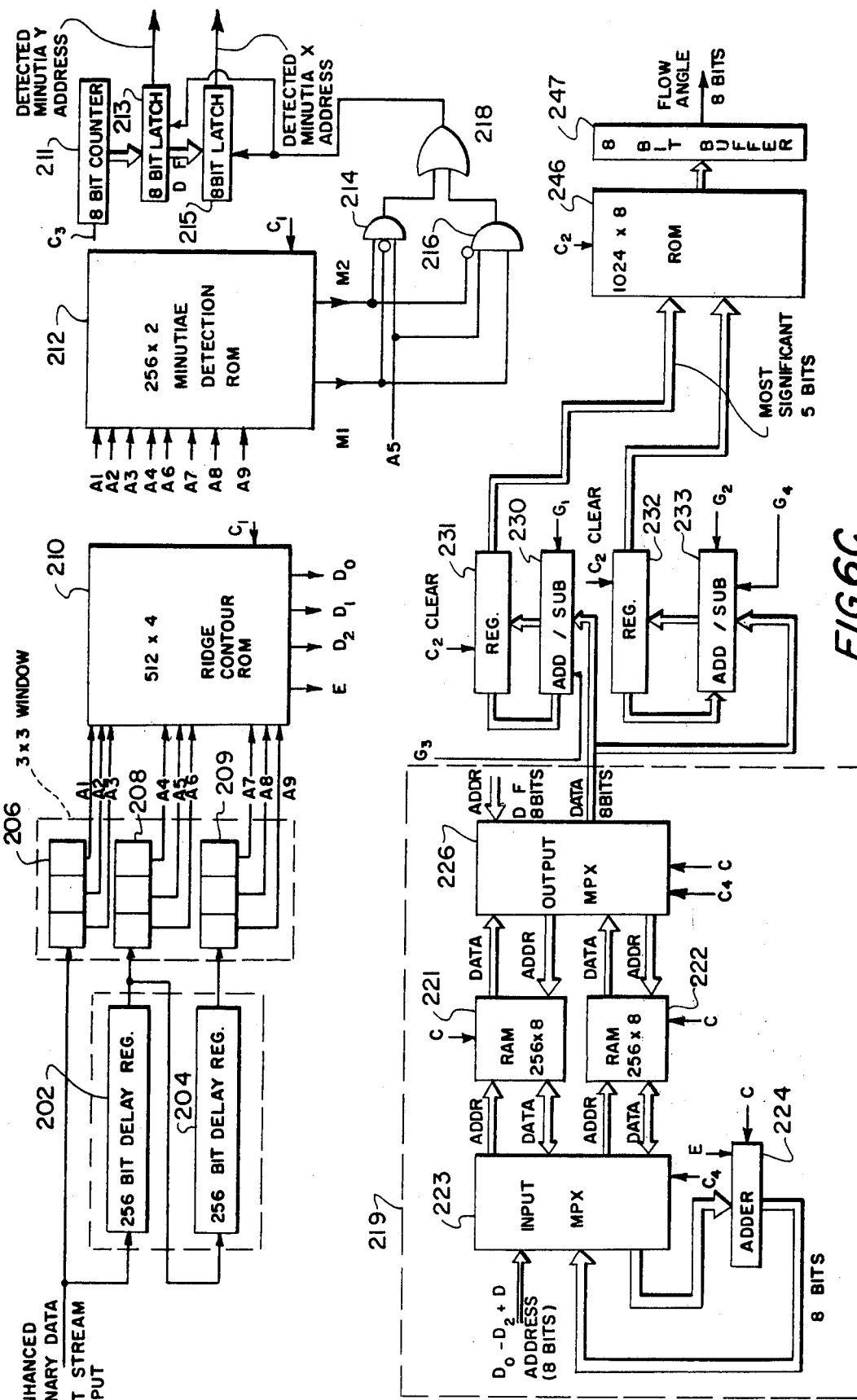

BIFURCATIONS

| Grid | Address $A_9 \ldots A_1$ |
|---|---|
| 1 0 1 / 0 1 0 / 0 0 1 | 001010101 |
| 0 0 1 / 0 1 0 / 1 0 1 | 101010001 |
| 1 0 0 / 0 1 0 / 1 0 1 | 101010100 |
| 1 0 1 / 0 1 0 / 1 0 0 | 100010101 |
| 1 0 1 / 0 1 0 / 0 1 0 | 010010101 |
| 0 0 1 / 1 1 0 / 0 0 1 | 001110001 |
| 0 1 0 / 0 1 0 / 1 0 1 | 101010010 |
| 1 0 0 / 0 1 1 / 1 0 0 | 100011100 |
| 1 0 0 / 0 1 1 / 0 1 0 | 010011100 |
| 0 0 1 / 1 1 0 / 0 1 0 | 010110001 |
| 0 1 0 / 1 1 0 / 0 0 1 | 001110010 |
| 0 1 0 / 0 1 1 / 1 0 0 | 100011010 |
| 0 1 0 / 1 1 1 / 0 0 0 | 000111010 |
| 0 0 0 / 1 1 1 / 0 1 0 | 010111000 |
| 0 1 0 / 0 1 1 / 0 1 0 | 010011010 |
| 0 1 0 / 1 1 0 / 0 1 0 | 010110010 |

RIDGE ENDINGS

| Grid | Address |
|---|---|
| 0 0 0 / 0 1 0 / 0 1 0 | 010010000 |
| 0 0 0 / 0 1 0 / 1 0 0 | 100010000 |
| 0 0 0 / 1 1 0 / 0 0 0 | 000110000 |
| 1 0 0 / 0 1 0 / 0 0 0 | 000010100 |
| 0 1 0 / 0 1 0 / 0 0 0 | 000010010 |
| 0 0 1 / 0 1 0 / 0 0 0 | 000010001 |
| 0 0 0 / 0 1 1 / 0 0 0 | 000011000 |
| 0 0 0 / 0 1 0 / 0 0 1 | 001010000 |

*FIG. 7*

| 3 × 3 WINDOW CONTENTS | | ADDRESS | YIELDS | ROM CONTENTS | | | |
|---|---|---|---|---|---|---|---|
| | | | | E | $D_2$ | $D_1$ | $D_0$ |
| | 010 / 010 / 010 | 010010010 | → | 1 | 0 | 0 | 0 |
| 010 / 010 / 100 | 001 / 010 / 010 | 010010001 / 100010010 | → → | 1 / 1 | 0 / 0 | 0 / 0 | 1 / 1 |
| | 001 / 010 / 100 | 100010001 | → | 1 | 0 | 1 | 0 |
| 001 / 110 / 000 | 000 / 011 / 100 | 100011000 / 000110001 | → → | 1 / 1 | 0 / 0 | 1 / 1 | 1 / 1 |
| | 000 / 111 / 000 | 000111000 | → | 1 | 1 | 0 | 0 |
| 100 / 011 / 000 | 000 / 110 / 001 | 001110000 / 000011100 | → → | 1 / 1 | 1 / 1 | 0 / 0 | 1 / 1 |
| | 100 / 010 / 001 | 001010100 | → | 1 | 1 | 1 | 0 |
| 010 / 010 / 001 | 100 / 010 / 010 | 010010100 / 001010010 | → → | 1 / 1 | 1 / 1 | 1 / 1 | 1 / 1 |
| | | ALL OTHERS | → | 0 | 0 | 0 | 0 |

FIG. 8

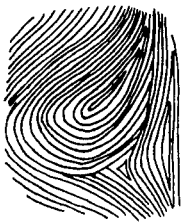
RIGHT LOOP
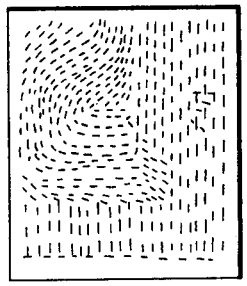
DERIVED RIDGE CONTOUR DATA
TRACING FOR CLASSIFICATION
*FIG. 9A*
WHORL
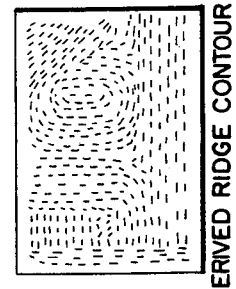
DERIVED RIDGE CONTOUR DATA
TRACING FOR CLASSIFICATION
*FIG. 9B*
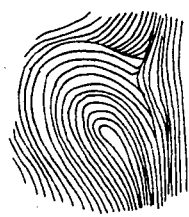
LEFT LOOP
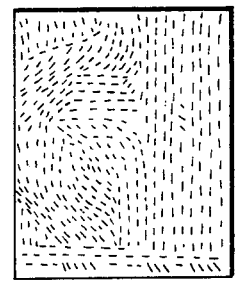
DERIVED RIDGE CONTOUR DATA
TRACING FOR CLASSIFICATION
*FIG. 9C*

RIDGE CONTOUR RAM
(38 × 38 BYTES)

7 × 7 BUFFER

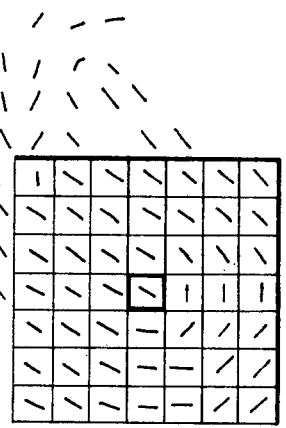
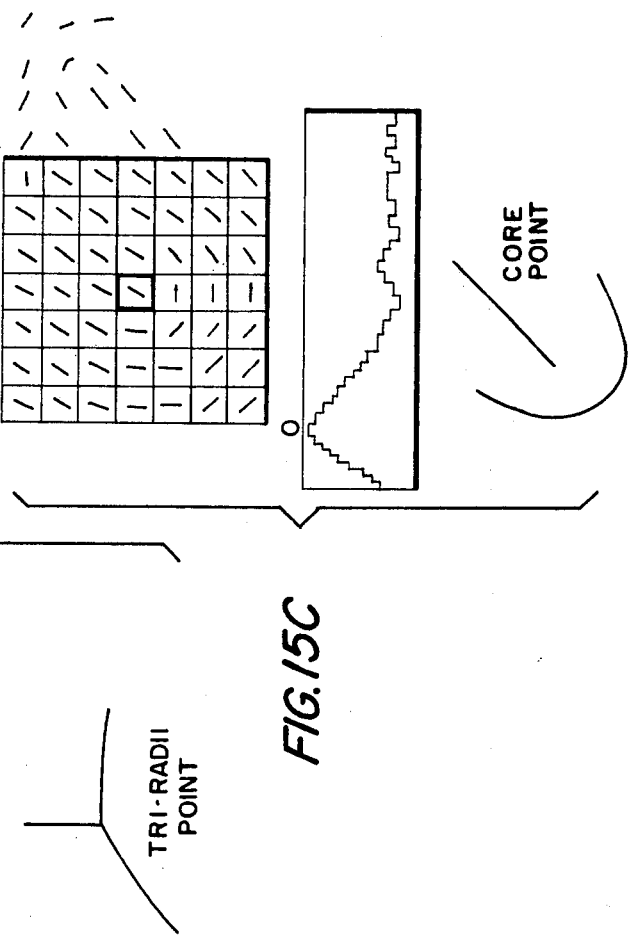
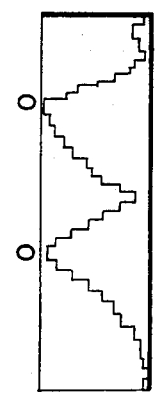
FIG. 15B
FIG. 15C
FIG. 15A

COUNT NO. OF PEAKS CIRCUIT 400

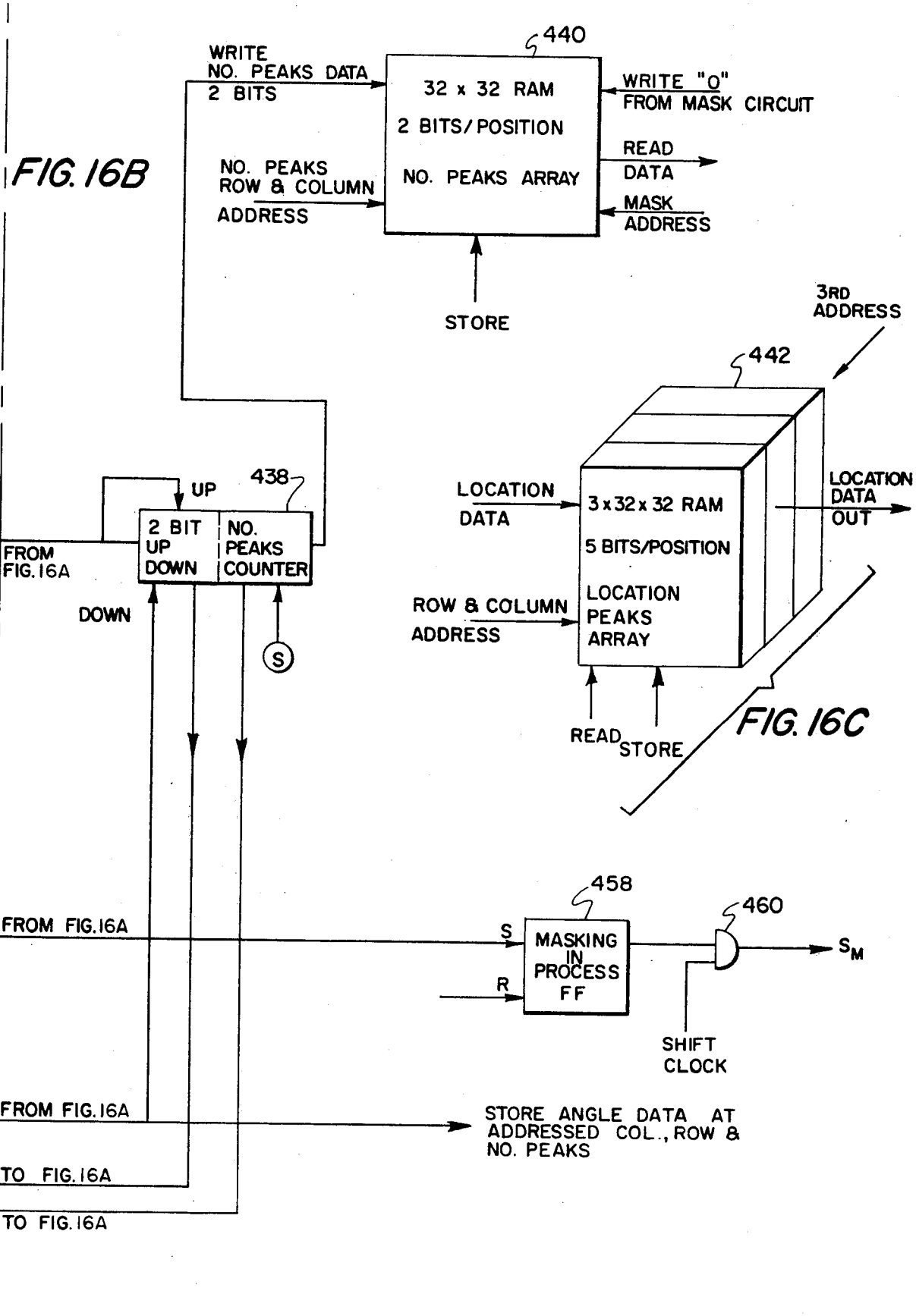

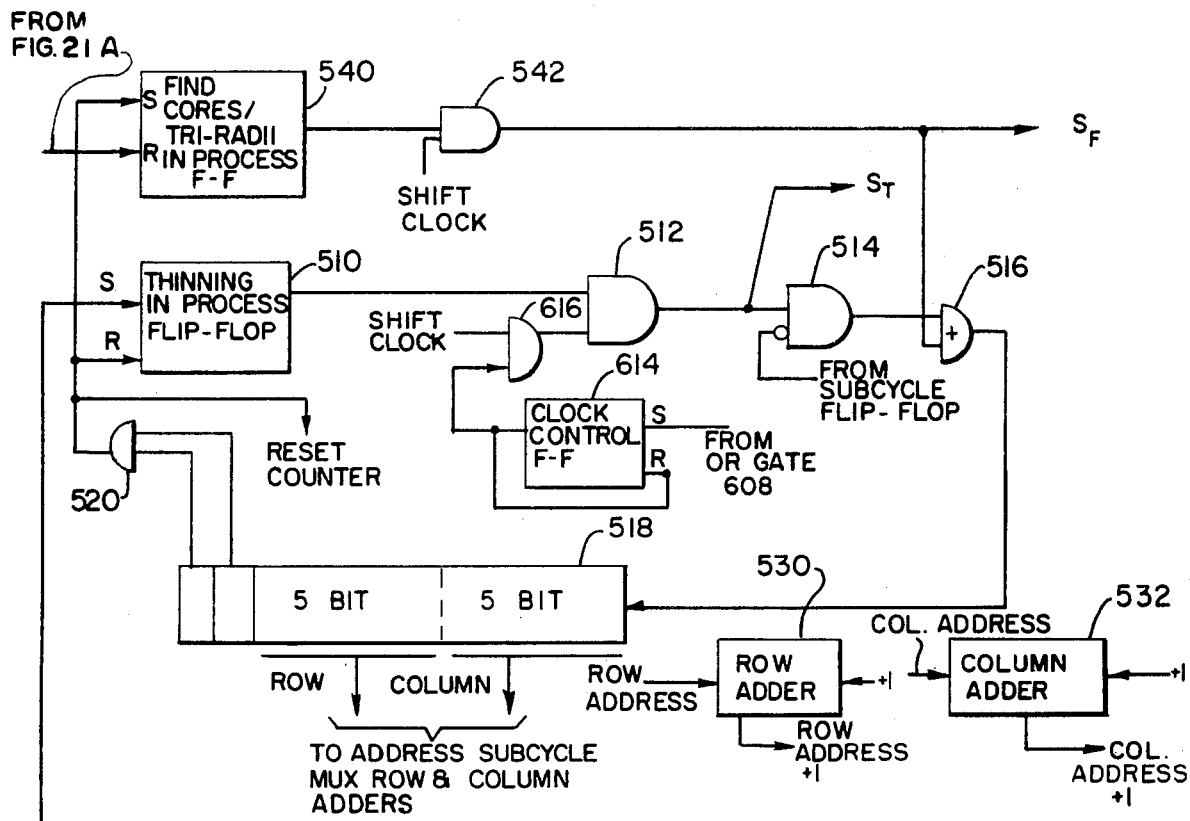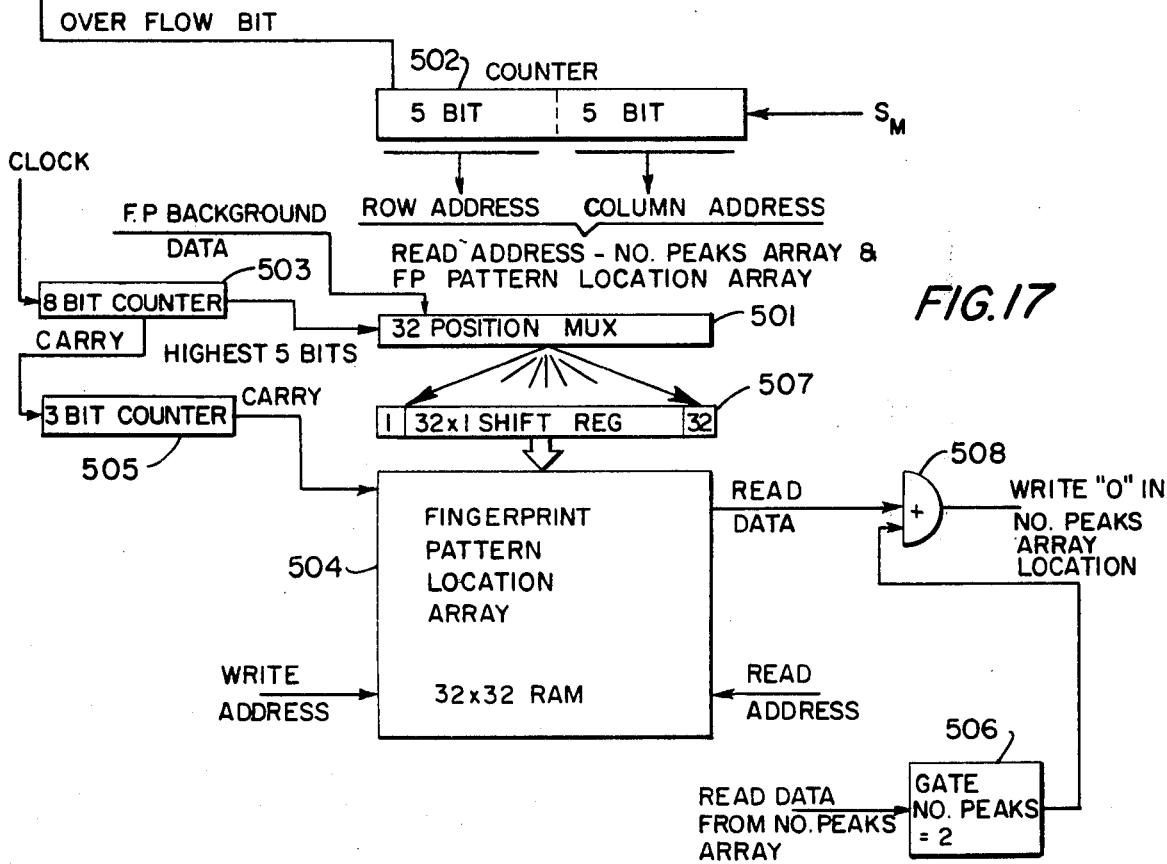
FIG. 17

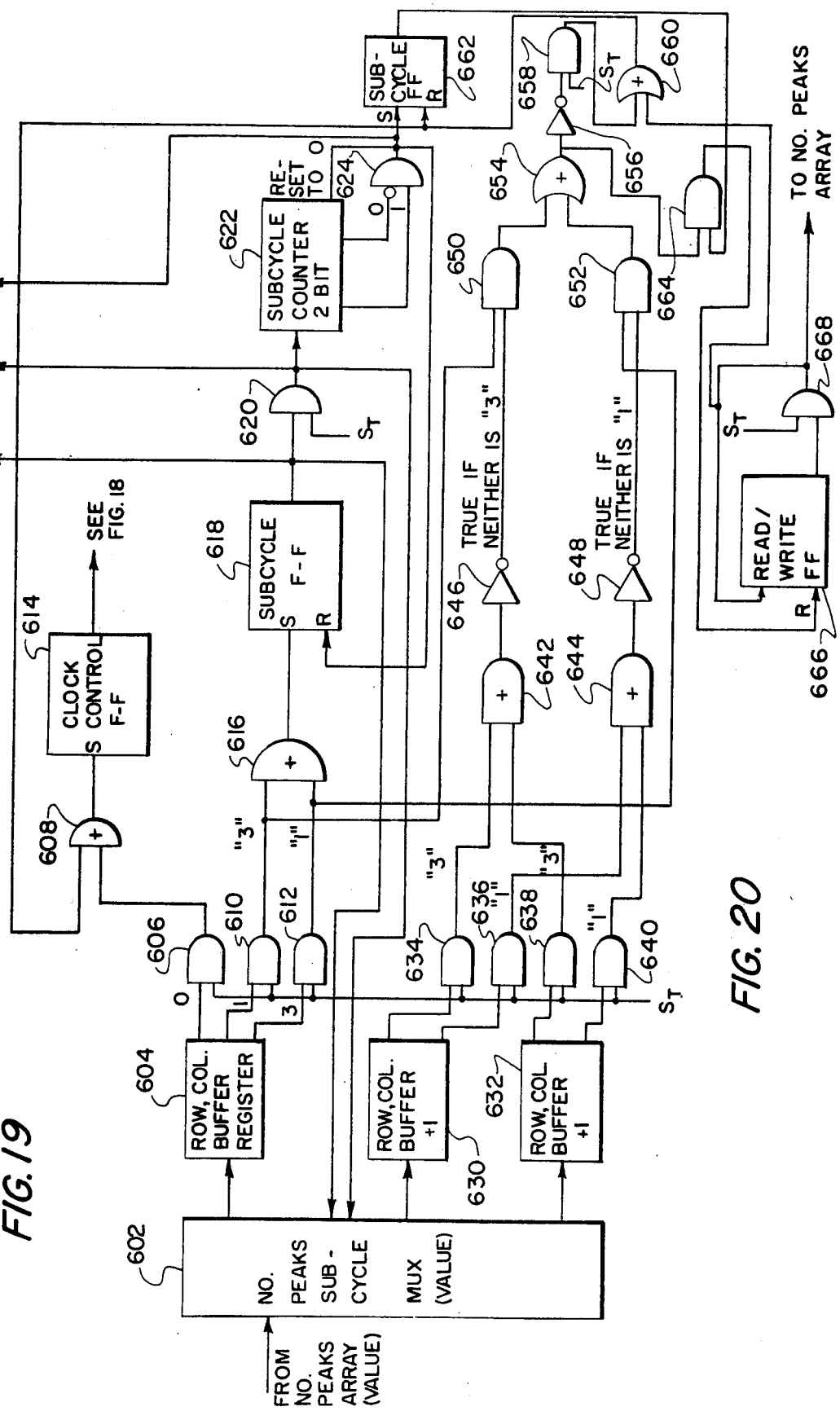

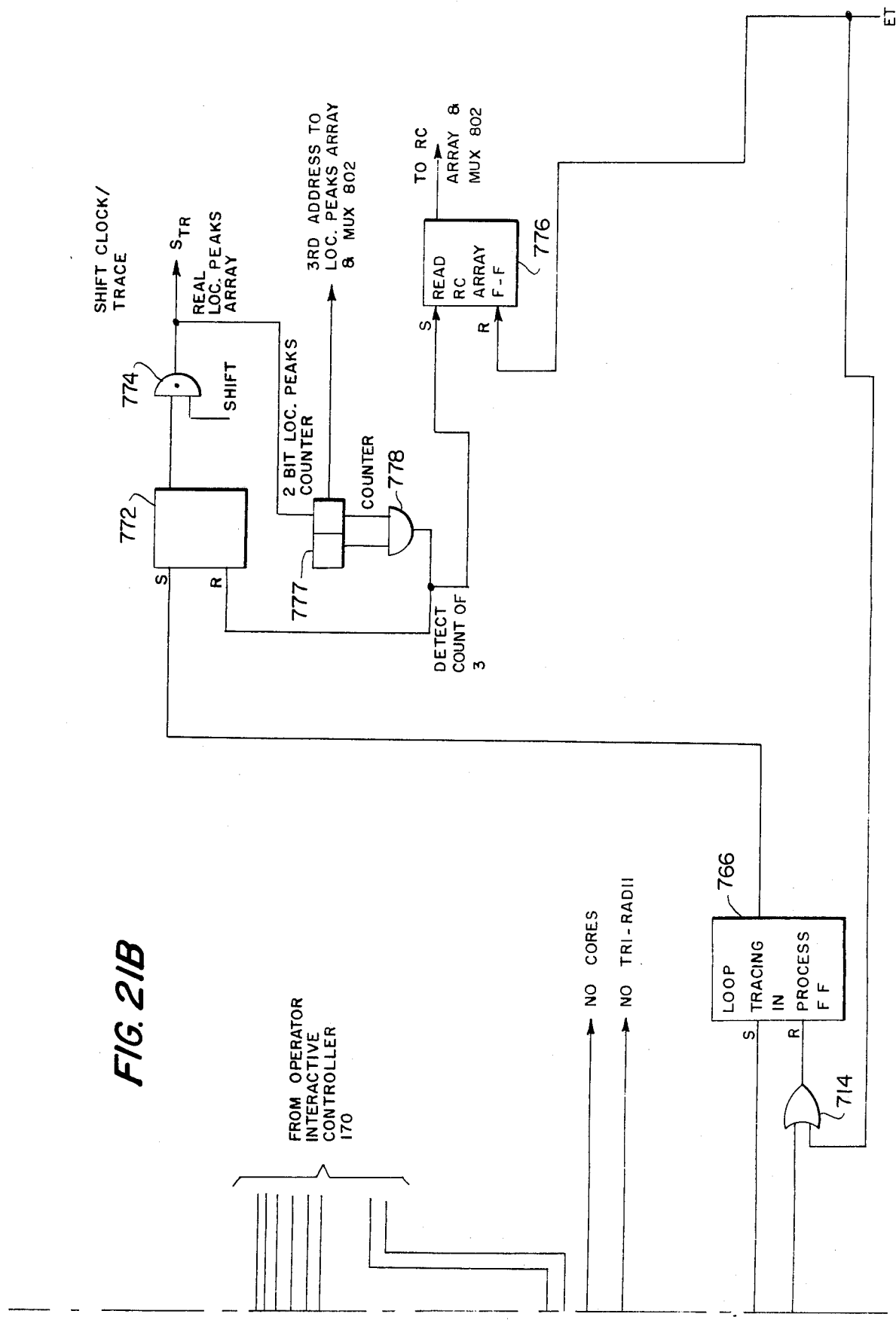

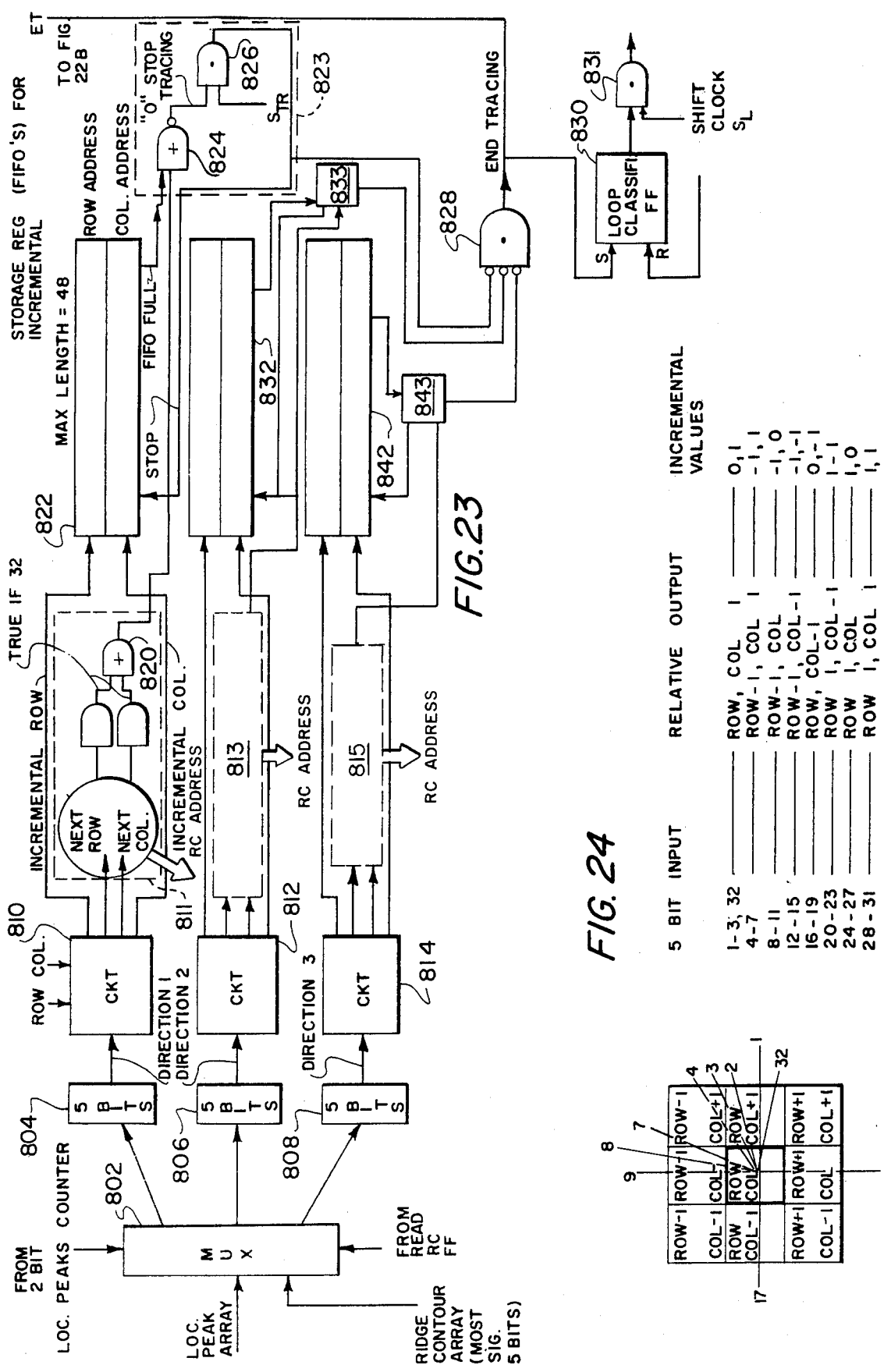

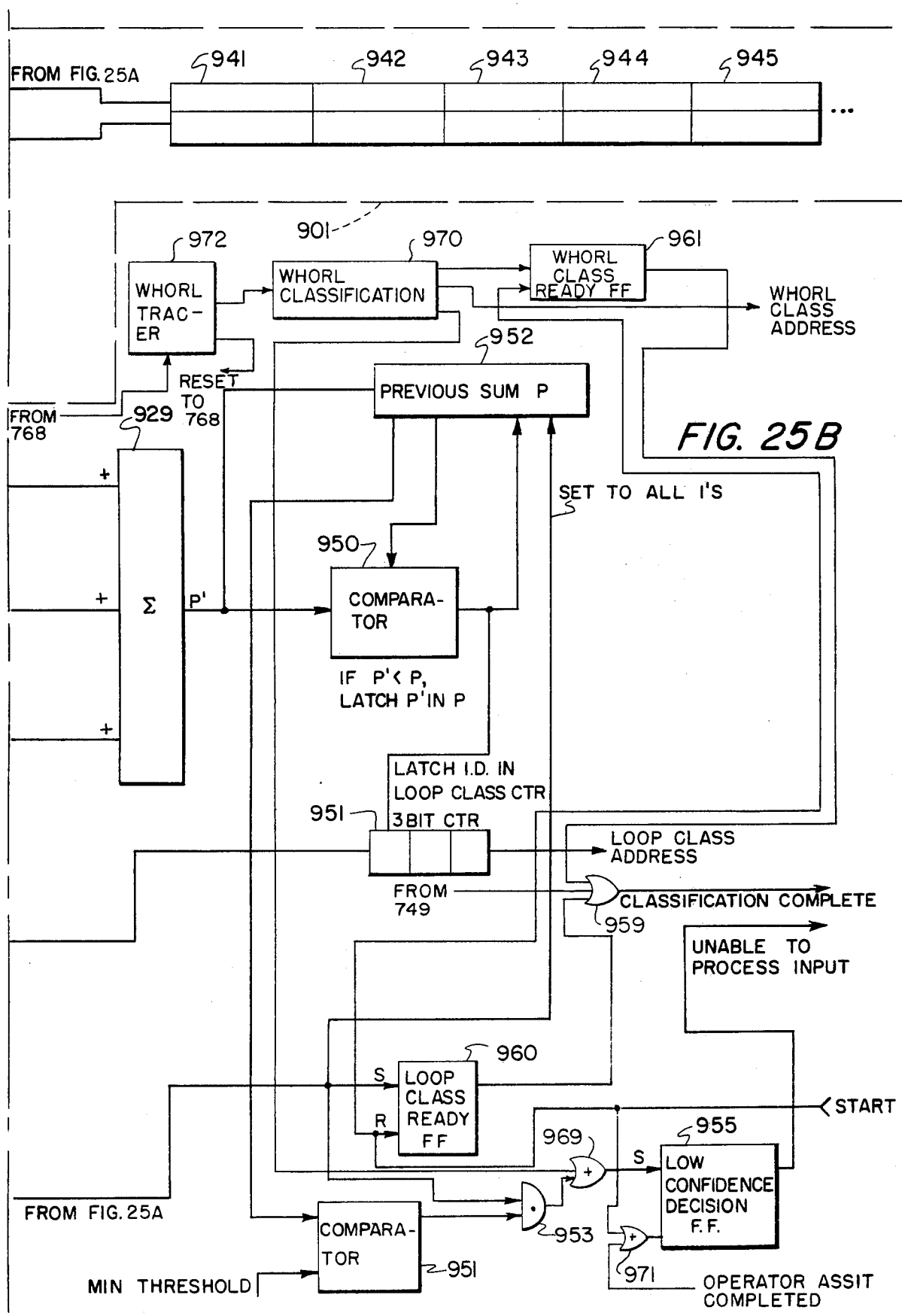

OPERATOR INTERACTIVE PATTERN PROCESSING SYSTEM

BACKGROUND OF THE INVENTION

1. Field of the Invention

The present invention relates to an operator interactive system for reading, processing and identifying patterns, such as fingerprints.

2. Description of the Prior Art

Law enforcement agencies have often in the past found it necessary to forgo the process of identifying latent fingerprints "lifted" from surfaces at the scene-of-a-crime due to the large amount of time and expense involved. Latent fingerprints are usually "lifted" from such inhospitable surfaces as bottles, window sills, door knobs, the inside of gloves, etc., and are often only fragmentary and, consequently, even more difficult to identify than good quality prints. Therefore, such latent fingerprints were often only useful when a suspect was apprehended due to other evidence and comparison of the latent prints were made with the fingerprints of that suspect. When it was decided that an identification process was to be performed on a latent print, a manual process was employed which often took many months to arrive at a probable identification.

In some prior art systems, it was necessary to visually analyze and tabulate data and estimate the proper orientation with respect to a predetermined reference orientation for all fingerprints. Then it was necessary to perform either a totally manual search or machine search and retrieval, followed by visual comparisons of the visually extracted and tabulated data with the stored fingerprint data to obtain an identification.

To the extent that machine systems are available, they are only useful for reading good quality fingerprints. In the past, if a latent fingerprint of poor quality or only a partial fingerprint was presented to a machine system, information would be extracted and processed. However, no indication was given that the system was extracting erroneous information. Only upon visual comparison with the retrieved fingerprint patterns could one determine that the system was retrieving the wrong fingerprints.

SUMMARY OF THE INVENTION

The present invention comprises a machine/operator interactive system which operates to extract specific information from fingerprint patterns such as those "lifted" from the scene-of-a-crime or rolled fingerprint impressions on fingerprint cards. The present invention is a modification of the automatic pattern processing system embodiment disclosed in our copending U.S. patent application Ser. No. 722,244, filed concurrently, entitled "Automatic Pattern Processing System" and incorporated herein by reference. Whereas the automatic pattern processing system is able to automatically read good quality prints, extract minutiae and contour data, and classify the fingerprint pattern prior to searching the main file to obtain a match and identification of the fingerprint pattern, an automatic portion of the interactive system of the present invention provides for operator interaction when the automatic portion makes value judgments during intermediate stages of its operation that operator assistance is required in the analysis of certain data. In the present invention, the automatic portion reads, extracts data from, classifies, searches and matches the latent fingerprint wherever possible. However, whenever the automatic portion determines that classification cannot be achieved, that classification is doubtful, that too many matches are produced, or that no matches are produced, the operator is then requested by the automatic portion to analyze the appropriate portion of the data stored in the system and determine if that data is correct. If a portion of that data is incorrect, the operator will then inform the automatic portion as to what the correct data should be according to the operator's observation and best estimate. The automatic portion will then proceed with its processing functions.

The present invention overcomes the problems of the prior art by providing a fingerprint identification system which combines some of the automatic processing functions, performed by a system such as that described in our earlier cited copending application, with circuitry for automatically making value judgments at intermediate stages of automatic processing functions and communicating those judgments to a human operator through appropriate interfacing hardware. By such a machine/operator interactive system, the speed and reliability at which low quality or partial (segmented) latent fingerprints can be processed and identified is increased greatly.

It is an object of the present invention to provide an operator interactive system for identifying fingerprint patterns, wherein the system automatically communicates with an operator when the automatic portion of the system doubts the correctness of its determinations during various intermediate stages of processing.

It is another object of the present invention to provide an operator interactive system for identifying latent fingerprints wherein partial or poor quality latent fingerprints may be processed without regard to their pattern orientation.

It is a further object of the present invention to provide an operator interactive system for identifying latent fingerprints wherein the automatic detection of too many singularity points in a pattern causes the system to automatically request that the operator determine which of the detected singularity points are most probably in error, and then, after receiving the operator's determination, to automatically process and identify the fingerprint.

It is still a further object of the present invention to provide an operator interactive system for identifying latent fingerprints wherein the automatic determination that a pattern is not classifiable causes the system to automatically communicate with an operator and receive the operator's determination of probable location of valid singularity points, probable associated curve tracings or probable classifications, and then proceed to automatically process and identify the fingerprint.

It is still a further object of the present invention to provide an operator interactive system for identifying latent fingerprints wherein, upon the automatic determination that no fingerprint patterns are found to match the latent fingerprint, the system automatically communicates with an operator and receives the operator's determination or probable location of valid singularity points, probable location and orientation of minutiae or correctness of location and orientation of automatically detected minutiae and then proceeds to automatically process and identify the latent fingerprint.

It is still a further object of the present invention to provide an interactive pattern identification system to extend the range for use for a fully automatic system by providing value judgment circuitry and machine/operator interface which allows the operator to supply or verify certain data when the automatic system is in doubt.

BRIEF DESCRIPTION OF THE DRAWINGS

The above and other objects, features and advantages of the invention, as well as the invention itself, will become more apparent to those silled in the art in the light of the following detailed description taken in consideration with the accompanying drawings wherein like reference numerals indicate like or corresponding parts throughout the several views and wherein:

FIGS. 6A-6F, hereinafter referred to as FIG. 6, illustrate a detailed block diagram of the binary image minutiae and ridge contour detector 110 shown in FIG. 2.

FIG. 7 illustrates examples of addresses corresponding to the detection of minutiae in a 3 × 3 window as shown in FIG. 6.

FIG. 8 illustrates various addresses corresponding to ridge flow directions detected in a 3 × 3 window, as is shown in FIG. 6.

FIG. 9A illustrates a fingerprint pattern of a right loop classification, a resultant storage of ridge contour data derived from the fingerprint pattern and the contour tracing produced from the ridge contour data. p FIG. 9B illustrates a fingerprint pattern, resultant ridge contour and contour tracing for a left loop classification.

FIG. 9C illustrates a fingerprint pattern, resultant ridge contour and contour tracing for a whorl classification.

FIGS. 15A, 15B and 15C, hereinafter referred to as FIG. 15, indicate examples of the ridge flow data in a 7 × 7 window for a non-singularity point, a tri-radii point, and a core point along with the correlation determination as a result of the calculation performed by the circuitry shown in FIG. 14.

FIGS. 16A, 16B and 16C, hereinafter referred to as FIG. 16, presents a detailed block diagram of the peak counting circuit of the classifier.

FIG. 17 is a detailed block diagram of a masking circuit operating on the information produced by the circuit shown in FIG. 16.

FIG. 19 illustrates three scanning cells used in the cluster thinning operation of the circuit shown in FIG. 20, during scans of the data in the No. of peaks array.

FIG. 20 is a detailed block diagram of a circuit for enhancing by thinning the clusters of peaks in the No. of peaks array as shown in FIG. 18.

FIGS. 21A, 21B and 21C, hereinafter referred to as FIG. 21, present a detailed block diagram of a circuit for locating and assigning X, Y addresses to detected core and tri-radii points enhanced by the thinning operation performed by the circuit shown in FIG. 20.

FIG. 23 is a detailed block diagram of a tracing circuit performing the tracing as illustrated in FIG. 22.

FIG. 24 illustrates the incremental values used in the circuit shown in FIG. 23 for producing the tracings of the flow lines as illustrated in FIG. 22.

FIGS. 25A and 25B, hereinafter referred to as FIG. 25, present a detailed block diagram of a comparison circuit which assigns a classification to the incremental values produced as a result of the curve tracing performed by the circuitry shown in FIG. 23.

DETAILED DESCRIPTION OF THE PREFERRED EMBODIMENT

Figure 1:
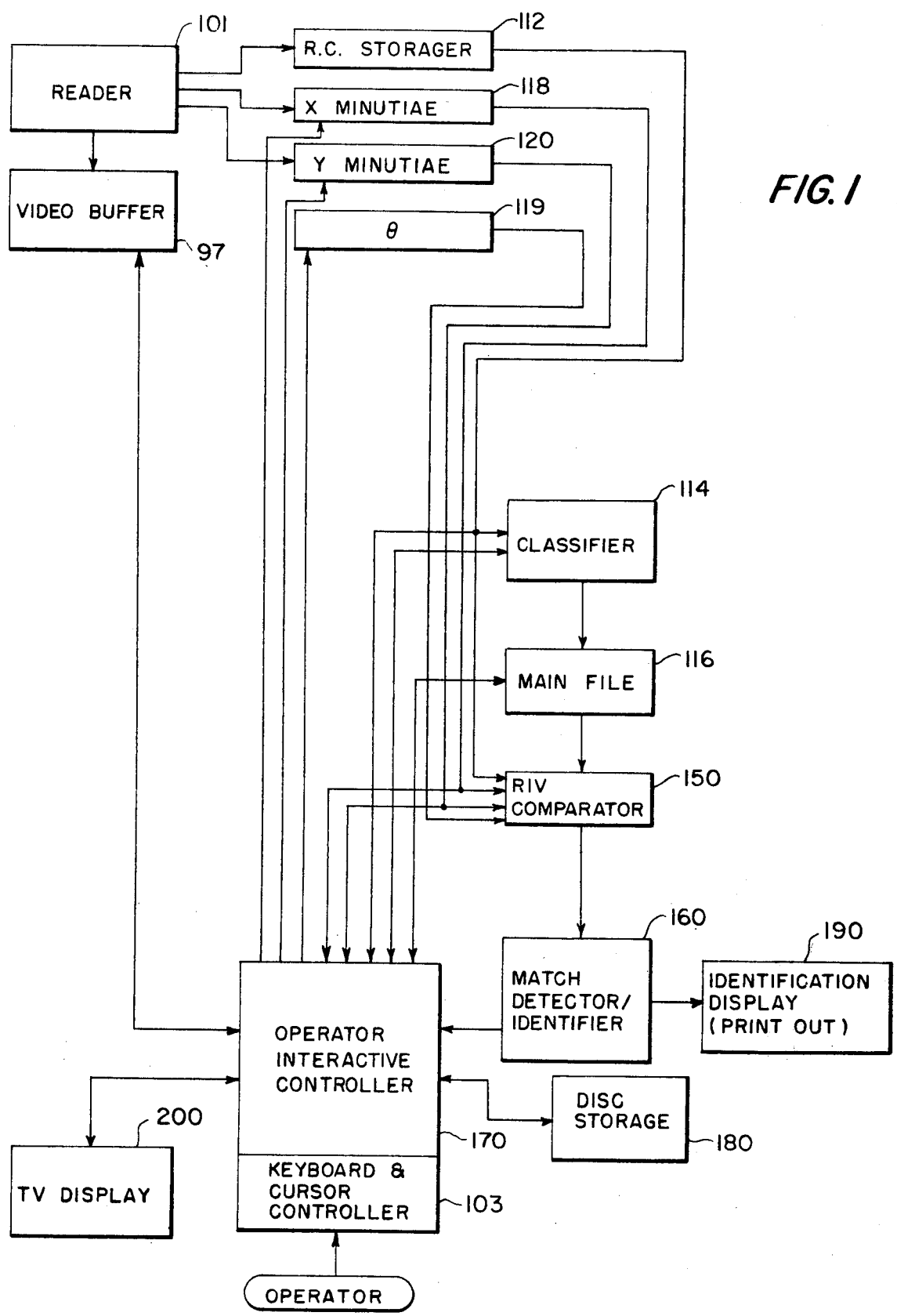
FIG. 1 is an overall block diagram illustrating the interactive system of the present invention.

FIG. 1 is an overall block diagram illustrating the intercommunication between the automatic portion of the operator interactive pattern processing system and the operator. In FIG. 1, a reader 101 scans a fingerprint image to be identified (unknown) and outputs both ridge contour data and the X-Y coordinates of detected minutiae, such as ridge endings and bifurcations, to respective storage elements 112, 118 and 120. The ridge contour data is then input to a classifier 114 which identifies the singularity points generally termed "tri-radii" and "cores", generates curve tracings of ridge contours associated with the identified singularity points, and compares the resultant curve tracings and located singularity points with reference data to determine a particular one of several predetermined classification types. In the present invention, if the classifier 114 identifies more than a predetermined number of singularity points or fails to determine a classification type for the particular fingerprint read by the reader 101, a signal is sent to an operator interactive controller 170. At this point, the automatic portion will dump out all of the data, so far derived from the scanned fingerprint, to a disc storage 180 where it is held for retrieval by the operator at his convenience. The automatic portion of the system will then continue to process other fingerprints in their turn. For the purpose of illuminating the unique characteristics of this system, it will be assumed that a single latent fingerprint is being read by the reader 101 and that the operator-interactive portion will be "on-line". Therefore, in this discussion, when the classifier indicates that no classification has been made on the scanned fingerprint, the operator, via the operator interactive controller 170, orders the information interpreted by the classifier 114 to be displayed on a T.V. display 200. At that point, the operator compares the number and location of detected singularity points and the associated curve tracings generated by the classifier 114 with a visual presentation of the fingerprint. Of course, the aforesaid controller 170 has the capability of superimposing the scanned fingerprint with the singularity points and curve tracings as automatically determined by the classifier 114 in order for the operator to make a rapid analysis of the situation. Employing a keyboard and a joy-stick type cursor control 103, the operator may adjust certain data which may have been erroneously detected by the automatic portion, such as the number and location of the singularity points or the associated curve tracings. The altered information is then input to the classifier 114, via the controller 170, and classification is again attempted to be made.

It should be noted at this point, that a hardware embodiment of the T.V. display 200, the keyboard with a joy-stick controlled cursor 103, buffer storage and interactive controller, as described herein, is commercially available from Princeton Electronic Products, Inc. of North Brunswick, New Jersey and is designated as a model PEP-801.

If the classifier 114 succeeds in classifying the fingerprint according to one of its reference classification types, the classifier 114 then accordingly addresses a main file 116 which stores a large volume of previously identified fingerprint patterns addressable by classification type, finger number, name, crime type, geographical location, etc. Any additional information on the fingerprint pattern to be identified, which may be effective to reduce the number of prints to be searched, may also be addressed into the main file 116. If, however, the classifier is again unable to classify the unknown fingerprint pattern, the operator may make an educated guess as to one or more classifications that he determines should be searched in the main file 116.

The addressed minutiae data read out of the main file 116, is then sequentially compared with the minutiae data read from the unknown fingerprint. An RIV (Relative Information Vector) comparator 150 compares each of the detected minutiae presented thereto in terms of X, Y and $\theta$ with each of the minutiae read out from the main file 116. X and Y represent the relative coordinate location for each of the detected and stored minutiae and $\theta$ represents the average angular orientation of the fingerprint pattern ridge lines at each X-Y coordinate location. The X-Y data for each minutiae is output from the storage means 118 and 120 respectively and the $\theta$ value is output from a ridge contour storage means 112, according to the relative X-Y location of that particular minutia. The RIV comparator 150 encodes each of the minutiae detected by the reader 101 and each of the minutiae of the addressed fingerprints stored in the main file 116 and performs a comparison of encoded minutiae data. The unknown fingerprint is compared, by the RIV comparator 150, with each of the addressed fingerprints in the main file 116 in sequence. For each comparison, a match score is output from the RIV comparator according to the degree of match between the fingerprint patterns. The match detector/identifier 160, determines which of the match scores produced by the RIV comparator are within a predetermined tolerance. Those scores which are within the tolerance are determined to be an acceptable match. The identity having the fingerprint data stored in the main file 116, which has been determined to be a match to the unknown fingerprint, is output from the match detector/identifier 160 to an identification display/print out 190.

In the event that no matches are produced by the match detector/identifier 160, a signal is output therefrom to the operator interactive controller 170. Such a signal would normally indicate that the number of minutiae detected by the reader 101 is insufficient to obtain a valid comparison in the RIV comparator 150. In such case, the operator interactive controller will superimpose the minutiae detected by the reader 101 onto an image of the unknown fingerprint and present the superimposed image to the operator on the T.V. display 200. The operator will then determine if the minutiae detected by the reader 101 is accurate and, if not, correct the same. In addition, the operator will examine the fingerprint image and determine if any additional minutiae are visually identifiable. When the operator detects that minutiae were misinterpreted by the reader 101 or not automatically detected thereby, he will locate the cursor at each misidentified or unidentified minutia point and, by utilizing the keyboard, command that the X, Y location and $\theta$ orientation of that minutiae point be appropriately stored.

Figure 2A:
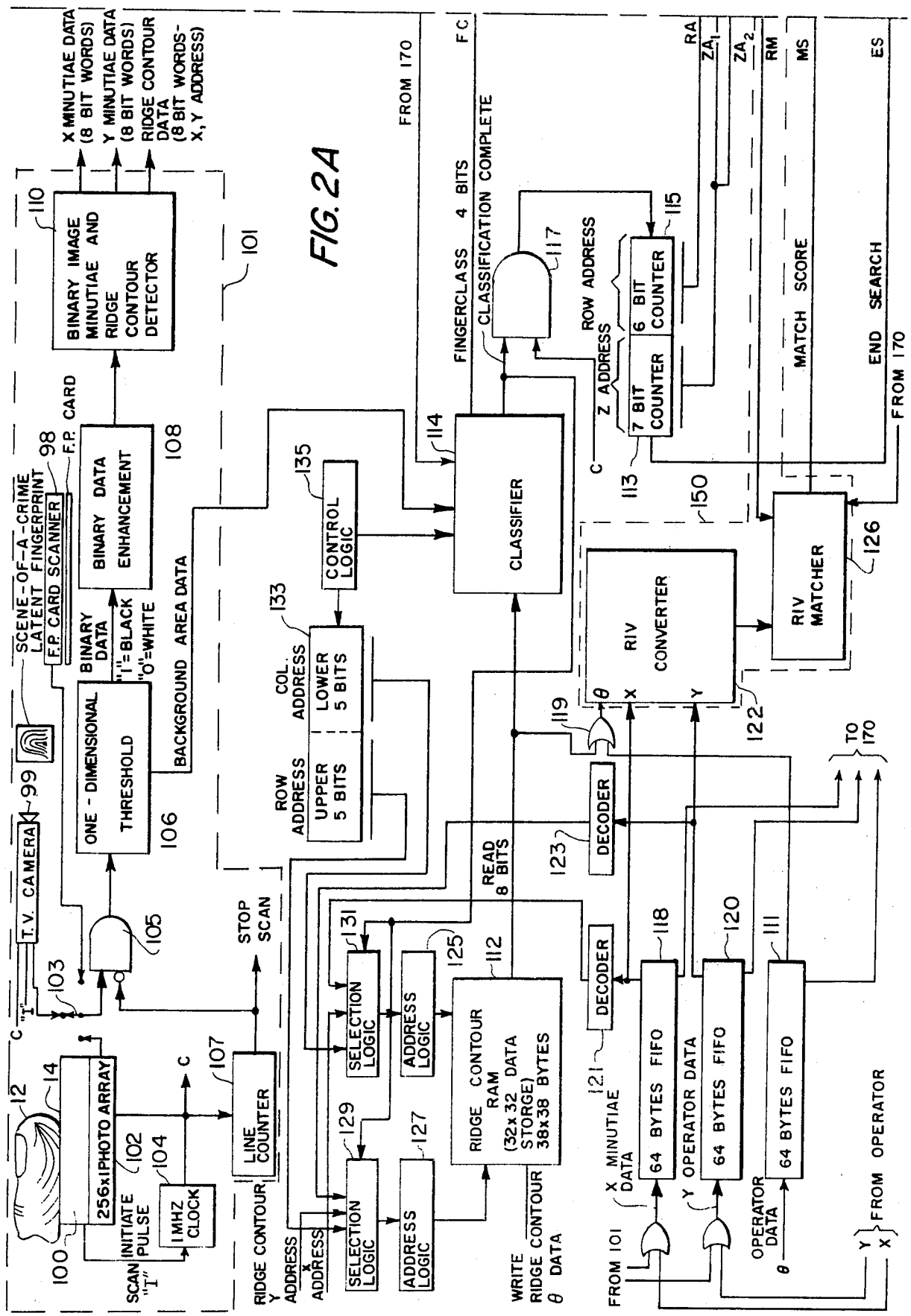
FIGS. 2A and 2B, hereinafter referred to as FIG. 2, illustrate a more detailed block diagram of the system shown in FIG. 1.
Figure 2B:
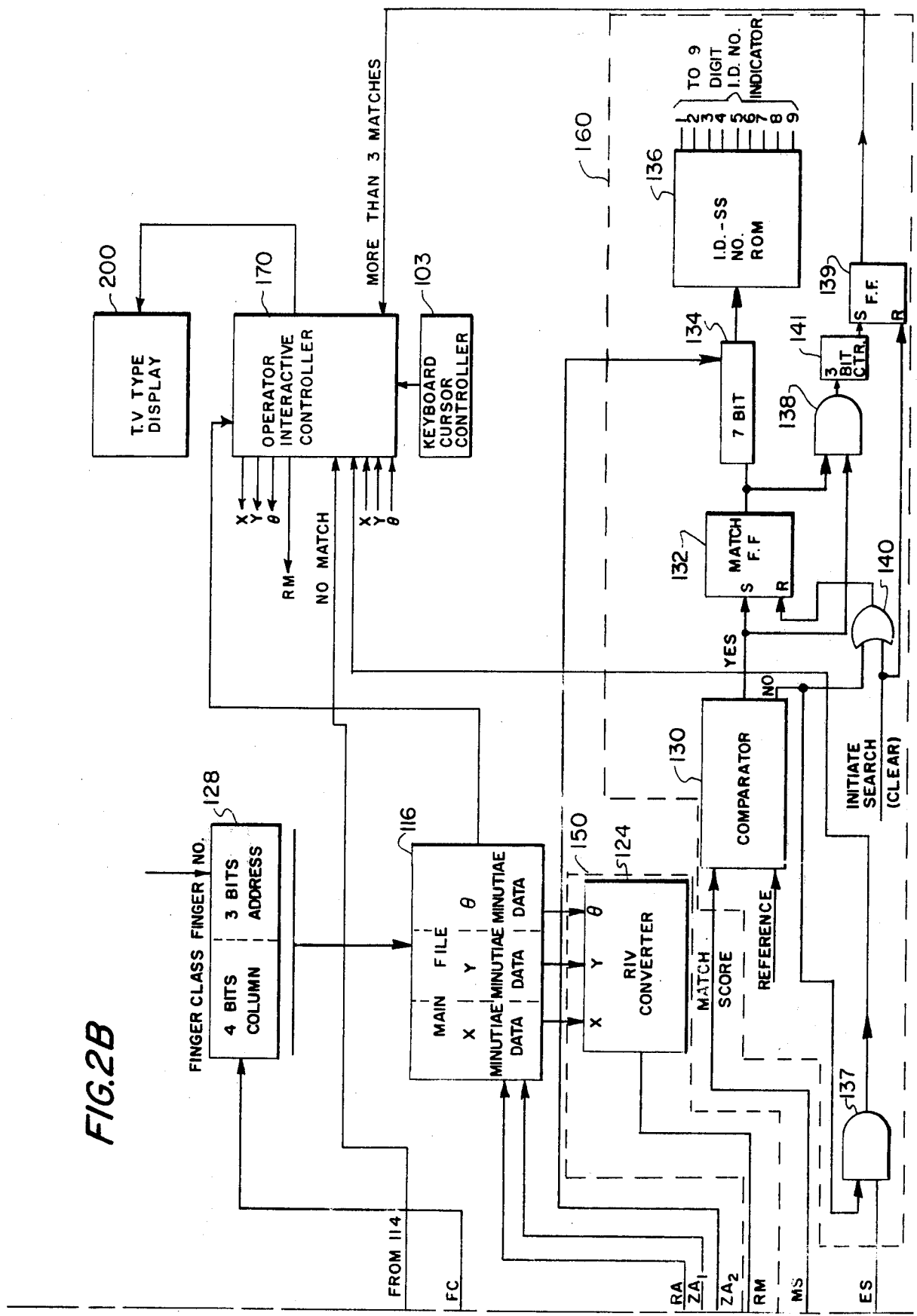

FIG. 2 is a more detailed block diagram of the system shown in FIG. 1, illustrating details necessary for data handling between each of the elements illustrated in FIG. 1.

The reader 101 is adaptable to read a live finger 12 impressed upon a scanning device 100, having a scan window 14 and a photo array 102 for line scanning the fingerprint image. The reader 101 is also adaptable to utilize a T.V. camera 99 which may be remote with respect to the overall system. The T.V. camera 99 may, for instance, be at a scene-of-a-crime location where immediate transmittal of "lifted" latent fingerprint images may be transmitted back to the system for processing and identification. It is, of course, understood that a video buffer must be located internal to the T.V. camera 99, or otherwise intermediate to the output signal from the T.V. camera, to make the raster scan of the T.V. camera compatible to the digital circuitry of the reader 101.

The reader 101 also includes a fingerprint card scanner 98 which may be a flying spot scanner which utilizes a light beam and a photo multiplier to line scan the inked and rolled fingerprint images recorded on the fingerprint card. Schematically represented switch 103 selects the particular input imaging device which is desired to be utilized by the system. For the purposes of the following discussion, it is assumed that a poor quality latent fingerprint is imaged and scanned by the T.V. camera 99 upon the command of the initiate scan pulse "I" and the scanned image is sampled by the clock pulses C from a 1 Mhz clock 104. In this case we have selected 256 sampling points per line and 256 successive lines for each scanned image. A line counter 107 counts the C pulses and produces a stop scan signal after 256 lines have been scanned (i.e., 65,536 clock pulses). During the scan, and AND gate 105 is enabled to pass the 256 data sampling points per line video buffered from the T.V. camera 99 to a one dimensional threshold circuit 106. Since the 256 data sampling points per line are actually analog data and may vary from a pure clock signal equalling a 1 to a pure white signal equalling a 0 the 1-dimensional threshold circuit 106 functions to quantize each of the sampled points to either a 1 or a 0 binary value and also identifies background area in those areas surrounding the latent fingerprint image. By contrasting the the latent fingerprint image as it is scanned by the T.V. camera 99, a pure white signal equalling a 0 can be made to surround the actual latent fingerprint image area while the actual image area is contrasted to a lesser white signal.

A binary data bit stream is output from the one-dimensional threshold circuit 106 to a binary data enhancement circuit 108 wherein the binary data is enhanced by removing undesirable variations in the pattern, without changing the unique characteristics of the pattern being processed. The binary data bit stream output from the one-dimensional threshold circuit 106 covers the entire scanned area including the background and the latent fingerprint image areas. The binary data enhancement circuit 108 thins the ridges of the pattern so that their widths occupy no more than one bit in the binary data bit stream. The binary data enhancement circuit 108 also acts to fill pores which appear in the ridge pattern and may cause discontinuities. An implementation of the binary data enhancement circuit 108 is found in our commonly assigned U.S. Pat. application Ser. No. 621,724, filed Oct. 14, 1975 entitled "Two-Dimensional Binary Data Enhancement System", and is incorporated herein by reference.

The enhanced bit stream from the binary data enhancement circuit 108 is input to the binary image minutiae and ridge contour detector 110, wherein the relative X, Y location of up to 64 minutiae are detected and the ridge contour data is determined. The minutiae and ridge contour detector 110 outputs the ridge contour data in 1024 words 8 bits in length, to a 32 byte × 32 byte ridge contour RAM 112. Each word of ridge contour data actually represents the average ridge angle in the scanned pattern over an 8 × 8 bit window comprising 8 bits per line of 8 scanned lines of the original scanned area of 256 scan lines per line by 256 lines. Therefore, each word of ridge contour data represents and 8 × 8 bit window area of the scanned area. Each of the 32 × 32 storage locations of the RAM 112, addressed through the selection and address logic circuits 131/125 and 129/127, stores an 8 bit word of ridge contour data which provides the average angle information for the corresponding 8 × 8 bit window. Since $2^8$ (8 binary bits/word) yields 256, then 256 distinct angles are detectable by the detector 110 and the system provides a resolution of approximately 1.4° as to the ridge contour angle information.

Minutiae, such as ridge endings and bifunctions, may number upwards of 100 in any particular fingerprint pattern. However, it has been determined empirically, that the number of valid minutia per print averages around 50. Therefore, in the present system, it is quite acceptable to identify and extract data for up to 64 minutiae and still achieve a high degree of accuracy in the match. In addition, 64 is a convenient figure to use in digital systems. Obviously, however, the size of the system could be modified by those skilled in this art to detect a larger number of minutiae than 64.

Each of up to 64 bytes of X data corresponding to the detected minutiae comprises 8 bits. Similarly, each of the up to 64 bytes of Y data corresponding to the same detected minutiae comprises 8 bits. The X and Y data describing the relative location of each detected minutiae are input to the minutiae data location storage registers 118 and 120 through respective OR gates 111 and 109. The minutiae data location storage register 118 and 120 are FIFO types which each store 64 bytes of information and supply their outputs to an RIV converter 122 in the RIV comparator 150.

The θ orientation for each detected minutiae corresponds to the average ridge contour angle data output from the binary image minutiae and ridge contour detector 110 at that corresponding X-Y location. Specifically, as the 8 bit words are output from the registers 118 and 120 to the RIV converter 122, they are also output to decoders 121 and 123 respectively. Selection logic elements 131 and 129 gate through the decoded X and Y minutia data information to address logic circuitry 125 and 127 respectively. The ridge contour RAM 112, containing the ridge contour θ data at 32 × 32 data locations, is addressed to read out the θ data according to the addressed position. The data read out from the ridge contour RAM 112 is then fed to the RIV converter 122 through an OR gate 119.

A FIFO type register 111 is shown adjacent to the FIFO register 120 which applies an output to the second input terminal of the OR gate 119. The FIFO 111 serves to store θ values received from the operator interactive controller 170, which are derived by the operator utilizing the keyboard/cursor unit 103 (described in detail below).

The basic approach taken in the RIV comparator section 150, is that even though two fingerprints of the same finger may not match perfectly (due to stretching or other distortions) if the minutiae patterns of these two fingerprints match sufficiently close, they can be considered to match each other. For this reason, there is a general overall match of two fingerprints for which it can be said that the fingerprints match. As a result, the RIV comparator section 150 is implemented to automatically determine how each and every little region of one fingerprint matches with each and every little region of the other fingerprint and then to put all these interim results together in a different space (something like the time domain versus frequency domain) to obtain the global picture. By this means, the RIV comparator 150 automatically determines whether or not the two fingerprints being compared are sufficiently similar to constitute a match.

Each little region of a fingerprint pattern is called a "Relative Information Vector" or RIV. An RIV is generated for each minutiae of the fingerprint pattern and is essentially a detailed description of the immediate neighborhood of that minutia. The minutia for which an RIV is generated is called the "reference" or "center" RIV minutia for that RIV. More specifically, an RIV describes the relative position, (r, θ) and direction (Δθ) for each one of a number of a minutiae in a predetermined neighborhood with respect to the center minutia of that RIV. The three parameters r, φ, Δθ of this relative position may be defined as follows:

$r_i$ is defined as the distance between the center minutia (at Xc, Yc) and the $i$th neighboring minutia of that RIV and thus, $r_i = |(Xc-Xi)^2 + (Yc-Yi)^2|^{1/2}$;

$\phi_i$ is defined as the angle between the tail of the center minutia and the location of the $i$th neighboring minutia of that RIV and this, $\phi_i = i$ arctangent $\Delta Y/\Delta X - \theta c$; and $\Delta\theta_i$ is defined as the difference between the angle of the tail of the center minutia ($\theta_c$) and the angle of the tail of the $i$th neighboring minutia ($\theta_i$), and thus, $\Delta\theta_i = |\theta c - \theta i|$.

Figure 3:
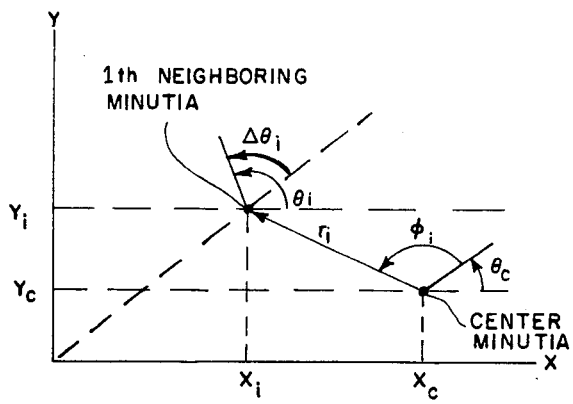
FIG. 3 illustrates the RIV parameters used to express a minutiae in terms of one of its neighbors.

Pursuant to the above definitions, the RIV parameters $r_i$, $\phi_i$ and $\Delta\theta$ of the $i$th neighboring minutia are illustrated in FIG. 3 for a center minutia with coordinates ($X_c$, $Y_c$, $\theta_c$).

As shown in FIG. 2, the RIV comparator 150 is basically comprised of RIV converters 122 and 124 and an RIV matcher 126. The RIV comparator 150 is responsive to minutiae for selectively generating a plurality of neighborhood comparison signals indicative of the closeness of match and coordinate displacements between minutiae neighborhoods of the compared patterns. The RIV comparator 150 is also responsive to the neighborhood comparison signals for developing output signals indicative of the relative closeness of match and relative coordinate displacement of the first and second fingerprints. The RIV converters 122 and 124 are responsive to minutiae of the two patterns for selectively developing a detailed neighborhood description of nearby surrounding minutiae for each of the minutiae of the first and second fingerprints. The RIV matcher 126 is selectively responsive to the detailed neighborhood descriptions of the two patterns for developing a plurality of neighborhood comparison signals indicative of the closeness of match and coordinate displacement between each minutiae neighborhood of the first pattern with respect to each minutiae neighborhood and the second pattern.

The output from the RIV converter 122 is input to the RIV matcher 126 wherein each RIV is compared with each RIV from RIV converter 124 which encodes minutiae data corresponding to an addressed fingerprint pattern read out from the main file 116. Details of the associated main file 116 are further described hereinbelow.

The RIV converters 122 and 124 operate identically and may be a single converter which operates on the minutiae of the two patterns in a time-sharing arrangement. They each sequentially transform input minutiae data in X, Y, $\theta$ format, from the pattern to be identified A (FP-A) and an identified pattern B(FP-B), into the relative information vector (RIV) format. The RIV matcher 126 compares each RIV of the fingerprint pattern A with each RIV of the identified pattern B and generates a match score for each RIV pair. The score is processed to analyze the set of RIV match scores from a global (overall) viewpoint and a final score is developed which quantitatively indicates the degree of similarity between the two fingerprints being compared.

This RIV comparator section 150 of the present invention is the subject of our copending U.S. patent application Ser. No. 722,308, filed concurrently herewith entitled "Minutiae Pattern Matcher" and is incorporated herein by reference.

Prior to the minutiae pattern matching performed by the RIV subsystem, a classifier 114 functions to classify the scanned fingerprint pattern into one of a selected number of classification pattern types of analyzing the ridge contour pattern information stored in the RAM 112. The classifier 114, of this embodiment, is capable of classifying a fingerprint into one of 16 classification types. The classification types in this instance are broken down into five sizes of left loops, five sizes of right loops, five sizes of whorls and an arch. Classifier 114, through control logic 135 and row and column address register 133, addresses the ridge contour RAM 112 to sequentially read out each of the ridge contour data words stored therein. The classifier 114 then analyzes the ridge contour data to identify singularity points, such as cores and tri-radii points which may be present, and processes the information to determine a classification of the fingerprint pattern. The classifier 114 outputs the classification type and produces an initiate match signal output which initiates a sequential search of the main file 116. Classification type output from the classifier 114 is a 4 bit "finger class" signal identifying which of the 16 classification types the scanned fingerprint pattern has been determined to be. A buffer 128 stores the 5 bit output along with a 3 bit selected finger number address signal (if available) for addressing the main file 116.

Figure 4:
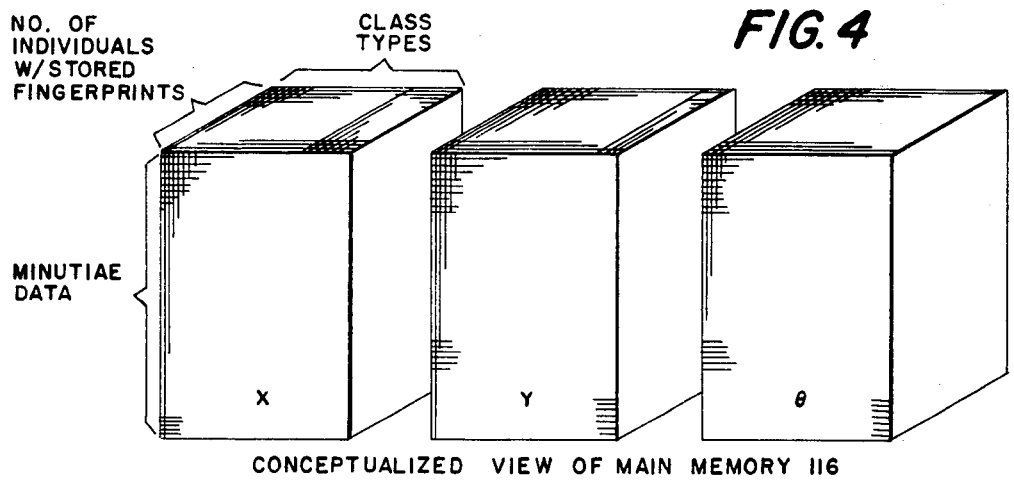
FIG. 4 is a conceptualization of the main file storage organization.

FIG. 4 shows a conceptualized view of the main memory file 116. From FIG. 4 it is possible to see that for each of the X, Y and $\theta$ data storage areas, classification type bins (in this case, 16) are provided for each of the number of individuals having fingerprint pattern data stored therein. The vertical dimension of the conceptualized main file 116 is sufficient to store the data corresponding to 64 detected minutia. Of course, it is understood, that the main file 116 may also provide additional breakdowns for finger number, crime type, geographical location and other identifying factors which would serve to reduce the number of fingerprints which are to be read out from the main file 116 and compared in the RIV comparator 150. For the purposes of the subject discussion, the conceptualized view of the main file 116, shown in FIG. 4, will suffice where the classification type is addressed to the main file and the "Z" addresses correspond to the individuals having fingerprint data stored in the main file. In this case the system sequentially addresses each of the Z positions. Those sequentially addressed Z positions having minutia data stored in the correspondingly addressed classification type bin will then be read out to the RIV converter 124 of the RIV comparator 150.

Simultaneous to addressing the main file 116, the buffer 128 also addresses the identification file 136, which in this case, is a ROM having a storage capacity corresponding to the main file 116 in order that the number of individuals having fingerprint data stored in the main file 116, will have corresponding identification data such as social security number stored therein. The function of the identification file 136 is to provide identification number for display whenever a match is determined between the fingerprint to be identified and the fingerprint data from the main file 116.

The X, Y and $\theta$ minutiae data read out from the main file 116 is input to the RIV converter 124 which is identical to the RIV convertor 122. The output of the RIV converter 124 is fed to the RIV matcher 126. In the RIV match 126, each relative information vector from the RIV converter 122 is compared with each relative information vector from the RIV converter 124. In accordance with the RIV discussion above, a 7 bit match score is produced by the RIV matcher 126 in accordance with each of the number of sequenced fingerprint patterns stored in the main file 116.

The 7 bit match score output from the RIV matcher 126 is fed to a comparator 130 which compares the 7 bit match score with a predetermined reference value. Whenever the 7 bit match score exceeds the reference value, a "match" is determined between the scanned fingerprint pattern and the addressed pattern. The match signal is output from the comparator 130 and is input to a match flip-flop 132. The match flip-flop 132 is set, and its latched output is fed to a Z address 7 bit counter 134, which addresses the identification ROM 136 to effect a read out of the identification numbers discussed above. In the system where several hundred or several thousand fingerprints are stored in the main file 116, it is quite possible and highly probable that more than one match will be produced. The match flip-flop 132 is reset by the output of the OR gate 140, and in the event that more than one match is obtained during the sequential search of the main file 116, the identification ROM 136 is again addressed. The correspondingly addressed identification number is then output and displayed or recorded. Simultaneously, an AND gate 138 causes a three bit counter 141 to count up one bit for each match. The 3 bit counter 141 was selected in this case so that whenever more than 8 matches are determined for any one scanned fingerprint, an indication will be made to the operator that the system has a low confidence in its ability to match the particular scanned fingerprint.

The output from the 3 bit counter 141 sets the flip-flop 139 and produces a signal to the operator interactive controller 170 and indicates to the operator that the system is producing an excessive number of matches. At that point, the operator may address the main file 116 through the operator interactive controller 170 and read out the minutiae data for each of the patterns that was determined by the system to match the scanned fingerprint, and visually determine to what extent the minutiae patterns match. The operator may determine that the reference level for comparison at the comparator 130 is set too low and that the reference level should be adjusted upward to reduce the number of matches by requiring a higher match score.

Alternatively, the operator may determine that a particular high density cluster of minutiae in the scanned pattern causes a high score from the RIV comparator 150. The operator can then cancel the high density cluster of minutiae of the scanned pattern and allow the system to compare the scanned fingerprint based upon the remaining detected minutiae in the scanned pattern.

If, at the end of the search of the main file 116, no match has been determined, an overflow bit from the address counter 113 indicating that the main file 116 has been completely searched, is gated through the AND gate 137. The AND gate 137 is enabled by the "no" output of the comparator 130 and produces a signal to the operator interactive controller indicating that the no match has been made. A no match indication is sufficient for the operator to analyze the extracted minutiae data from the scanned fingerprint and verify that the extracted minutiae data is valid, with respect to the visual image of the fingerprint. If the operator determines that any or all of the minutiae extracted from the scanned fingerprint are in error, he manually identifies corrects and/or cancels the X, Y location and $\theta$ orientation of the minutiae which is in error, or is questionable, by use of the cursor displayed on the TV type screen 101 and controlled by a joy stick at the keyboard/cursor operator input terminal 103. Each of the minutiae located by the operator is input to the appropriate X, Y and $\theta$ storage registers 118, 120 and 111 via the operator interactive controller 170.

After verifying the minutiae data and correcting it where necessary, the operator will visually compare the ridge contour data extracted by the system with a superimposed image of the fingerprint to be identified. The operator will correct any portion of the data that he sees as being misinterpreted by the system so that the system will be able to make a good attempt at classifying and comparing.

Figure 5:
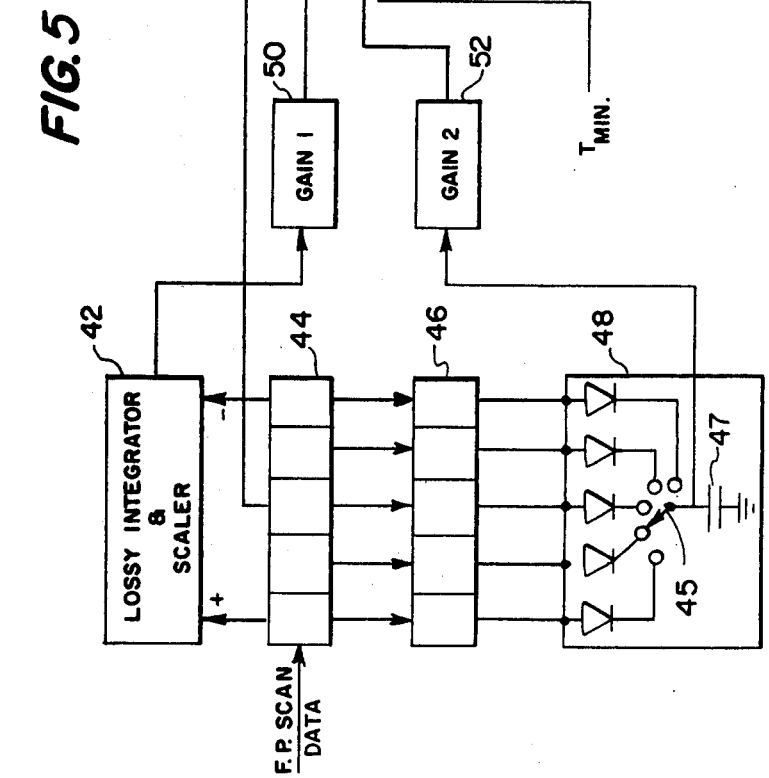
FIG. 5 is a detailed block diagram of a 1-dimensional threshold circuit shown in FIG. 2.

Referring to FIG. 5, the 1-dimensional threshold circuit 106 is shown in detail. As mentioned previously, the input to the circuit is an analog signal corresponding to 256 data points per line as sequentially output from the scanner selected by the switch 103. The analog signals are discrete in the sense that they are input to the 1-dimensional threshold circuit 106 in synchronization with the clock pulses C. The analog signals are processed through a five stage analog buffer 44 such as a CCD. As is well known, a CCD has the ability to transfer sampled analog values along each stage thereof.

The first and last sample values present in the five stage analog buffer 44 are supplied to a lossy integrator and scaler 42 which produces a five point average output signal to a first gain control 50 at a first input to an adder circuit 54.

The values present in each of the five stages of the five stage analog buffer 44 are output to corresponding stages of buffers 46. The output of each corresponding stage of buffer 46 is connected to an associated diode in a "peak black" selection circuit 48.

A scanning switch in the selection circuit 48 scans each of the associated diodes and causes the capacitor 47 to charge to a value corresponding to one of the five outputs. The value of the charge on the capacitor 47 is coupled to the second gain control 52 at the second input of the adder circuit 54.

The third input to the adder circuit 54 is shown as $T_{min}$. The input $T_{min}$ is a preselected minimum threshold value which is used as a reference for the adder circuit 54. The adder circuit 54 supplies a threshold value to the voltage discriminator 56. The threshold value output from the adder 54 is variable for each sampling point and is determined by the $T_{min}$ and the two outputs from the gain controls 50 and 52. The voltage discriminator 56 receives the third sampled value from the five bit stage analog buffer 44 and supplies a binary output by referencing that sampled analog signal to the variable threshold input signal.

The voltage discriminator 58 is all shown in the 1-dimensional threshold circuit 106 as distinguishing the background area from the fingerprint pattern area. A "peak whiteness" threshold reference voltage is supplied to one input of the voltage discriminator 58 and is compared with the third sample value from the five stage analog buffer 44 and supplies a binary 1 , where the whiteness of the sample value is greater than the peak whiteness threshold reference, and a binary 0, where the whiteness of the sample value is less than the peak whiteness threshold reference.

The enhanced binary bit stream from the binary data enhancement circuit 108 is a thinned version of the data derived by scanning the finger. The resulting bit stream is enhanced to a degree wherein any 3 × 3 bit window will contain no more than a single line corresponding to a ridge of the fingerprint pattern.

Figure 6D:
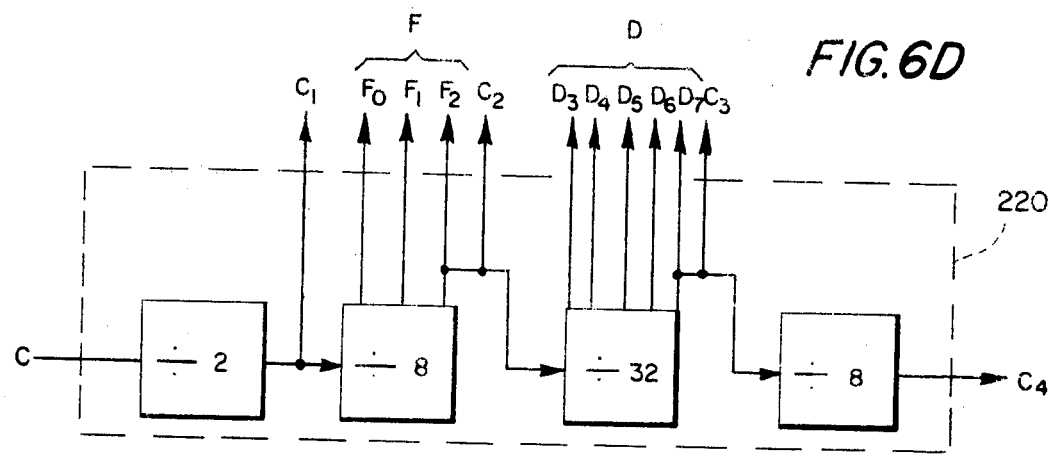
Figure 6E:
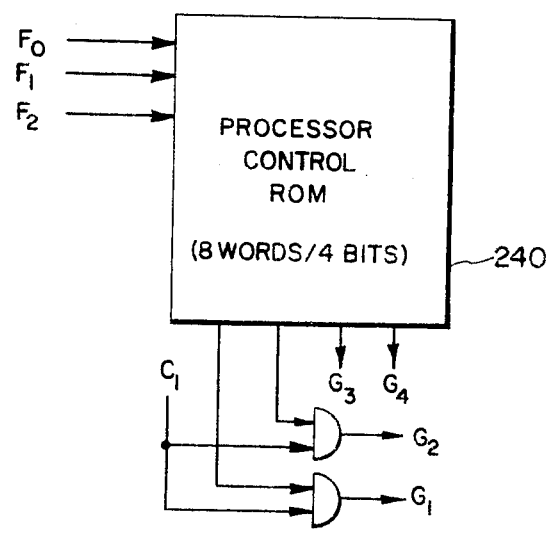
Figure 6F:
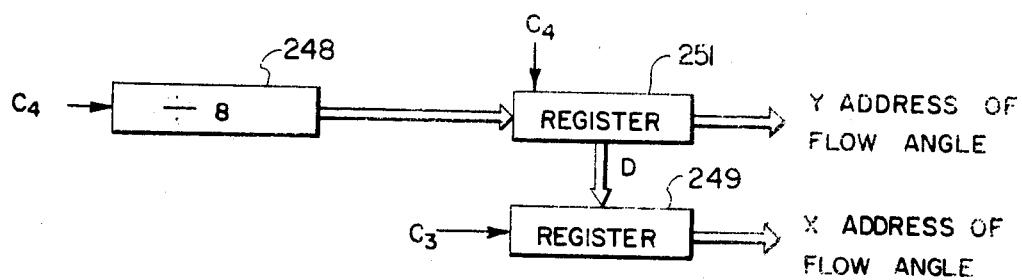

The detailed block diagram of the binary image minutiae and ridge contour detector 110 is shown in FIG. 6. An implementation of the binary image minutiae and ridge contour detector 110 is found in our commonly assigned U.S. Pat. application Ser. No. 722,307, filed concurrently, entitled "Binary Image Minutiae Detector" and is incorporated herein by reference.

The binary image from the binary data enhancer 108 is serial input to a 256 bit serial-in/serial-out delay register 202 and to a 3-bit serial-in/parallel-out register 206. The output of the 256 bit delay register 202 is fed to a second 256 bit delay register 204 and to a serial-in/parallel-out register 208. The output from the second 256 delay register 204 is fed directly to a third 3-bit serial-in/parallel-out register 209. The three 3-bit registers 206, 208 and 209 form a 3 × 3 bit scanning window which scans nine bit sampled areas of the enhanced image one bit at a time. The 3 × 3 window therefore contains bit stream information corresponding to a nine bit sample of three adjacent bits per line on three adjacent lines. Timed with the clock pulses, the 3 × 3 window scans along the fingerprint pattern one bit by one bit to the end of that line, shifts to the next line and scans along that line.

The line parallel output signals from the 3 × 3 window are fed to a 256 × 2 minutiae detection ROM 212 for the detection of minutia. The minutiae detection ROM 212 is programmed so that if a minutia is present and centered in the 3 × 3 window, the signals A1-A9 correspond to a minutia address. Each possible address corresponding to a detected minutia in any position, is stored in the 256 × 2 ROM 212. FIG. 7 shows 24 addresses which are effective to read out, from twenty-four corresponding locations in the ROM 212, a 2 bit value indicating that a bifurcation or ridge ending is detected. $M_1$ and $M_2$ indicate the 2 bit output from the ROM 212. When a bifurcation is detected $M_1 = 1$ and $M_2 = 0$. When a ridge ending is detected, $M_1 = 0$ and $M_2 = 1$.

In order to reduce the size of the ROM 212 to a 256 bit dimension with 512 address possibilities, ($2^9$), the center bit (A 5) from the 3 × 3 window is routed to a logic circuit external to the ROM 212, leaving eight address inputs to the ROM 212.

Since the proper location of a bifurcation in a 3 × 3 window, presents a binary 1 signal at the center bit location (A5) of serial-parallel register 208, the A5 signal from the center location of the register 208 is directly input to an AND gate 216. The combined signal A5 and the M1 (1) and M2 (0) signals from the ROM 212, are input to the AND gate 216 to produce an output which is gated through OR gate 218 to provide a minutia detection signal.

When the 3 × 3 window is centered on a ridge ending, a correct address will appear at the input to the ROM 212 and a binary 1 signal will be read out of the ROM 212 at M2 and a 0 signal will be read out at M1. When a ridge ending is correctly centered in the 3 × 3 window the A5 signal is a 1 and is directly input to an AND gate 214. The M1 and M2 outputs of the ROM 212 and the A5 signal at the input to the AND gate 214, produce a signal which is gated through the OR gate 218 to produce a minutia detection signal. Therefore, although the A1-A4, A6-A9 address may address a location of the ROM 212 which has a 2 bit value stored therein to indicate a minutiae detection the A5 signal must be a proper binary value to gate the ROM 212 output through the gates 214, 216 and 218 as a minutia detection signal. The minutia detection signal latches two 8-bit latches 213 and 215, which then hold respective X and Y addresses for the detected minutia. The derivation of the Y address corresponds to the number of $C_3$ clock signals from a divider circuit 220, counted by a counter 211. The X address corresponds to the combination of D and F signals from divider circuit 220 and latched by minutia detection signal from the or gate 218.

Now referring to the ridge flow detection section of FIG. 6, a 512 × 4 ROM 210 is shown which receives the address output from the 3 × 3 window formed by the serial-in/parallel-out 3-bit registers 206, 208 and 209. The ROM 210 is preprogrammed to read out a specific local angle in accordance with 12 different addresses.

The 12 different addresses symbolizing the various ridge flows through the 3 × 3 window are shown in FIG. 8. As seen in FIG. 8, 12 different patterns of a single line extending through the 3 × 3 window result in 12 different addresses. However, since some of the patterns are identical in deriving an angle value indication, the local angle values indicated by the ROM 210 readout a total 8 different angle indications. Any other patterns which exist in the 3 × 3 window are ignored for purposes of identifying ridge flow information and accordingly, zeros are read out for those unprogrammed address locations. The 12 selected angle values corresponding to 12 adresses to the ROM 210 (subject to ± 180° as to four thereof) result in eight coded local angle values ($D_0$–$D_2$). An output E from the ROM 210 provides an enabling signal whenever one of the eight possible local angle locations in the ROM 212 is addressed. The enable signal E essentially identifies that an angle for which the ROM 210 is programmed has been produced by a particular address input with values A1-A9 of a given 3 × 3 window.

Referring again to FIG. 6, dividing circuit 220 supplies various clocking signals as a result of dividing the main clock signals C from the main clock 104 shown in FIG. 2.

The three bit output $D_0$–$D_2$ from the ROM 210 and the $D_3$–$D_7$ clocking pulses, supply the eight bit address through an adder 224 to an input multiplexer 223. Whenever a local angle is output from the ROM 210, the enable bit E is applied to the adder 224 and the corresponding eight bit address present therein is applied to the input multiplexer 223 which alternately applies said eight bit address to either a 256 byte × 8 bit RAM 221 or a 256 byte × 8 bit RAM 222. The output multiplexer 226 operates in alternate time frames with the input multiplexer 223 such that the data is read into RAM 221 from the multiplexer 223 while data is read out of RAM 222 by the multiplexer 226 for processing. Likewise, data is read into RAM 22 while data stored in RAM 221 is read out and processed. This multiplexing technique is used since the processing rate far exceeds the rate of which data storage occurs in the RAMS 221 and 222 and hence, adequate time is available for the alternating function provided by the multiplexer 223 and 226.

Each of the RAMS 221 and 222, when fully loaded with data from the input multiplexer 223, ultimately stores a count value of the number of occurrences of each of the local angles defined by the output of the ridge ROM 210 for an 8 × 3 bit window. In this case, the 8 × 8 bit windows are fixed windows occupying predetermined 8 bit × 8 bit portions of the total image. This is in contrast to the 3 × 3 window discussed above, which scans over the entire image one bit by one bit. Therefore, the ultimate objective is to read the local angle information derived by the 3 × 3 bit window scan and process it to produce a single angular representation which is an average of the ridge lines present in the 8 × 8 bit window. The accumulation of the number of occurrences of each of the eight possible local angles within the 8 × 8 bit window provides a basis for achieving a weighted average of those local angles in deriving the counter angle for that particular 8 × 8 bit window. Whereas each 3 × 3 bit window represents the local angle of a single scanned ridge line, the 8 × 8 window represents a ridge contour angle value comprising the average of a number of ridge lines which may be present in that larger portion of the scan array.

The D output values ($D_3$–$D_7$) from the divider circuit 220, define each of the 32 (8 × 8 bit) window locations across a given line scan (256 bits) of the image. The D values, along with the D0–D2 signals defining the local angle, are supplied through the input multiplexer 223 as described above.

Each RAM 221 and 222 stores 256 bytes (8 bit/byte) over eight scanned lines. Therefore, the contents of each RAM represents 32 (8 × 8 bit) windows. Consequently, each 8 × 8 bit window is represented by 8 words 8 bits in length, wherein each of the 8 words represents one of eight possible local angles. The D and F signals form an address which accesses each group of eight angles for each of the 32 windows in a sequence. For each 8 × 8 window, the corresponding eight angles are accessed by incrementing through the F signals and accumulating the results in register 231 and 232. When the eight angles for each 8 × 8 window are accumulated, the $C_2$ signal processes the results through ROM 246 and the eight bit buffer 247 and resets registers 231 and 232 to be ready for the next 8 × 8 window.

The function of registers 231 and 232 along with their respective adders/subtractors 230 and 233 is to get an approximate average of the sine and cosine projection of the average vector direction. The averaging operation is under control of the processor control ROM 240. The particular addresses from the clocking signal $F_0$, $F_1$ and $F_2$ and corresponding readouts from the ROM 240 are shown below.

TABLE I

| PROCESSOR CONTROL ROM | | | | | | |
|---|---|---|---|---|---|---|
| ADDRESS | | | OUTPUTS | | | |
| $F_2$ | $F_1$ | $F_0$ | $G_1$ | $G_2$ | $G_3$ | $G_4$ |
| 0 | 0 | 0 | 0 | 1 | 0 | 1 |
| 0 | 0 | 1 | 1 | 1 | 1 | 1 |
| 0 | 1 | 0 | 1 | 0 | 1 | 0 |
| 0 | 1 | 1 | 1 | 1 | 1 | 0 |
| 1 | 0 | 0 | 0 | 1 | 0 | 0 |
| 1 | 0 | 1 | 1 | 1 | 0 | 0 |
| 1 | 1 | 0 | 1 | 0 | 0 | 0 |
| 1 | 1 | 1 | 1 | 1 | 0 | 1 |

The output bits $G_3$ and $G_4$ control the adder/subtractor circuits 230 and 233 respectively. If $G_3$ is 1, the adder 230 adds; if $G_3$ is 0, the adder 230 subtracts. Similarly, $G_4$ controls the adder/subtractor circuit 233. The other outputs $G_1$ and $G_2$ are anded with a clock pulse $C_1$ and form strobe signals to the adder/subtractors circuits 230 and 233. These strobe signals cause the adder/subtractor circuits to add or subtract in accordance with the control signals discussed above. Therefore, when strobe pulses are not supplied, the output from the multiplexer 226 is ignored by the corresponding adder/subtractor circuit. The five most significant bits of each register 231 and 233 are combined into a ten bit address that is applied to a ROM 246. The function of the ROM 246 is to perform an approximate talbe look-up arctangent calculation. The contents of a particular location in the ROM 246 comprise the angle associated with the address defined by the sine and cosine projections as output from registers 231 and 232.

The output of the ROM 246 is strobed into the 8 bit buffer register 247 for holding and transmittal to the ridge contour RAM 112 (FIG. 2). The X address is derived upon the occurrence of the clock pulse $C_3$ entering the data into holding register 249, and similarly, the Y address of the ridge flow data is entered into holding register 257 from the vertical window address counter 248.

As shown in FIG. 2, the ridge contour data including the flow angle and the X-Y address of each flow angle is output to a ridge contour RAM 112. The ridge contour data comprises an 8 bit X address, an 8 bit Y address, and an 8 bit angle value. The ridge contour RAM 112 has dimensions of 38 × 38 bytes wherein a 3 byte border is provided for a 32 × 32 byte storage array. The 3 byte border is preprogrammed to a preselected value so as to always represent the absence of data storage in that border. Therefore, the ridge contour data is addressed to the 32 × 32 byte matrix within the surrounding 3 byte border. The purpose of the border will be shown in the following discussion with reference to the classifier 114.

The classifier 114 as shown in FIG. 2, serves to define the general classification type for which the scanned fingerprint pattern may be classified. Due to the large number of fingerprints which may be stored in the main file, it is necessary to classify each of the fingerprint patterns in accordance with established rules well known to those skilled in this art. In this embodiment, a classification system is utilized wherein the fingerprint pattern is classified as an ARCH, WHORL or LOOP. Since it is statistically known, that approximately ⅔ of the fingerprint patterns are classified as loop types, approximately 1/5 are whorls and the substantial remainder are arch type, the present embodiment preliminarily classifies the patterns as loop type, whorl type or arch type, based upon the number of singularity points located. The loop is broken down into left and right loops of five different sizes and the whorl is broken down into five different sizes. Due to the relatively infrequent ocurrence of arch type patterns, the present embodiment does not provide for further breakdown. However, further breakdown could be made using the disclosed classification techniques, if desired.

FIGS. 9A, 9B and 9C show the fingerprint pattern as it is presented to the scanner, the ridge flow pattern as it is stored in the ridge contour RAM 112 and contour tracings as produced in the classifier for right loop, left loop and whorl classifications, respectively. FIGS. 9A, 9B and 9C are intended to illustrate and summarize the steps that are employed by the system preliminarily to clarifying the fingerprint.

Figure 10:
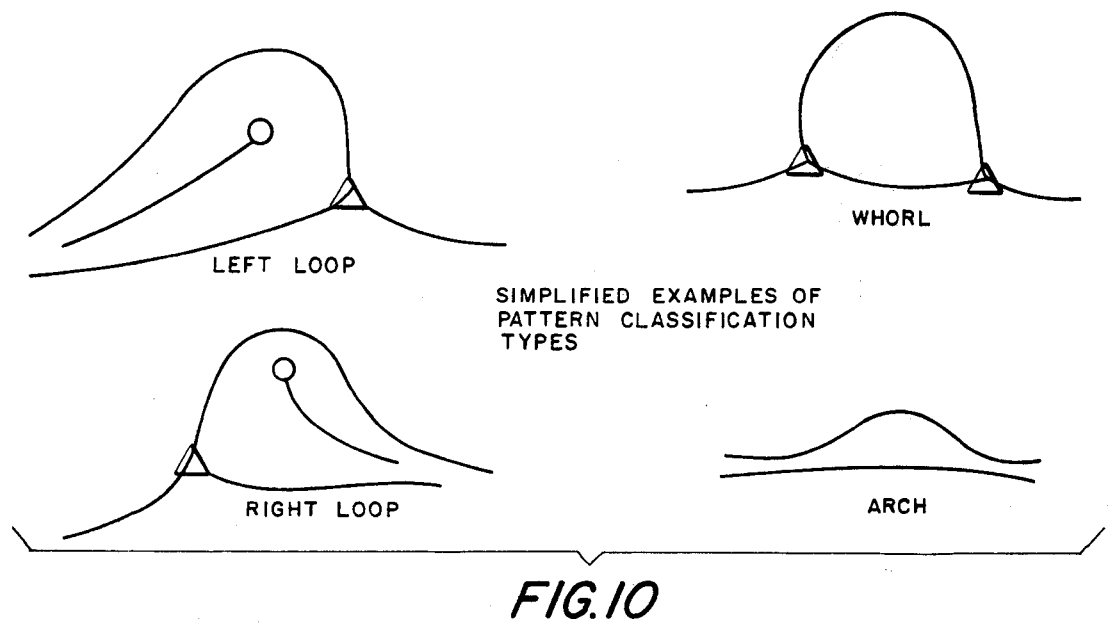
FIG. 10 illustrates simplified examples of pattern classification types.

In FIG. 10, simplified examples of pattern classification types are shown wherein the left loop and right loop are distinguished according to their flow with respect to a single tri-radii point (marked with a delta) and a core point (marked with a circle). The whorl is also shown which is identified by the existence of two tri-radii points and no core points. An arch is shown which is defined as a pattern having no tri-radii points and no core points therein.

Figure 11:
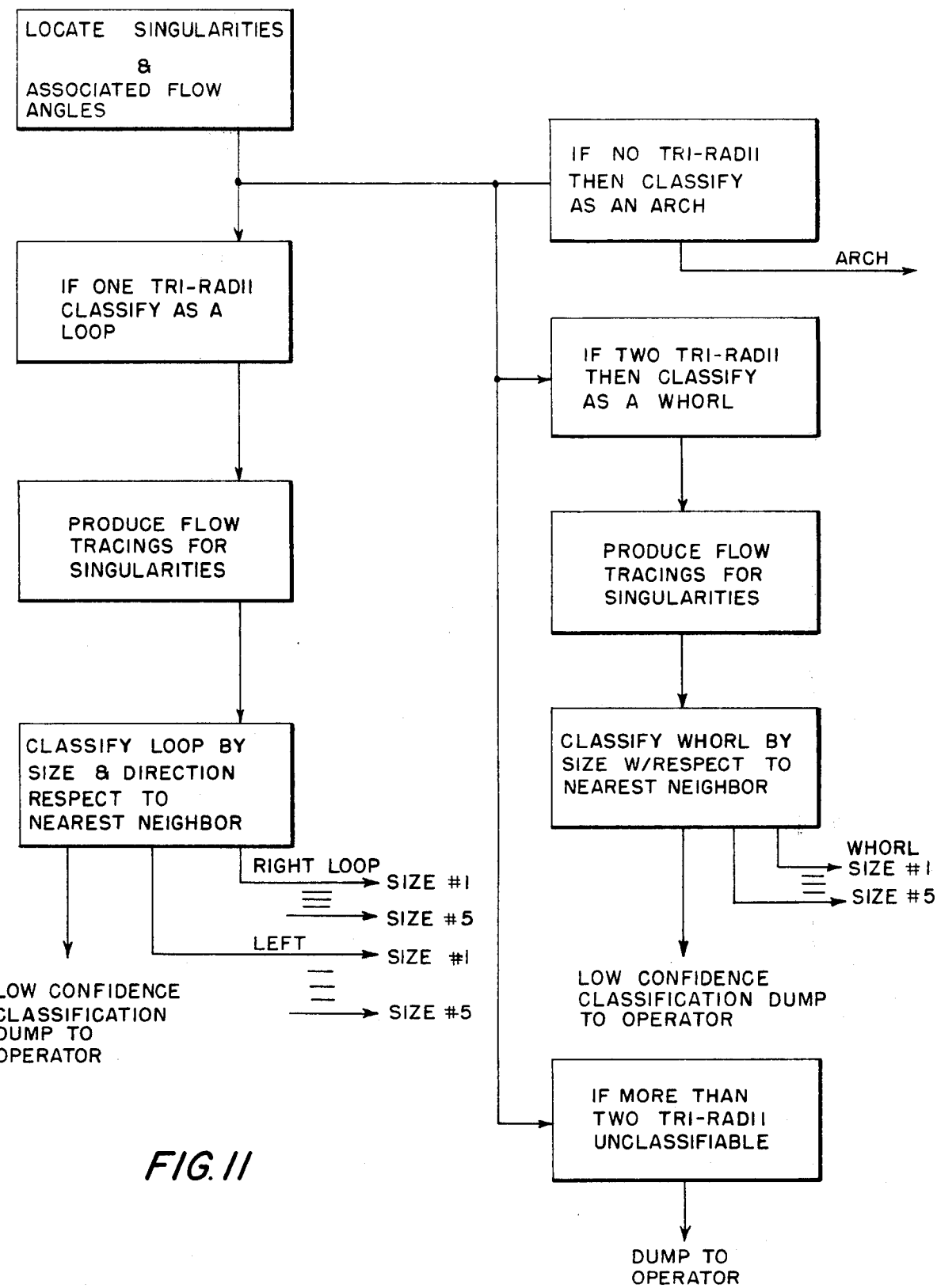
FIG. 11 is a simplified block diagram of the classifier shown in FIG. 2.

FIG. 11 shows a functional flow diagram of the classifier 114. The first function of the classifier is to locate singularities such as cores and tri-radii points and identify the associated flow angles at those points. Correspondingly, a core point will have one associated flow angle and a tri-radii point will have three associated flow angles. Based upon the number of singularities located, an initial classification can be made wherein an arch type is identified if no tri-radii and no core points are located, a general whorl type may be identified if two tri-radii and no core points are located, and a general loop type may be identified if one tri-radii and one core point is located. However, if the pattern is classified as either a whorl or a loop type, further processing is necessary in order to achieve a further definition of the classification type. In this further classification process for the whorl and loop, flow tracings are produced along the associated flow angles from each of the located singularities according to the extracted ridge contour data discussed above. From the flow tracings, the loop type pattern is classified according to direction and size by comparing it with a set of pre-stored references. The classification information is then output in a four bit word to the main file 116 as shown in FIG. 2.

Figure 12:
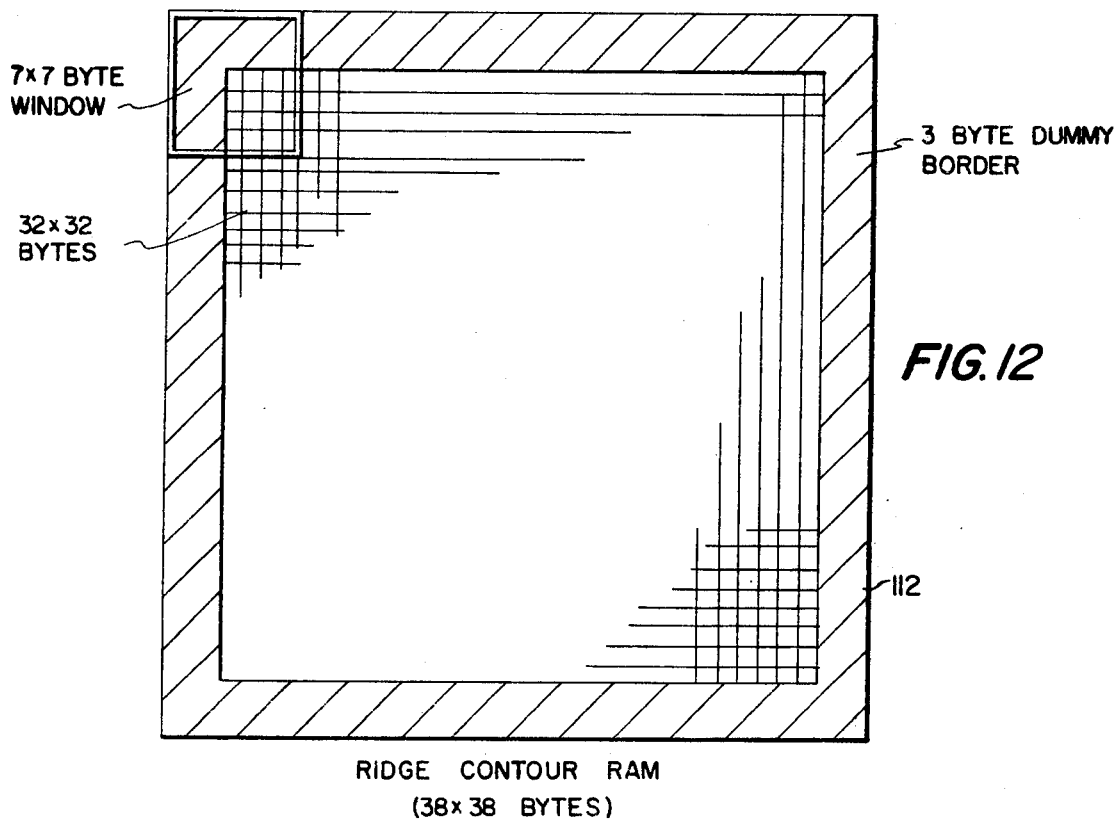
FIG. 12 illustrates a 38 × 38 byte ridge contour RAM with 32 × 32 bytes of storage area and a 7 × 7 byte window.
Figure 13:
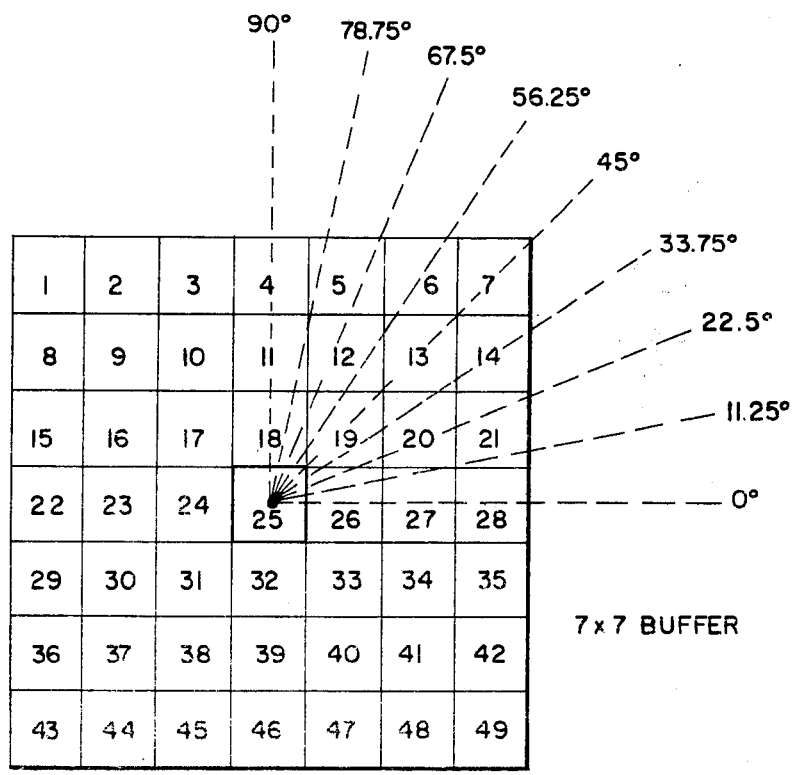
FIG. 13 illustrates a 7 × 7 buffer used to determine the correlation of reference angles.

In order to locate singularities such as cores and tri-radii points, the ridge contour RAM 112, shown in FIG. 12, is scanned by a 7 × 7 byte window to determine the correlation of the average ridge flow in the vicinity of the ridge contour element in the ridge contour RAM 112 centered in the 7 × 7 byte window with respect to each of the 32 reference angles encompassed by the 7 × 7 byte window (see FIG. 13).

The correlation is measured by computing the cosine of the angular difference between the current reference angle and the average contour angle in the reference direction.

subtracted from the reference value for 0°. A cosine "table-look-up" ROM is utilized to produce a cosine value depending upon the subtracted value. The cosine values for all of the angular differences are then summed to produce an 8 bit output which is the correlation for $\theta_R = 0°$. Accordingly, circuitry is shown for $\theta_R = 11.25°, 22.5°$ and $33.75°$. In each of the four circuits, calculations are made to determine 8 bit correlation values for each of the $\theta_R$'s. Since the present system analyzes 32 values of $\theta_R$, it is apparent that the four calculation circuits illustrated in FIG. 14, may be reproduced eight times to yield a total of 32 circuits providing the respective 32 outputs. Accordingly, Table II is illustrated below and sets forth the approximate coefficient values used in the corresponding summation legs of each circuit. The indicators in the "approximate coefficients" columns of Table II correspond to the cell designations in the 7 × 7 buffer shown in FIG. 13.

TABLE II

| $\theta_R$ | APPROXIMATE COEFFICIENTS | | | $\theta_R$ | APPROXIMATE COEFFICIENTS | | |
|---|---|---|---|---|---|---|---|
| 0° | 26 | 27 | 28 | 180° | 24 | 23 | 2 |
| 11.25° | 26 | $\frac{20+27}{2}$ | $\frac{21+28}{2}$ | 191.25° | 24 | $\frac{23+30}{2}$ | $\frac{22+29}{2}$ |
| 22.5° | $\frac{19+26}{2}$ | 20 | 21 | 202.5° | $\frac{24+31}{2}$ | 30 | 29 |
| 33.75° | $\frac{19+26}{2}$ | $\frac{13+20}{2}$ | 14 | 213.75° | $\frac{24+31}{2}$ | $\frac{30+37}{2}$ | 36 |
| 45° | 19 | 13 | 7 | 225° | 31 | 37 | 43 |
| 56.25° | $\frac{18+19}{2}$ | $\frac{12+13}{2}$ | 6 | 236.25° | $\frac{32+31}{2}$ | $\frac{38+37}{2}$ | 44 |
| 67.5° | $\frac{18+19}{2}$ | 12 | 5 | 247.5° | $\frac{32+31}{2}$ | 38 | 45 |
| 78.75° | 18 | $\frac{11+12}{2}$ | $\frac{4+5}{2}$ | 258.75° | 32 | $\frac{39+38}{2}$ | $\frac{46+45}{2}$ |
| 90° | 18 | 11 | 4 | 270° | 32 | 39 | 46 |
| 101.25° | 18 | $\frac{11+10}{2}$ | $\frac{3+4}{2}$ | | | | |
| 112.5° | $\frac{18+17}{2}$ | 10 | 3 | 281.25° | 32 | $\frac{39+40}{2}$ | $\frac{46+47}{2}$ |
| 123.75° | $\frac{18+17}{2}$ | $\frac{10+9}{2}$ | 2 | 292.5° | $\frac{32+33}{2}$ | 40 | 47 |
| | | | | 303.75° | $\frac{32+33}{2}$ | $\frac{40+41}{2}$ | 48 |
| 135° | 17 | 9 | 1 | | | | |
| 146.25° | $\frac{17+24}{2}$ | $\frac{9+16}{2}$ | 8 | 315° | 33 | 41 | 49 |
| 157.5° | $\frac{17+24}{2}$ | 16 | 15 | 326.25° | $\frac{33+26}{2}$ | $\frac{41+34}{2}$ | 42 |
| 168.75° | 24 | $\frac{16+23}{2}$ | $\frac{15+22}{2}$ | 337.5° | $\frac{33+26}{2}$ | 34 | 35 |
| | | | | 348.75° | 26 | $\frac{34+27}{2}$ | $\frac{35+28}{2}$ |

$$C = \sum_{i=1}^{n} \frac{|\cos(\theta_R - \theta_i)|}{n} \quad (1)$$

In equation 1, $\theta_R$ represents the reference direction in which the correlation is being measured; $\theta_i$ corresponds to the contours used for averaging in the $\theta_R$ direction, $n$ is an integer which in the present embodiment is equal to 3, since there are 3 bytes between the center and the edge of the 7 × 7 byte window. A correlation histogram is computed for each of the 1024 elements stored in the ridge contour RAM corresponding to each occupying the center element position of the 7 × 7 byte window.

Figures 14A, 14B:
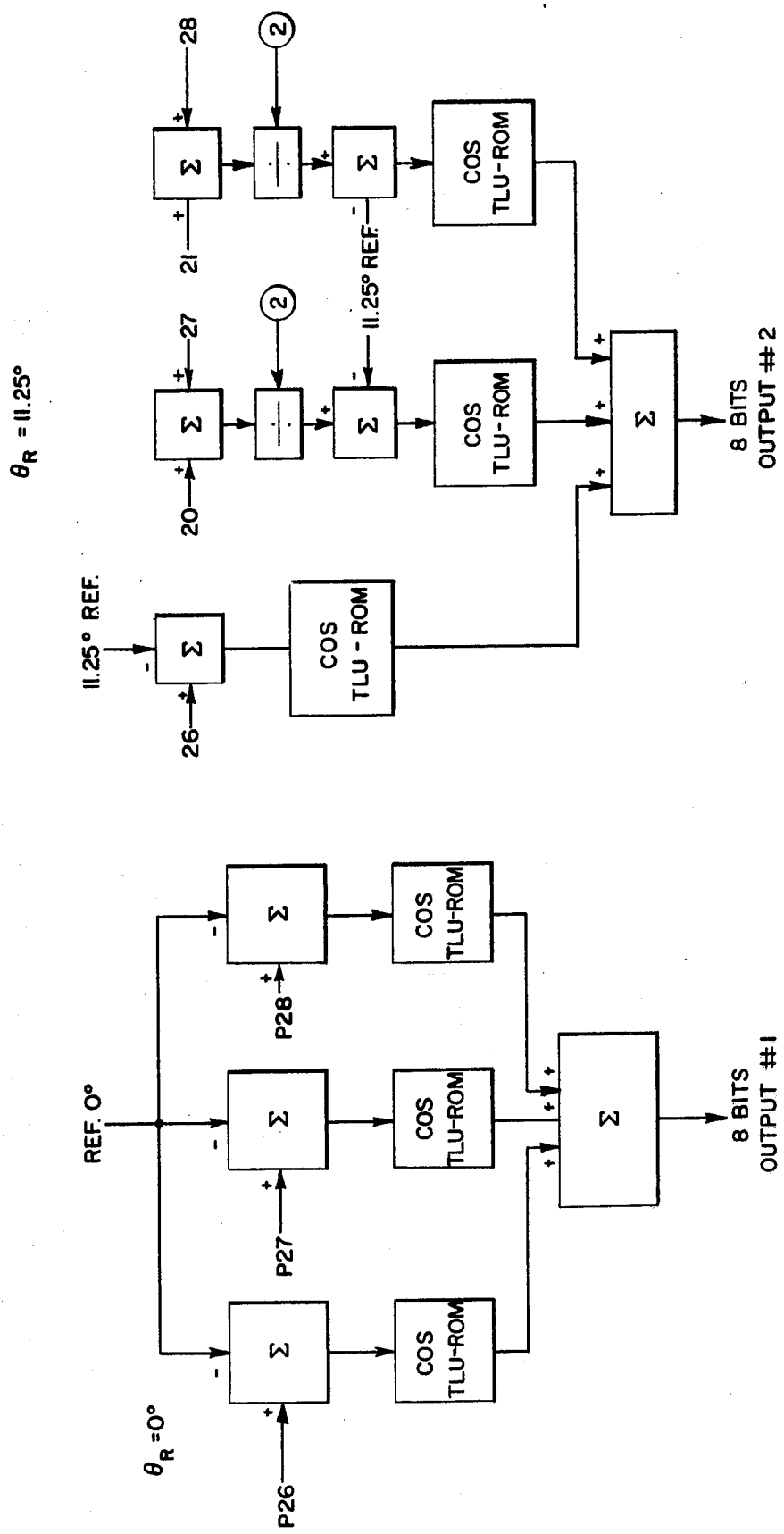
FIGS. 14A 14B, 14C, 14D and 14E, hereinafter referred to as FIG. 14, presents a detailed block diagram of circuitry used to derive the correlation of the reference angle from the 7 × 7 buffer shown in FIG. 13.
Figures 14C, 14D, 14E:
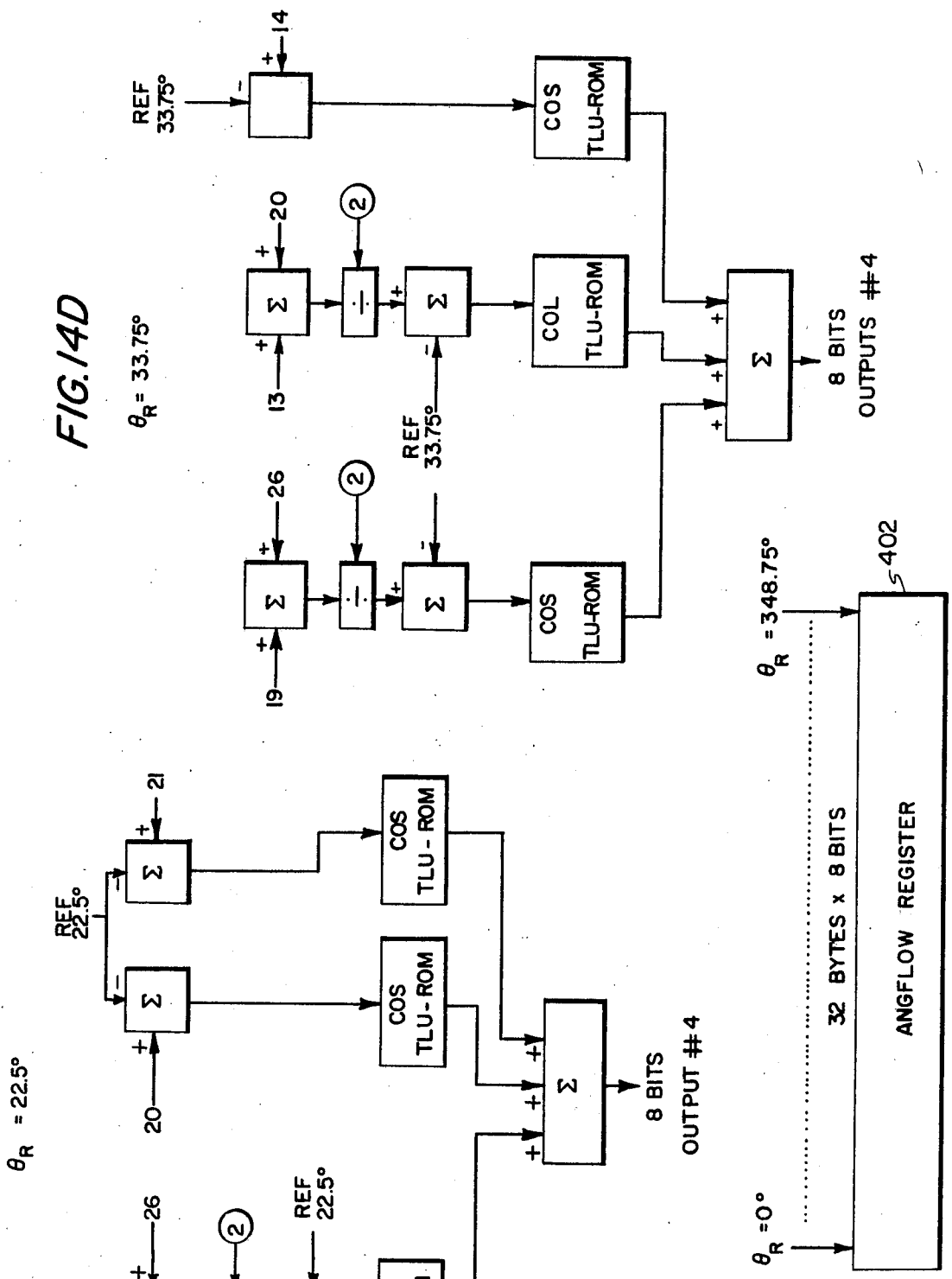

In FIG. 14, four of the 32 angle processing circuits are shown which function to calculate the cosine of the angular difference between the current reference angle and the average contour angle in the reference direction. In the case of $\theta_R = 0°$, each of the values stored in cells 26, 27 and 28 of the 7 × 7 buffer (FIG. 13) is Employing the 32 circuits as exemplified in FIG. 14, and employing the cell values as indicated in Table II, the correlation calculation is automatically derived according to equation 1. Accordingly, a 32 byte correlation histogram, corresponding to the 32 angles of reference, is produced for each center element of the 7 × 7 window. Outputs No. 1, 2, 3, 4 . . . 32 are output from the circuits exemplified in FIG. 14, in parallel to the ANGFLOW register 402, shown in FIGS. 14 and 16.

FIG. 15 shows representations of the 7 × 7 byte window at non-singularity, tri-radii and core points of the ridge contour data. FIG. 15 also indicates the correlation histogram showing two peaks in the correlation values at particular reference angles, which would be present in the ANGFLOW register 402, for a detected non-singularity; three peaks for a detected tri-radii point; and one peak for a detected core point. The 7 × 7 byte window is scanned one byte by one byte over the 32 × 32 matrix of the ridge contour data. At each center position of the 7 × 7 byte window, a histogram of the correlation is derived, as described above, according to the 32 radial lines corresponding to the 32 values of $\theta_R$. Therefore, up to 1024 complete sets (histograms) of correlation data is generated by the scan of the 7 × 7 window over the 32 × 32 ridge contour array.

Figure 16A:
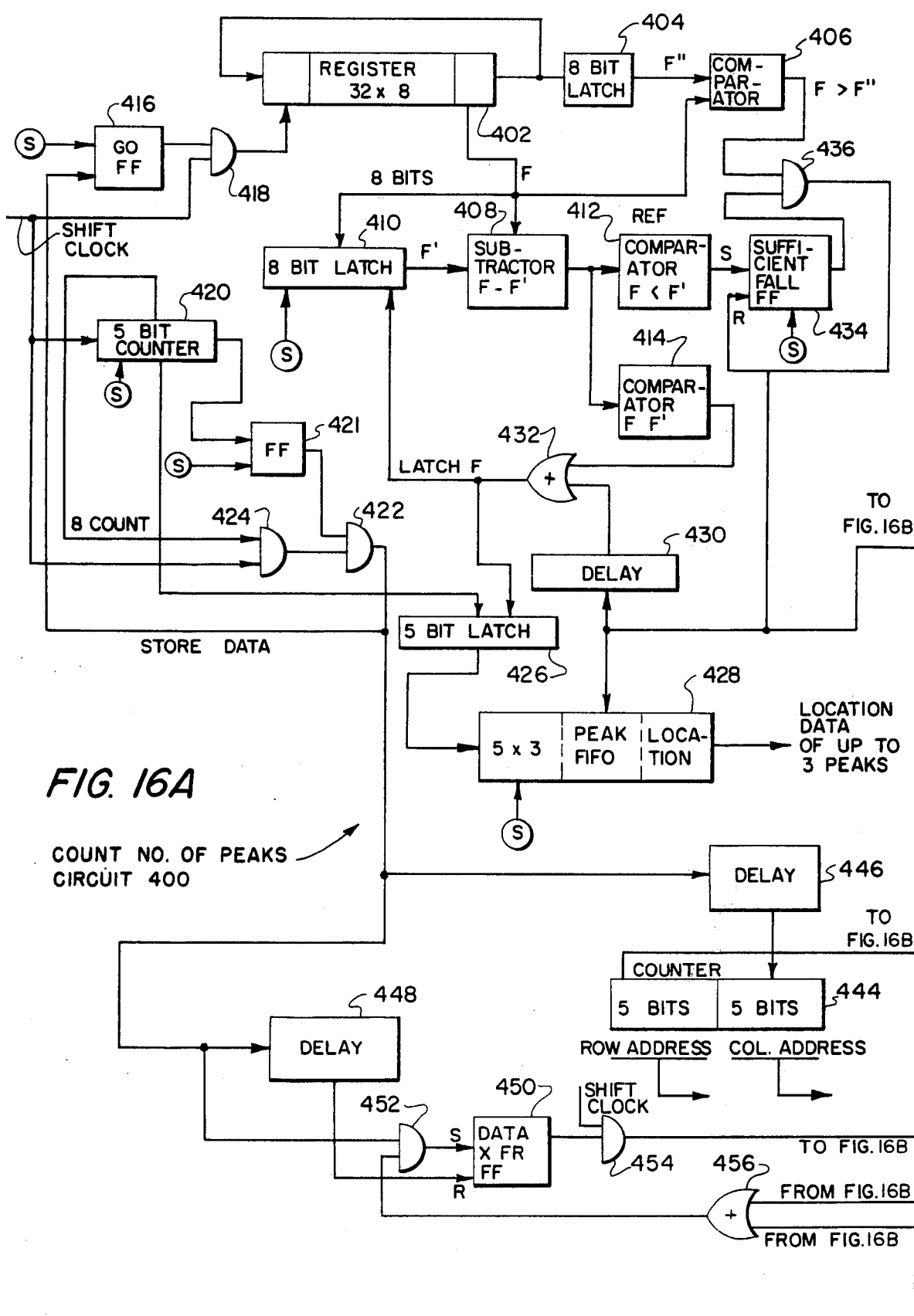

A Count No. of Peaks Circuit 400 is shown in FIG. 16. In this circuit, the number of peaks in each set of correlation data resulting from the previous scan of the 7 × 7 byte window is determined for each of the 32 × 32 (1024) positions. The corresponding number of peaks is then stored in a number of peaks array $RAM_{440}$ having a 32 × 32 dimension with 2 bits/position. Angle values corresponding to the peaks detected at each location are stored in a location peaks array RAM having a dimension of 3 × 32 × 32 bytes with 5 bits per byte.

The Count No. of Peaks Circuit 400 requires the recognition of the occurrence of a peak. The occurrence of a peak is determined by comparison of successive ones of the 32 values stored in the ANGFLOW register 402.

In order to determine the occurrence of a peak, the count No. peak circuit 400 stores the highest ordered value and then examines the decreasing values of successive measurements until such time as the values begin increasing. At that point, the circuit determines if the prior highest ordered value was a peak and it is suitably stored with a corresponding identification of its location. The criterion for determining the peak requires that the fall-off value from the peak value exceed some predetermined threshold and that the values again start to increase.

The 32 stage ANGFLOW shift register 402 has a recirculation loop to permit shifting 40 times, thereby to achieve a wrap-around analysis of the data, sufficient to fully analyze the increasing or decreasing trends of the 32 values.

An initializing pulse S initiates a GO flip-flop 416 and enables AND gate 418 to gate through 40 shift clock pulses to the shift register 402. The F output is a current value 8 bits in length which is fed to an 8 bit latch 410 and a subtractor 408. The 8 bit latch is either at an initialized value or a prior value which has been latched. The value stored in the 8 bit latch 410 is designated as F' and is subtracted from the current value F in the subtractor 408. A comparator 414 produces a signal whenever the current value F is greater than the value F' stored in the 9 bit latch 410. The output of the comparator 414 is fed through an OR gate 432 and functions as a latching signal to command the 8 bit latch 410 to store the current value F whenever it is greater than the prior value F' stored in the latch 410. This provides a trackup function wherein the highest value of F is stored and compared with the next value in sequence. It should also be pointed out at this point that the F values are 8 bits in length and therefore range in amplitude from 0 to 255 units.

A comparator 412 for determining if F is less than F' has a reference threshold value of 64 (REF) which represents ¼ of the maximum amplitude range. Therefore, if the difference between the current value F and the value F' is greater than 64, the comparator 412 generates an output to a sufficient-fall flip-flop 434 to indicate that F' stored in latch 410 is a "peak" value.

An 8 bit latch 404 stores each current value as it is presented at the output stage of the shift register 402. The value output from the 8 bit latch 404 is designated as F" in correspondence to the value immediately preceding the current value F. A comparator 406 compares the current value F and the immediately preceding value F" and produces an output whenever F is greater than F". The output from the comparator 406 is fed to one input of AND gate 436 and the output from the sufficient-fall flip-flop 434 is fed to a second input of the AND gate 436. When the current value F is greater than the immediately preceding value F", it indicates that the sequential values are starting to increase. If the sufficient-fall flip-flop 434 has produced an output, indicating that a peak has been passed, the output of the comparator 406 will indicate that the values which were descending subsequent to the detection of the peak, have reached their lowest point and are now starting to increase again. The combination of the output of the comparator 406 and the output of the sufficient-fall flip-flop 434 produce an output from the AND gate 436 which causes the sufficient-fall flip-flop to be reset and latches the FIFO 428 to store the reference angle location of the peak having a value F'.

The location of the value of F' is stored in the 5 bit latch 426. As each shift clock is received by the shift register 402, a 5 bit counter 420 counts the shift clock pulses. The output of the 5 bit counter 420 is fed to the 5 bit latch 426. When the latch signal produced by the OR gate 432 is fed to the 8 bit latch 410 to latch in the F' value, that latch signal is also fed to the 5 bit latch 426. Therefore, the location of each F' value stored in the 8 bit latch 410 is stored in the 5 bit latch 426. The FIFO 428 has a capacity of storing three peak locations 5 bits in length (designating locations of 0 to 31).

The output from the AND gate 436 is also fed through a 1 bit delay circuit 430 and the OR gate 432 to latch the new F value into the 8 bit latch 410 to become the new F' value. That function erases the previous F' value which was determined to be a peak and substitutes a new value to which subsequent F values will be compared to determine any subsequent peak.

In order to perform an adequate identification of peaks, it is necessary to wrap-around process the information in the shift register 402. Therefore, the output from the shift register 402 is fed back to the input and the first 8 values are again processed, following the 32nd value. In all, 40 values are processed to determine the number of peaks in the register 402 and their corresponding locations. In order to achieve the wrap-around function, the flip-flop 421 receives an output from the 5 bit counter 420, which is set when the 5 bit counter 420 counts through 31 and thus enters the second cycle of counting. The flip-flop 421 supplies an output to an AND gate 422 and receives a second signal from AND gate 424 which is enabled by the 8 count ($2^3$) output of the five bit counter 420. Therefore, when a count of 8 clock pulses is obtained, the AND gate 422 is enabled by the flip-flop 421 sending a "Store Data" signal which resets the GO flip-flop 416. This, of course, terminates the continued recirculation of the shift register 402 and concludes the wrap-around processing of the 32 values in the shift register 402 to determine the number of peaks and their reference angle locations.

A 2 bit up-down counter 438 receives the output from the AND gate 436 whenever a peak is detected, counts up by one bit for each detected peak and freezes at a maximum of 3. The output from the counter 438 supplies the number of peaks data to a 32 × 32 RAM 440, which is called the "No. of Peaks Array". Each storage position of the No. of Peaks Array 440 can store 2 bits to binarily store a value of 0-3.

A 3 × 32 × 32 RAM 442 labeled a "Location Peaks Array" is capable of storing 5 bits/position and stores in the corresponding position the 5 bit reference angle location identification of the from 1 to 3 peaks stored in the No. of Peaks Array 440. The Store Data signal from the AND gate 422 which is used to reset the GO flip-flop 416, also serves to command storage in the RAMs 440 and 442. The counter 444 serves to monitor the successive 32 × 32 positions of the 7 × 7 byte scanning window to thereby identify each position of that window and supply the corresponding row and column addresses to the RAMs 440 and 442. The output from the two-bit up-down counter 438 is output to an OR gate 456 which provides a "true" signal when the number of peaks is more than 0. The output from the OR gate 456 enables the AND gate 452 to set the data transfer flip-flop 450 when the Store Data signal from the AND gate 422 is produced. When the data transfer flip-flop 450 is set, an AND gate 454 is enabled thereby and gates through shift clock pulses for storing the angle data at the address for the given column and row of the 7 × 7 byte window position, in accordance with whatever number of peaks have been detected. That information as currently stored in peak location FIFO 428, in each of its three sections, is written into the appropriate position of the location peaks array 442.

A delay time thereafter, i.e., after the Store Data signal, a shift clock resets the data transfer flip-flop 450 and also increments the 10 bit address counter 444 to correspond to the next position of the 7 × 7 byte window for determining the number of peaks at that next position. In sequence, each of the 32 × 32 positions of the 7 × 7 byte window is processed to determine the number of peaks present at each location and the reference angle location of each of the peaks with respect to the 7 × 7 byte window.

The overflow bit from the counter 444 is fed to and sets a masking-in process flip-flop 458. The set flip-flop 458 enables AND gate 460 and gates through shift clock pulses designated $S_M$ (masking shift pulses). The masking circuit is shown in detail in FIG. 17.

The masking circuit shown in FIG. 17, performs both a background editing function by inserting a 0 in each position of the No. of peaks array that has been determined as the "background" of the fingerprint pattern and output from the 1-dimensional local threshold circuit shown in FIG. 5, and a non-singularity point removal function.

The fingerprint background data from the voltage discriminator 58 in FIG. 5, is input to a 32 position multiplexer 501 as shown in FIG. 17. An 8 bit counter 503 outputs its five most significant bits as an address to the 32 position multiplexer 501. Therefore, each position of the 32 position multiplexer, corresponds to 8 bits of the 256 bits in a single line scan of the fingerprint pattern. Therefore, if a 1 is output from voltage discriminator 58, which corresponds to a single bit of background data, the multiplexer 501 will correspondingly set a 1 in one of 32 positions in a 32 × 1 shift register 507. For each 8 bits of scan on the fingerprint pattern, the 32 position multiplexer 501 correspondingly shifts the fingerprint background data into different stages of the shift register 507. When the 8 bit counter 503 produces a carry, a 3 bit counter 505 counts up by 1 bit. When the 8 bit counter 503 produces 8 carry signals, the 3 bit counter 505 produces a single carry signal. The carry output signal from the 3 bit counter 505 corresponds to 8 scanned rows of the fingerprint pattern. The carry output signal from counter 505 then causes storage of the values from the shift register 507, which is a parallel-in, parallel-out register. The aforesaid combination of multiplexer 501, shift register 507, 8 bit counter 503 and 3 bit counter 505 effectively reduces a 256 × 256 scan into a 32 × 32 array of information. In the present case, when 8 rows of the fingerprint pattern have been scanned, each of the 32 positions in the shift register 507 then correspond to 32 (8 × 8) windows. If a 1 appears in any 8 × 8 window, that corresponding bit location in the 32 × 32 RAM 504 is occupied by 1.

At the end of each eight rows of scan, the 3 bit counter 505 through its carry output signal causes parallel storage of the 1's or 0's from the 32 position shift register 507 to be read onto the corresponding one of the 32 rows of the 32 × 32 fingerprint pattern location array (RAM) 504.

Since 1's are stored in those positions of the fingerprint pattern location array 504 where the fingerprint pattern is not located (background area) and 0's are located in those positions where the fingerprint pattern is located, simultaneous addressing of the No. of peaks array 440, shown in FIG. 16, and the fingerprint pattern location array 504, is effective to eliminate any erroneous data which may be stored in the No. of peaks array 440 outside the fingerprint pattern area. This procedure serves to enhance the information stored in the No. of peaks array 440 by masking out peaks which may have been erroneously identified in the background area surrounding the fingerprint pattern.

The circuit performing the above procedure shown in FIG. 17 is also effective to mask out from the fingerprint pattern, all locations which indicate 2 peaks (non-singularities). This function leaves only clusters of peak values in the No. of peaks array which number 1 or 3 peaks within the detected fingerprint area, indicating corresponding detection of cores and tri-radii points.

Referring to FIG. 17, the fingerprint pattern location array 504 (a 32 × 32 RAM) and the No. of peaks array 440 are simultaneously addressed by the 10 bit address counter 502. The data read from the No. of peaks array 440 is analyzed by gate circuit 506 and if a number 2 is detected, an OR gate 508 gates through a 0 back to the No. of peaks array position determined by the address from the 10 bit counter 502. This eliminates all non-singularity detections which are stored in the No. of peaks array 440.

The fingerprint pattern location array 504 has 1's stored therein where the bright background surrounding the fingerprint pattern is located and 0's where the fingerprint pattern is located. The 1's read out from the fingerprint pattern location array 504 from their corresponding addressed positions, also cause a 0 to be gated through the OR gate 508 to be read into the No. of peaks array 440 at the corresponding address location. Typically, in a 32 × 32 array wherein one core point and one tri-radii point are detected, the resulting contents of the No. of peaks array 440 will appear as clusters, as are shown in FIG. 18.

Figure 18:
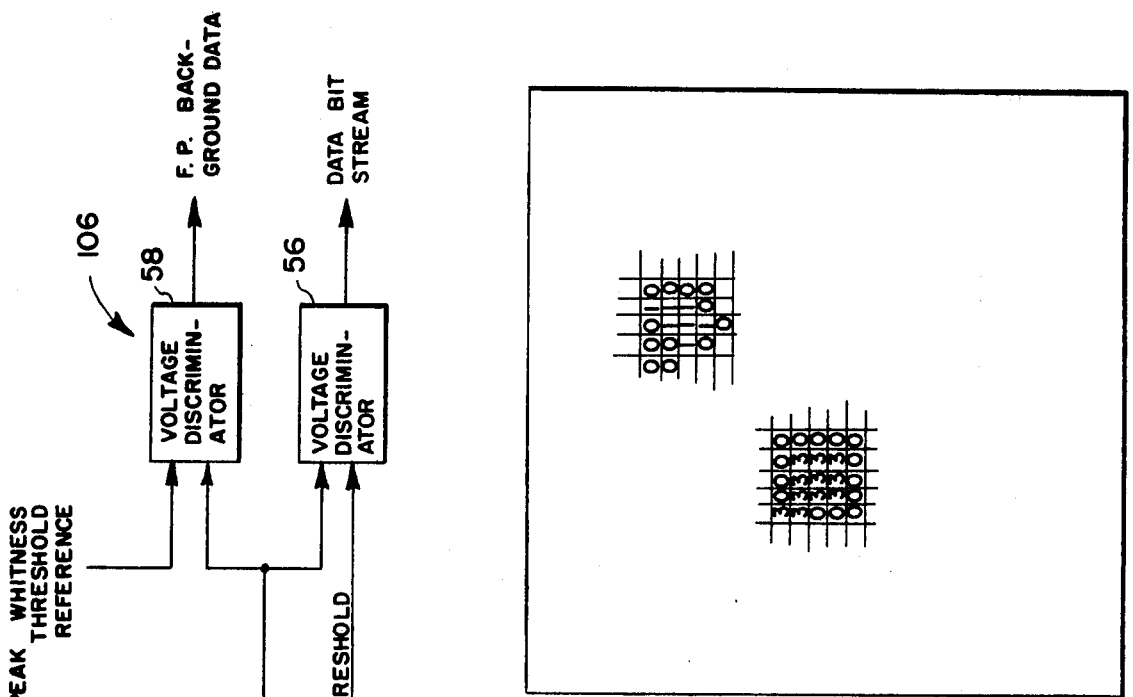
FIG. 18 is a conceptual view of a No. of peaks array after masking by the circuitry shown in FIG. 17.

In FIG. 18, results of the masking function are shown wherein those areas which before masking may have indicated 2 peaks representing the detection of non-singularities, or background area, now contain 0's. Those positions of the array which indicated 1 or 3 peaks remain. Therefore, in the example shown in FIG. 18, a single tri-radii cluster of 3's and a single core point cluster of 1's have been detected.

Following the masking step, the clusters must be "thinned" in order to eliminate any spurious 3's or 1's which may erroneously appear in the No. of peaks array 440 outside of the clusters, and also to reduce the size of the clusters to a single coordinate position in the array.

Cluster thinning can be visualized by scanning along the 32 × 32 No. of peaks array 440 with three position sampling windows depicted in FIG. 19. The circuit for performing the cluster thinning is shown in FIG. 20 and is referred to as a three cell processor. The three cells for the three cell processor comprise a central cell (marked with an X in FIG. 19), an adjacent cell having a row plus one address and an adjacent cell having a column plus one address. As the three cells are scanned (left to right and top to bottom), the values in the three cells are compared. As long as either of the two cells, which are adjacent to the central cell, has the same value as the central cell, the central cell retains its value at that position. If not, the position corresponding to the location of the central cell is set to 0 (i.e., if both the adjacent cells are different than the central cell, the central cell value is set to 0.) This results in an array in which the clusters of 1's and 3's are enhanced and eliminates any erroneous values of 1 or 3 which are not in a cluster. A 12 bit counter 518 having two 5 bit sections with a 2 bit overflow stage provides for 3 cycles of the 12 bit counter 518. When the third cycle is completed, an AND gate 520 receiving the 2 bit counter output (binary 3) generates an END pulse which resets a thinning-in process flip-flop 510. The thinning-in process flip-flop 510 was originally set by the overflow bit from the 10 bit counter 502 at the termination of the masking function.

In order to achieve the desired results in the 3 cell processor, the output from the No. of peaks array 440 is supplied to a "number of peaks subcycle" multiplexer 602, shown in FIG. 20. The output from the No. of peaks array 440 is the actual value of the number of peaks at the current position of the central cell of the 3 cell processor. That value is supplied from the multiplexer 602 to the "row, column buffer register" 604. If the value from the multiplexer 602 is 0, the gate 606 produces a signal to an OR gate 608 which shifts the clock control flip-flop 614, shown in FIG. 17. The clock control flip-flop 614, when set, enables an AND gate 616 to pass a shift clock pulse through AND gate 512 which receives the output from the thinning-in-process flip-flop 510. The AND gate 512 then enables the AND gate 514 which receives the further input condition (inverted) from a subcycle flip-flop 618 (to be discussed later). The output from the AND gate 514 is gated through an OR gate 516 and advances the 12 bit counter 518 which serves to address the No. of peaks array 440 and shift the central cell to the next position of the No. of peaks array 440. Thus, a detection of a 0 peak value causes immediate advancement of the 3 cell processor to the next position of the No. of peaks array.

Referring again to FIG. 20, if the output from the row, column buffer register 604 is either a 1 or a 3 value, corresponding AND gates 610 or 612 gate signals to OR gate 616 which result in a "set" input to a subcycle flip-flop 618 to initiate a subcycle mode. The subcycle flip-flop 618 output enables an AND gate 620 which gates a shift clock pulse $S_T$ which is derived at the output of AND gate 512, as shown in FIG. 16.

The shift clock $S_T$ is gated through AND gate 620 and sets the 2 bit subcycle counter 622 to a count of 1. (Although a two bit counter is shown, it is gated so that is resets at a count of 2. A 1 bit counter could also be used.) The 2 count is gated through AND gate 624 to reset the subcycle counter 622 and also reset the subcycle flip-flop 618. Simultaneously, the output of 624 is applied to the "address" and subcycle address control multiplexer 626. The multiplexer 626, then in timed sequence, develops two addresses for the two other comparison cells of the three cell processor. The first address is derived from the row address value of the 5 bits of the 12 bit counter 518, shown in FIG. 17 and the column address value from the +1 column adder 532. The second address is derived from the 5 bit column address of the 10 bit counter 518 and the row address from the +1 row adder 530.

The time multiplexing of the readout of the 3 adjacent cells of the No. of peaks array is then performed by the No. of peaks subcycle multiplexer 602. That multiplexer, in timed sequence, receives those values from the addressed positions of the two adjacent cells and the No. of peaks array 440 and places them in corresponding buffers 630 and 632. At that point, the values of the central cell and the two adjacent cells of the 3 cell processor are in corresponding ones of the three output buffers 604, 630 and 632. The logic network at the output of the buffers compares for the "1" values of the central cell (stored in buffer 604) as to whether either of the values stored in buffers 630 or 632 is a corresponding "1" or "3" respectively. If a 3' is detected by either or both of the row column buffers 630 or 632, signals are gated though respective AND gates 634 or 638, and are gated through an OR gate 632. If neither of the values in the row, column buffer 630 or 632 are 3 a true signal is generated at the output of the inverter 646 and applied to the AND gate 650. The second input to the AND gate 650 serves to compare the value from the row, column buffer 604. If neither of the adjacent cells contain a value of 3 and the value in the central cell is 3, the AND gate 650 gates a signal to OR gate 654.

Identical comparison of the 1 value in the adjacent cells is made by AND gates 636, 640 and 652 in conjunction with OR gates 644 and inverter 648.

If a true adjacent signal is output from the inverter 646, indicating that neither of the adjacent cells contains a 3 value, the AND gate 650 is enabled. Likewise, the AND gate 652 is enabled if neither of the adjacent cells contains a 1 value. Either of these outputs from the AND gates 650 and 652 enables the OR gate 654 which enables AND gate 654 to cause a read/write flip-flop 666 to write a 0 into the corresponding central cell position in the No. of peaks array 440. The read/write flip-flop 666 shown as a normally "read" flip-flop, is toggled off by the AND gate 664, into a reset condition to produce a true output for the "write" function. The AND gate 668 then gates through a shift clock $S_T$ to cause writing of a 0 into the No. of peaks array 440 at the central cell position corresponding to that position addressed by the 12 bit counter 518.

The output from the OR gate 654 is inverted by the inverter 656 to enable an AND gate 658 to clock through a shift clock pulse $S_T$ to an OR gate 660. The OR gate 660 also is connected to receive the output from the AND gate 668. Either input will cause the OR gate 660 to provide a reset signal to the subcycle complete flip-flop 662 and supply a signal to the OR gate 608. The effect of the output of the OR gate 660 is to cause the clock control flip-flop 614 to advance the 12 bit counter 518 to address the next successive cell. The above process is repeated three times over the 32 × 32 matrix of the No. of peaks array 440. It has been found that three repeated processes are effective for enhancing the number and sizes of peak clusters normally encountered in fingerprint patterns by thinning the clusters and eliminating spurious 1's and 3's which may appear outside the clusters, due to noise.

Upon the masked array being thinned by the 3 cell processor, the compact clusters of 3's and/or 1's present in the No. of peaks array 440 are scanned to select out, of each cluster, the most representative or central cell position for the respective 3's and/or 1's clusters.

Figure 21A:
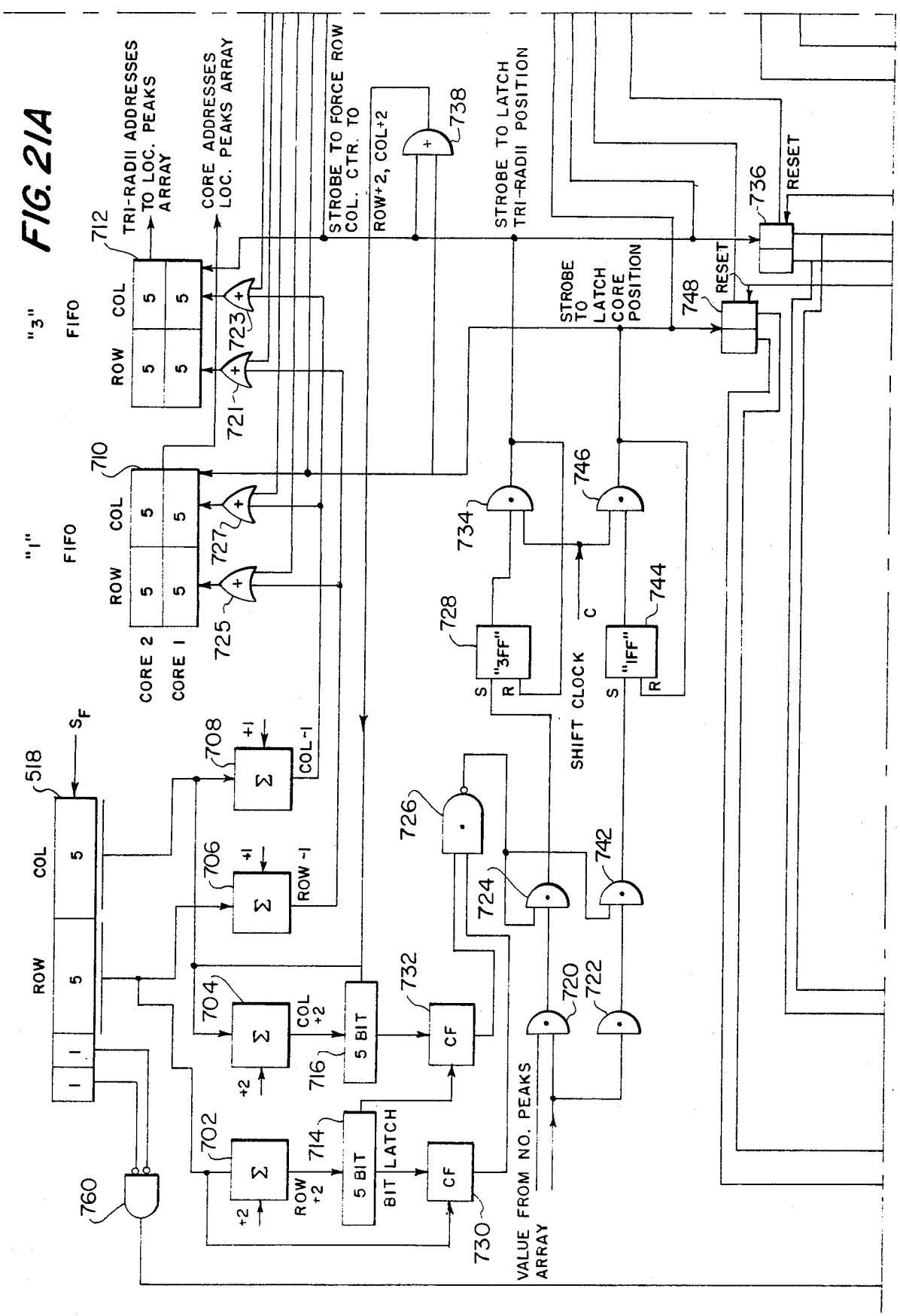
Figure 21C:
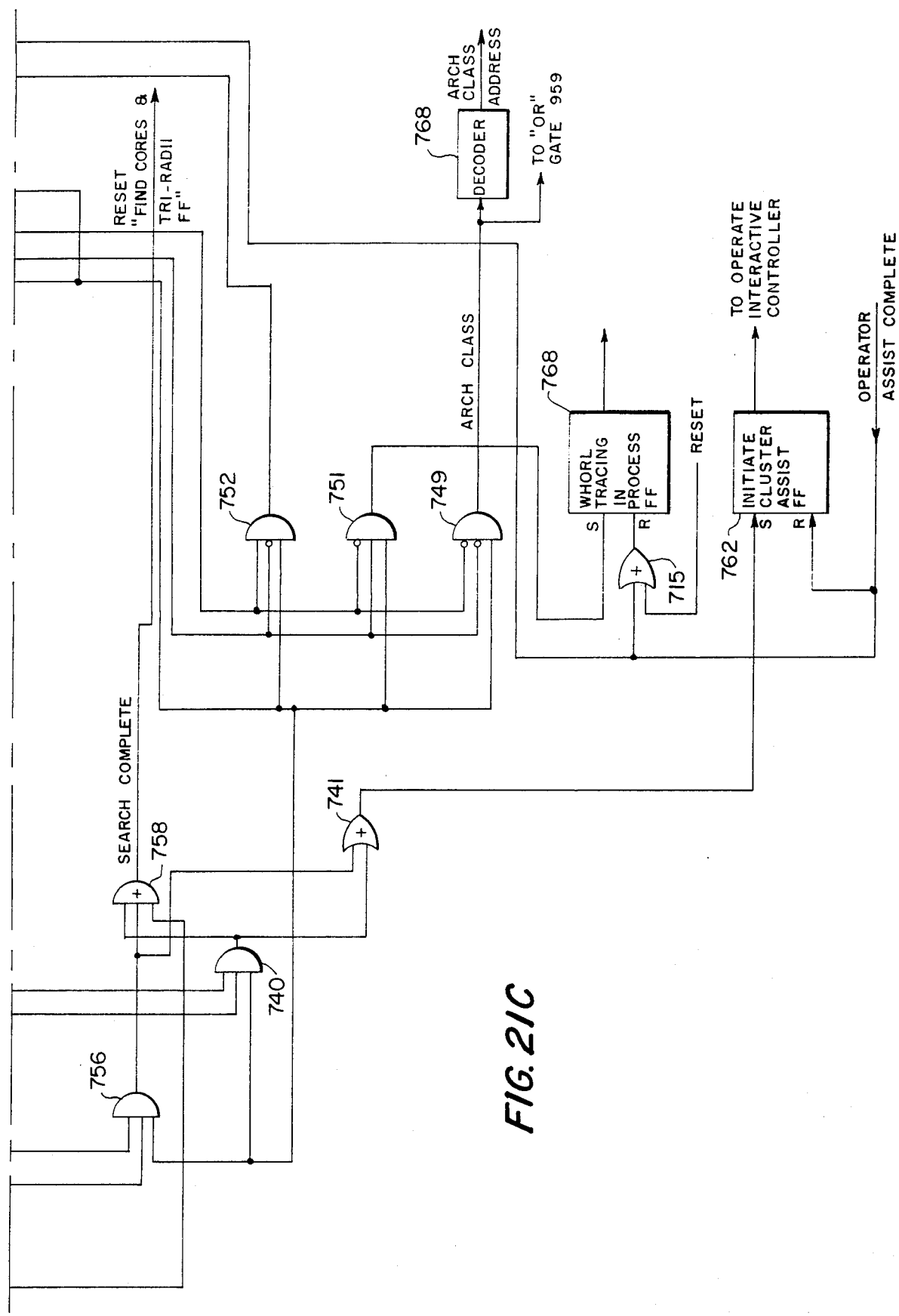

Referring to FIGS. 17 and 21, when the thinning-in-process flip-flop 510 is reset, a "find cores/tri-radii-in-process" flip-flop 540 is set and enables AND gate 542 to gate shift clock pulses and generate "find" shift clock pulses $S_F$. The output of AND gate 542 enables OR gate 516 to gate through clocking pulses to the 12 bit counter 518.

As is shown in FIG. 21, the output from the 12 bit counter 518 supplies 5 bit addresses to a +1 column adder 708, a +2 column adder 704, a +1 row adder 706 and a +2 row adder 702. The +1 row and +1 column addresses from the +1 row and +1 column adders 706 and 708 are supplied as addresses to the respective row and column sections of both "core" and "tri-radii" FIFOs 710 and 712. The 5 bit address from the +2 row and +2 column adders 702 and 704 are fed to 5 bit latches 714 and 716 respectively.

The circuitry shown in FIG. 21 searches over the thinned clusters stored in the No. of peaks array 440 and the remaining 3's and/or 1's clusters will each typically be within a separate 3 × 3 cell array. The first detection of a 3 or 1 during a scan of the No. of peaks array 440 is recognized by the circuitry as the upper left cell of a cluster of corresponding 3's or 1's. The circuitry then assigns the next lower row (row +1) and the next adjacent column (column +1) address location as the center of the cluster. Such a determination of the center of a cluster causes a latching signal to be produced to store the row +1 and column +1 addresses in the corresponding FIFO 710 or 712, depending upon whether the 1 or 3 value is detected in the scanned cell.

To achieve the aforesaid function, the No. of peaks array 440 is scanned one time by sequentially addressing single cell locations cell by cell according to the address produced by the 12 bit counter 518. The stored values are read out from the No. of peaks array 440 into decoding gates 720 and 722. If a 3 is detected, the gate 720 produces an enabling signal to AND gate 724. The current row and column addresses are respectively compared in comparators 730 and 732 with values stored in the 5 bit latches 714 and 716. If the present row or column address value exceeds the corresponding latched address, the NAND gate 726 will produce an enabling signal to the AND gate 724. The output from the AND gate 724 sets the 3 find flip-flop 728, which enables AND gate 734 to gate through a single shift clock pulse to strobe the FIFO 712 and latch the row and column addresses +1, from the 5 bit latches 714 and 716 through corresponding OR gates 721 and 723, in the FIFO 712. The single gated clock pulse from AND gate 734 resets the 3 find flip-flop 728. The output from the AND gate 734 also is fed to a 2-bit counter 736 which counts the number of tri-radii found during this process. A count of 2 in the 2-bit counter 736 causes a disabling signal to be gated through NAND gate 740 to disable the AND gate 724.

In addition to the other effects of the output of the AND gate 734, the output therefrom also enables OR gate 738 to latch the 5 bit row and column latches 714 and 716. The effect of the row and column addresses +2 being latched in the 5 bit latches 714 and 716, is to prevent the same cluster from being detected and processed during the remainder of scanning of the number of peaks array 440. Therefore, for each detected cell of a particular cluster, a 3 × 3 lock-out area is provided by the above circuitry to prevent multiple finding of the same cluster.

If, during the scan of the number of peaks array 440, a 1 (core) cell is found, the AND gate 722 produces an enabling signal to AND gate 742. If the current address for the found 1 exceeds either of the corresponding values stored in the latches 714 and 716, the 1 find flip-flop 744 is set and thereby enables the AND gate 746 to gate through a single clock pulse and latch the row +1 and column +1 addresses from the adders 706 and 708 to the corresponding address location of the FIFO 710. It should be recognized at this point, that the 1 find circuit operates identical to the 3 find circuit.

In this embodiment, a plurality of cores and tri-radii may be found to be present in the No. of peaks array 440. However, if more than two cores or tri-radii are found, then proper classification is in doubt and operator assist is required. Therefore, up to two cores and tri-radii may be found and stored in the corresponding FIFO's 710 and 712 while the count number from the corresponding 2 bit counters 748 and 736 produce count numbers corresponding to the found cores and tri-radii.

It is important to note, that the aforesaid circuitry is effective for detecting more than one cluster that may occur in the same row or column. Since it has been established in this embodiment that a 3 × 3 cluster will only include one located tri-radii point, the aforesaid circuitry has effectively blocked out a 3 × 3 cell portion of the scan after the upper left cell of a particular cluster has been detected and the location of the cluster has been assigned to the center cell of the 3 × 3 cell array.

A count of 0 in the 2-bit counter 736 enables an "arch class" AND gate 749, a count of 1 enables a "loop" AND gate 752, a count of 2 enables a "whorl" AND gate 751 and a count of 3 enables AND gate 740. As will be described later, when a "search complete signal" is produced by the AND gate 760, it will be gated through one of the AND gates 749, 752, 751 or 740.

A count of 3 in the 2-bit counter 736 indicates that too many tri-radii have been detected and that operator assistance is needed to determine which of the detected tri-radii are valid and which are invalid. Therefore, when a signal is gated through AND gate 740 and OR gate 758, the "initiate cluster assist" flip-flop 762 is set and a signal is sent to the operator interactive controller, indicating that operator assistance is required. Correspondingly, when the 2-bit core counter 748 detects more than two cores, a signal is gated through AND gate 756 and OR gate 758 to set the initiate cluster assist flip-flop 762.

Referring again to FIG. 21, when the 10 bit portion of the 12 bit counter 518 has cycled three times for the thinning operation, as outlined previously, the most significant bits output from the last two stages of the 12 bit counter 518 disable, through inverting inputs, AND gate 760. When the 10 bit portion of the 12 bit counter 518 cycles for the fourth time to achieve the above finding operation of the cores and tri-radii points, the AND gate 760 is enabled and produces a "search complete" signal through OR gate 758. The search complete signal resets the "find cores/tri-radii" flip-flop 540 shown in FIG. 18.

The search complete signal fed to the above described AND gates 749, 752, 751, 740, 756 and 758 has at least one of the following effects. An enabled AND gate 749 will gate an arch class signal to OR gate 959 shown in FIG. 26B, an enabled AND gate 752 will set a loop tracing in process flip-flop 766 through OR gate 764, an enabled AND gate 751 will set a whorl tracing in process flip-flop 768 through OR gate 715, an enabled AND gate 740 will set the initiate cluster assistance flip-flop 762 through OR gate 741, and/or an enabled AND gate 756 will set the initiate cluster assistance flip-flop 762 through OR gate 741.

At this point, it should be recalled that when the number of tri-radii detected in a particular fingerprint pattern equals 1, a loop classification is determined and further processing is required, which entails the tracing of the associated ridge flow lines (see FIG. 10). Similarly, when the number of tri-radii detected equals 2, a whorl classification is determined and further processing is also required, which entails the tracing of associated ridge flow lines.

If the number of tri-radii found is zero and the search complete signal is output from the OR gate 758, the AND gate 749 produces a classification complete signal through OR gate 959 and no tracing is required, since the classification is determined to be an arch. The arch class address is output from the decoder 768 in response to the signal gated through AND gate 749.

For the purposes of continuing the discussion of the operation of the circuit, it is assumed that one tri-radii point has been detected and the loop tracing-in-process flip-flop 766 is set. It should be further understood that if two tri-radii points were detected, the whorl tracing-in-process flip-flop 768 would be set and curve tracing would proceed in a manner substantially identical to that described below, with respect to curve tracings in the loop classification. The set output from the loop tracing-in-process flip-flop 766 sets a latch 772 to enable an AND gate 774 to gate through shift clock pulses for the tracing function which follows. The shift clock pulses output from the AND gate 774 are labeled $S_{TR}$ and are used for reading the location peaks array 442, shown in FIG. 16.

The nomenclature "trace" is adopted since this is the visual concept for the function discussed below.

In order to perform the tracing function, it is necessary to read both the location of peaks array 442, shown in FIG. 16 and the original ridge contour data stored in the 32 × 32 storage positions of the RAM 112, shown in FIG. 2. Accordingly, an AND gate 778 output sets a "read ridge contour" array flip-flop 776 which outputs a command signal to the ridge contour array 112 and a multiplexer 802 when a 2-bit Loc. peaks counter 777 counts three $S_{TR}$ signals.

Figure 22:
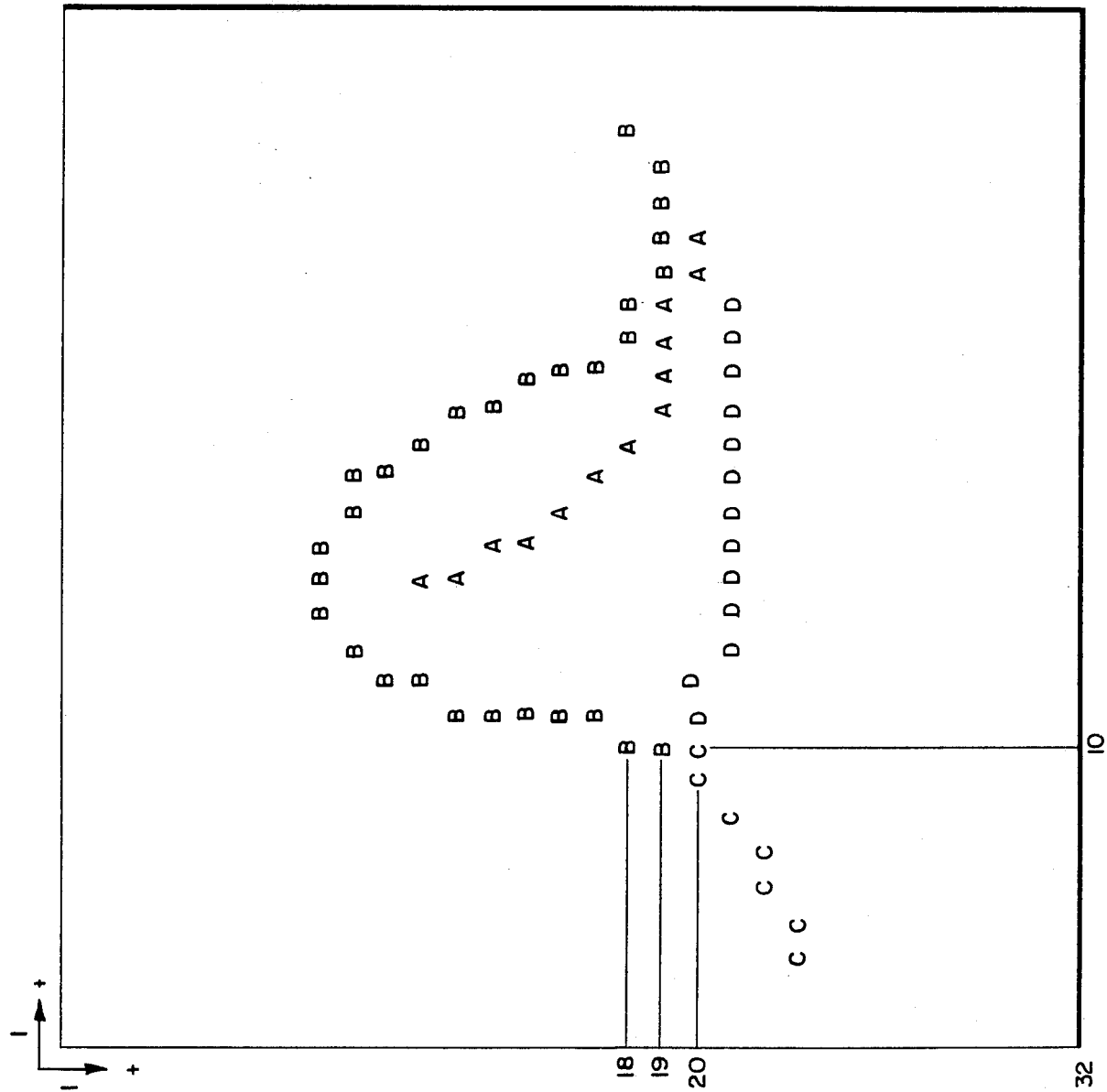
FIG. 22 illustrates an example of a curve tracing of ridge flow contours associated with detected core and tri-radii points.

Reference is now made to FIG. 22, wherein a typical tracing is depicted, which is similar to the tracings shown in FIGS. 9A, 9B and 9C. The tri-radii address from the FIFO 710 causes the location of peaks array 442 to read out three reference angles for that particular tri-radii address. In the example shown in FIG. 22, the tri-radii address would be column 10, row 20. Such an address fed to the location of peaks array 442 would result in three reference angles being read out. The circuit shown in FIG. 23, then performs the B, C and D tracings from that tri-radii point starting in the directions of the reference angles. Subsequent to making the first cell tracing in any one direction of the tri-radii point, the information from the ridge contour array is used to supply additional angle data to continue each trace. Similarly, in the example shown in FIG. 22, the location of the core point is at column address 15, row address 12 and the tracing of the ridge flow line associated with that core point is designated as A. The tracing of A is performed in the same manner as that discussed for any one tracing of the tri-radii ridge flow lines.

The tracing circuit shown in FIG. 23, through its input multiplexer 802, loads, in time sequence, the 5 bits representing each of the three reference angles for the addressed position of the peak location array 442. The multiplexer 802 supplies the three 5 bit reference angle values to corresponding ones of three 5 bit registers 804, 806 and 808 for storage.

Logic circuits 810, 812 and 814 each correlate the 32 possible reference angle positions identified by the 5 bits from its corresponding 5 bit register, into one of eight possible cell locations which are adjacent to the currently addressed cell. The logic circuits 810, 812 and 814 determine the next row and column address incremental values according to the specification chart shown in FIG. 24.

For example, consider the 5 bit output from the register 804 fed into the logic circuit 810. If the 5 bit input to the logic circuit 810 has a value of 9, indicating the reference angle of 90°, the next row address will be incremented by −1 and the next column address will be incremented by 0. This corresponds to the tracing shown in FIG. 22 wherein the first B adjacent the tri-radii point appears at column address 10, row address 19.

The incremental values for the row and column addresses are output from the logic circuit 810 to a FIFO 822. The FIFO 822 has a maximum length of 48, thereby allowing a tracing to extend over 48 cells of a 32 × 32 array of data. FIFO's 832 and 842 receive the outputs from logic circuits 812 and 814, respectively, in order that three curve tracings may be simultaneously produced by the circuitry shown in FIG. 23. The next row and next column addresses are also output from the circuit 810 based upon the current row and column addresses combined with the incremental value determined by the logic circuit 810. The next row and column addresses then serve to address the ridge contour array 112. The logic circuits 812 and 814 respectively also produce next row and column addresses, based upon the incremental values determined in those respective logic circuits, and those addresses are addressed to the ridge contour array 112 via respective monitoring circuits 813 and 815 under the control of the multiplexer 802. The information (5 most significant bits) read out from the addressed location in the ridge contour array 112, in response to the address supplied by the logic circuit 810, is supplied to the 5-bit counter 804 through the multiplexer 802. Depending upon the value stored in the register 804, the logic circuit 810 will determine a new incremental value for the next address.

Again, referring to FIG. 22, if the five most significant bits from the ridge contour array 112 have a value of 8, up to 11, the incremental row will be −1 and the incremental column will be 0, as is shown in the plot of B at column address 10, row address 18.

Whenever the next row or column address from the logic circuit 810 reaches a value of 32, the monitoring circuit 811 indicates that the tracing has reached the border of the ridge contour array 112 and a "stop" signal is generated by the OR gate 820. Correspondingly, monitoring circuits 813 and 815 are provided, which are associated with logic circuits 812 and 814 to produce "stop" signals if either of those particular tracings reach the border of the ridge contour array 112.

According to the above described operation of the circuit shown in FIG. 23, it is possible to trace any curve from the central position in any direction up to a maximum length of 48 incremental positions from the original position, limited by the border of the 32 × 32 ridge contour array 112.

When tracing is completed, the addresses of all of the points defining each of the three paths from the tri-radial point, based on the incremental values and independent of the original position of the tri-radial point, are stored in the three FIFO's 822, 832 and 842. Note that each FIFO 822, 832 and 842 includes a row address and a column address storage position. When the aforesaid FIFO 822 is full, indicating 48 increments of tracing, a "FIFO FULL" signal is generated and enables OR gate 824 to produce a "stop tracing" signal that disables AND gate 826, which is normally gating through clocking pulses $S_{TR}$ in a stop tracing circuit 823. It should be understood, that each of the remaining FIFO's 832 and 842 is independently monitored by corresponding stop circuits 833 and 843 to produce "stop tracing" signals whenever the associated FIFO is full or whenever the tracing exceeds the border of the ridge contour array 112.

A NAND gate 828 responds to all three of the stop tracing signals generated by the circuitry associated with each FIFO 822, 832 and 842 and gates through an "end tracing" signal which resets the read ridge contour array flip-flop 776, resets the loop tracing in process flip-flop 766 (FIG. 22B) and sets the loop classification flip-flop 830. The setting of the loop classification flip-flop 830 enables an AND gate 831 to supply shift clock pulses out to the loop classification circuit shown in FIG. 25.

Figure 25A:
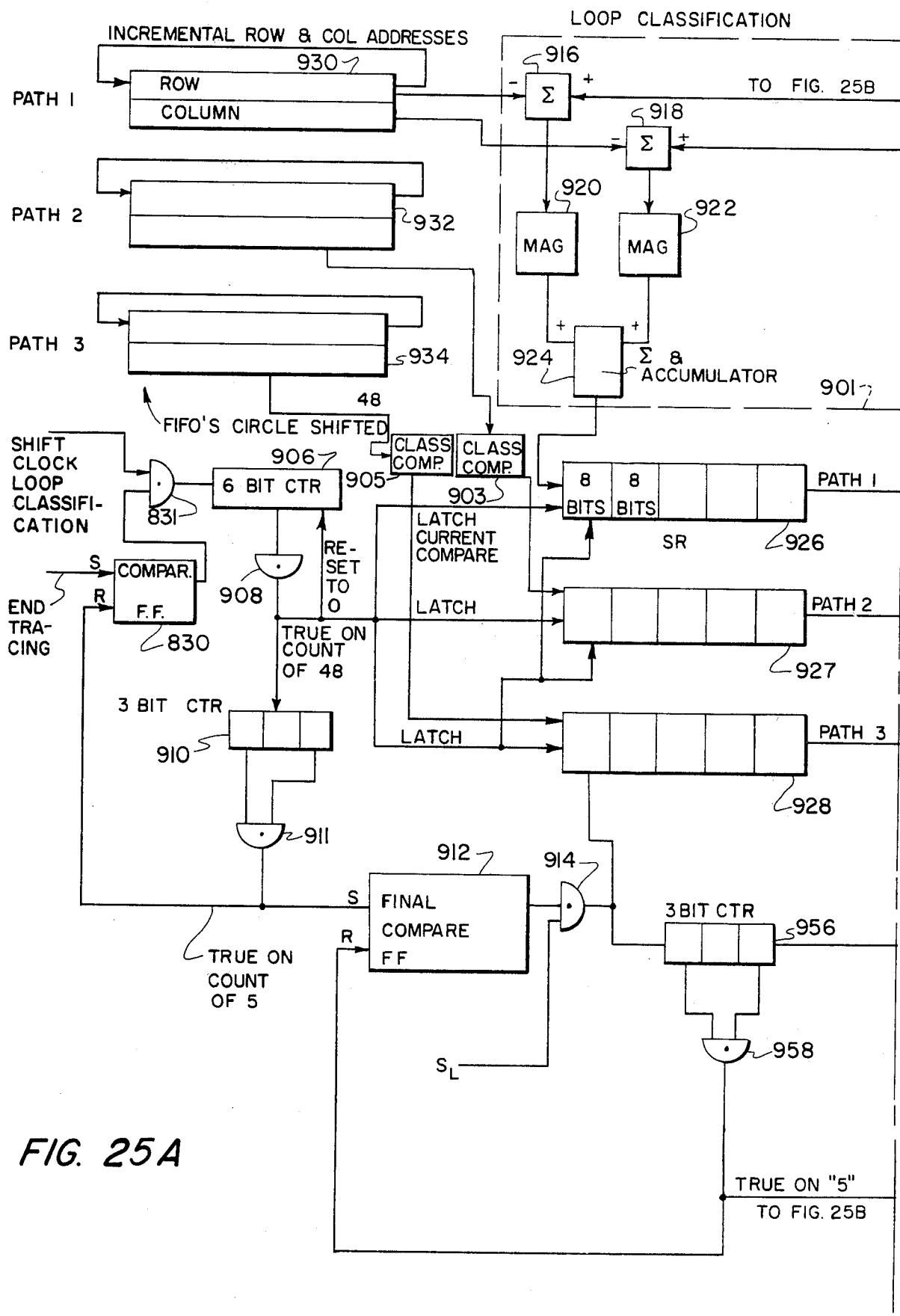

The classification circuit is shown in FIG. 25. For simplification purposes, FIG. 25 shows the final comparison of a single tracing of the three tri-radii lines according to their stored incremental values, with stored reference values to achieve classification. In view of the above it is seen as sufficient to indicate that similar circuitry is employed whereby each of the three tracings are compared with their corresponding stored reference values.

The incremental row and column addresses are developed in FIG. 23 for each tracing and are stored in incremental shift registers 822, 832 and 842. In FIG. 25, those same registers are indicated as registers 930, 932 and 934 with feedback lines. Since the comparison process is identical for the information stored in all three of the registers 930, 932 and 934, the following discussion is directed to the incremental row and column address information stored in the register 930 and processed by the class comparator circuit 901. However, it should be understood that the circuitry performing the comparison (901, 903 and 905) is identical for each of the associated registers 930, 932 and 934.

The register 930 (822) has stored therein the incremental row and column addresses. The register 930 shifts out each incremental value, and that value is recirculated back into the register 930 via a feedback line.

Path reference registers 941, 942, 943, 944 and 945 of the class comparator circuit 901 each store the reference incremental values corresponding to one of the three curve tracings of the five predetermined reference loop classifications.

The incremental row and column address values stored in the register 930 are shifted out, one incremental value at a time, in parallel for the row and column and compared with the contents of path reference register 941. The incremental row values from the register 930 are subtracted from the corresponding incremental values from the register 941 by summing circuit 916. The incremental column values from the register 930 are subtracted from the corresponding incremental values from the register 941 by summing circuit 918. An absolute value of magnitude is determined in circuits 920 and 922 for each of the differences obtained in the summing circuits 916 and 918 and is stored in an accumulator 924 for each of up to 48 compared incremental positions in the registers 930 and 941. After each of the 48 positions are compared and the total magnitude of the differences over the 48 incremental positions is stored in the accumulator 924, an 8 bit word is output from the accumulator 924 and is stored in a five position storage register 926. Each position of the storage register 926 is capable of storing an 8-bit word and corresponds to each of the path reference registers which are to be compared with the incremental information stored in register 930.

The above process is repeated for each of the, for example, 5 path references represented by the contents of the other path reference storage registers 942, 943, 944 and 945. Correspondingly, 8 bit words are developed at the accumulator 924 after each path reference storage register has been compared over its 48 incremental positions.

This function is simultaneously performed for each of the three paths extending from the tri-radii point. The five accumulated values stored in the storage registers 926, 927 and 928 are output from the corresponding registers, in parallel, three at a time, to a summing network 929. The three respective 8 bit words are summed to develop an output P' which is supplied to a comparator 950. The comparator compares the current value P' with a previous summed value P which was set in a "previous sum" register 952. If P' is less than P, the comparator 950 latches P' into the previous sum register 952. The latching signal is also supplied to a 3 bit count 954.

Since a perfect match between the incremental information stored in the register 930 and any one of the path reference registers 941 . . . 945 should produce a minimum accumulated value output from accumulator 924, the initial setting of the previous sum register 952 is all 1's. Therefore, the first comparator output from comparator 950 will be less than the initial set value P and will accordingly be latched into the previous sum register 952. Subsequently, all P' values will be compared to the previous P value. If the first value P is latched in the previous sum register 952, and is a "perfect match" all subsequent comparisons with the path reference registers 942, 943, 944 and 945 will result in P' values exceeding the present P value stored in the previous sum register 952.

The latching signal from the comparator 950 serves to latch a 3 bit counter 954 which receives the count value from a 3 bit counter 956. The 3 bit counter 956 monitors the clock pulses $S_L$ which are gated through an AND gate 914.

The loop classification flip-flop 830 and the associated AND gate 831, shown in both FIGS. 23 and 25, are effective to gate shift clock pulses $S_L$ to a 6 bit counter 906. When the 6 bit counter reaches a count of 48, an AND gate 908 produces an output signal which resets the 6 bit counter 906 to 0 and latches the value from the accumulator 924 into a first position in the storage register 926. The signal produced by the AND gate 908 is correspondingly supplied as a latch signal to registers 927 and 928. The output of the AND gate 908 is also input to a 3 bit counter 910 which counts the number of times the total contents of the register 930 is compared with the total contents of individual path reference registers. In this embodiment, when a count of 5 is reached in the 3 bit counter 910, an AND gate 910 supplies a reset signal to the loop classification flip-flop 830 and sets the final comparison flip-flop 912. The final comparison flip-flop 912 enables AND gate 914 to gate through clocking pulses $S_L$ to perform the final summation function and comparison, yielding the loop classification, as described above. Therefore, the 3 bit counter 956, by counting the clock pulses gated through the AND gate 914, monitors the particular path reference register contents which were compared with the incremental information stored in the register 930 and presents a corresponding count value to the 3 bit counter 954 identifying that path reference register. Therefore, when the 3 bit counter 954 is latched, it identifies the best match (lowest accumulation value) detected at that time. When the 3 bit counter 956 reaches a count of 5, a decoder 958 produces a signal which sets a "loop class ready" flip-flop 960. The output of the loop class ready flip-flop is the "classification complete" signal shown in FIG. 4. A "loop class address" signal is output from the 3 bit counter 954 to the "finger class" section of register 128 (FIG. 2) and is, in this case, a 3 bit signal which identifies one of 5 loop classifications. As discussed with respect to FIG. 2, the main file 116 may be broken down into 16 classification bins. However, the number of classifications could be far more and typically would be.

Although a score value stored in the previous sum register 952 may be lower than the initial value set therein, it may not be sufficiently low to indicate that a classification match has been achieved. Therefore, comparator 951 compares the value P, stored in the previous sum register 952, with a minimum threshold level. The minimum threshold level is preset according to an acceptable classification score value. When the value P exceeds the minimum threshold value, the comparator 951 enables AND gate 953. The signal output from the AND gate 958 is then gated through the AND 953 and sets the low confidence decision flip-flop 955 through OR gate 953. The low confidence decision flip-flop 955 then outputs an "unable to process" signal to the operator interactive controller. The "unable to process" decision is a unique characteristic of this system, since it provides a positive output indication of a determination by the system that the input data is not of sufficient quality to complete a first level of processing — namely, classification — even before the RIV comparison techniques are employed and the main file is searched. The "unable to process" decision may be due to an injured fingerprint pattern, a poor quality latent fingerprint representation, a partial fingerprint, movement of the fingerprint during the scan, or other adverse circumstances. After such a determination that the system is unable to automatically classify the fingerprint with a high degree of confidence, the operator will be instructed to analyze the data used by the classifier to perform classification, as well as the particular classification as determined thereby. If, for instance, the system mistakenly identifies a smudged area of a pattern as a tri-radii point in addition to identifying a real tri-radii point, the system would then mistakenly classify the pattern as a whorl rather than a loop. However, during classification processing, a reference whorl pattern will not be found by the system which will produce a sufficiently low P' sum to be considered as valid classification. In such circumstances, the operator will correct the system data correspondingly read from the smudged area, according to his judgment of what the data should be (e.g., ridge contour angles and minutiae locations). Employing the keyboard/cursor 103, the operator will then erase the erroneous data read by the system at the smudged area and substitute therefore his determination of what the correct data should be. The data corresponding to tri-raddi addresses is input by the operator interactive controller 170 to FIFO 712 via OR gate 721 and 723 respectively. Similarly, the operator's identification of core locations are row and column addressed to FIFO 710 via the operator interactive controller through respective OR gates 725 and 727. Simultaneously, the correct number of tri-radii and core points are input to the 2 bit counters 748 and 736 respectively. When the operator has completed his correction of the classification data, he indicates the completion and a signal is sent via the operator interactive controller 170 to reset the whorl tracing and process flip-flop through OR gate 715 and the loop tracing and process flip-flop 766 through OR gate 714. Following the operator's completion of the data correction, the classifier automatically classifies the fingerprint according to the data as corrected by the operator.

Alternatively, the operator has the option of overriding the automatic classifier portion of the system and determining the classification of the pattern according to the preestablished classification types, and may enter the corresponding classification into the keyboard and instruct the system to compare the pattern with all of the patterns in the main file 116 of that particular classification type.

At that point, the system will automatically search the main file and compare the extracted minutiae according to the aforementioned RIV algorithm technique and produce a list of identities which are determined by the system to have fingerprint patterns most closely matching the latent fingerprint presented for identification.

Of course, it is understood that the five reference registers referred to above would be expanded to ten in order to include the left and right loops and the five sizes associated with each left and right loop classification.

Referring again to FIG. 21, when two tri-radii are detected, the whorl tracing-in-process flip-flop 768 is set through OR gate 715. The whorl tracer circuit 972 shown in FIG. 25 produces incremental line tracings of the ridge contours associated with the two tri-radii. The whorl tracer circuit 972 is implemented with hardware identical to that for producing the loop tracing, shown in FIG. 23. The output of the whorl tracer circuit 972 is then fed to the whorl classification circuit 970 which classifies the whorl pattern with circuitry identical to that shown for the loop classification, shown in FIG. 25. The output of the whorl classification circuit 970 activates a whorl class ready flip-flop 961, causing a classification complete signal to be output through OR gate 959. In addition, the whorl classification circuit 970 outputs a whorl class address which is fed to the finger class portion of the register 128 to supply the classification address of the main file 116.

In a system where the fingerprint image derived from the scanning window is subject to variations in rotation, comparison with the particular set of incremental addresses stored in each of the register 930, 932 and 934 will vary in accordance with the fingerprint pattern angular orientation. Therefore, this system, as exemplified in FIG. 25, is easily modified in order that accurate determination of a classification can be made, invariant to any rotation of the fingerprint pattern. To achieve such a modification, additional path reference registers can be added to those shown in FIG. 25 wherein each path reference register stores incremental addresses conforming to the reference classification rotated by a predetermined amount.

Alternatively to supplying a number of 48 cell path reference registers to reproduce the properly encoded incremental data for angularly offset patterns, it is recognized that a scratch-pad type memory, utilizing ROM's storing data corresponding to a reference direction for a corresponding path and various amounts of angular offsets from that reference direction, may be used. In that instance, a calculation is made between a determined angular offset of the source data from the reference direction with respect to the traced path. Then, the appropriate ROM is selected and the data read out therefrom and stored in a scratch-pad memory such as a series of registers similar to that shown in FIG. 25 wherein the comparison function is performed in the manner described. Therefore, the particular loop type is identified by comparison with the properly rotated reference path data.

Although the foregoing embodiment of the present invention is directed to the processing of fingerprint patterns, it is recognized that any pattern which may be represented by a unique minutia pattern or a line contour pattern may be processed and identified by the foregoing techniques. Patterns resulting from sound wave analysis, mechanical stress analysis, frequency spectrum anaylsis and contour mapping are among several which are seen as appropriate for processing by the present invention.

It will be apparent that many modifications and variations may be effected without departing from the scope of the novel concept of this invention. The aforesaid embodiment of the subject invention directed to the comparison of fingerprint patterns should not be seen as narrowing the scope and utility for which the invention may be employed. Therefore, it is intended by the appended claims to cover all such modifications and variations which fall within the true spirit and scope of the invention.

What is claimed is:

1. An interactive method for performing a succession of processing functions in relation to an unknown pattern to extract minutiae data therefrom uniquely identifying the pattern for subsequent comparison with minutiae data corresponding extracted from at least one known such pattern to determine a match therebetween, said processing functions being performed selectively in an automatic, continuous succession, and in an interrupted succession with operator interaction requested by the method, as a function of method determination of satisfactory performance of each said processing function, comprising the steps of:

storing said minutiae data of said at least one known such pattern, comparing the extracted and the stored minutiae data to determine a degree of match therebetween, establishing a required degree of match to determine satisfactory performance of said matching function and responsive to the degree of match determined by said comparing step to request operator interaction when said required degree of match is not satisfied, and to identify the given pattern as the known pattern for which the required degree of match is satisfied, selectively displaying the given pattern in response to an operator interaction request and for selectively displaying the automatically extracted minutiae data in superposed relationship thereon, and providing manually operable means for selectively correcting and supplementing the automatically extracted minutiae data to enable said comparing step to automatically compare the selectively corrected and supplemented minutiae data extracted from said given pattern with said stored minutiae data.

2. An interacitve method as recited in claim 1, wherein:

said storing step stores minutiae data corresponding to plural said known patterns, said comparing step compares the automatically extracted minutiae data with the stored minutiae data for each of said stored patterns and produces a corresponding output indicating the degree of match therebetween, and said determining step compares the number of said matches with a predetermined number thereof to determine satisfactory performance of said minutiae data matching function when the number of matches does not exceed said predetermined number, and requests operator interaction when the number of matches exceeds said predetermined number, and said manually operable means provides for selective display of the minutiae data of each of said stored patterns in superposed relationship with the extracted minutiae data of the given said pattern, in succession, to permit operator evaluation of the unsatisfactory matching function.

3. An interactive method for performing a succession of processing functions in relation to an unknown pattern to extract data characterizing said pattern for subsequent comparison with data characterizing at least one of plural pattern types to determine a match therebetween, said processing functions being performed selectively in an automatic, continuous succession, and in an interrupted succession with operator interaction requested by the method, in accordance with method determination of satisfactory performance of successive said processing functions, comprising the steps of:

storing data defining preestablished classification types of said patterns, automatically extracting classification defining data from a given pattern, comparing the extracted and the stored classification defining data to determine a degree of match therebetween, establishing a required degree of match to determine satisfactory performance of said matching function and responsive to the degree of match determined by said comparing steps to identify a preestablished classification type for which the degree of match is satisfied as the classification type of the said given pattern, and to request operator interaction when the said required degree of match is not satisfied, selectively displaying the given pattern in accordance with an operator interaction request, and providing means manually operable by an operator in response to an operator interaction request for extracting classification defining data from the displayed, said given pattern, and enabling said comparing step to perform the function of automatic classification of the pattern by comparing the manually extracted classification defining data for the said given pattern with the stored classification defining data to identify the classification type of the said given pattern.

4. An interactive method as recited in claim 3, wherein:

said selective displaying step further displays the automatically extracted classification defining data in accordance with the operator interaction request, and said manually operable means is selectively operable to correct and to complete the displayed, automatically extracted classification defining data.

5. An interactive method for performing a succession of processing functions in relation to an unknown pattern to extract data characterizing said pattern for subsequent comparison with data characterizing at least one of plural pattern types to determine a match therebetween, said processing functions being performed selectively in an automatic, continous succession, and in an interrupted succession with operator interaction requested by the method, in accordance with method determination of satisfactory performance of successive said processing functions, comprising the steps of:

storing data defining preestablished classification types of said patterns, automatically extracting classification defining data from a given pattern, comparing the extracted and the stored classification defining data to determine a degree of match therebetween, establishing a required degree of match to determine satisfactory performance of said matching function and responsive to the degree of match determined by said comparing steps to identify a preestablished classification type for which the degree of match is satisfied as the classification type of the said given pattern, and to request operator interaction when the the said required degree of match is not satisfied, selectively displaying the given pattern in accordance with an operator interaction request, and providing means manually operable by an operator in response to an operator interaction request for extracting classification defining data from the displayed, said given pattern, and enabling said comparing step to perform the function of automatic classification of the pattern by comparing the manually extracted classification defining data for the said given pattern with the stored classification defining data to identify the classification type of the said given pattern, said selective method selectively displaying the manually extracted classification defining data and, simultaneously and in superposed relationship, the stored classification defining data for a given classification type, and said manually operable means selectively displaying said stored classification defining data corresponding to plural different preestablished classification types to enable manual comparison of the manually extracted classification defining data with the stored data defining the plural preestablished classification types.

6. An interactive method for performing a succession of processing functions in relation to an unknown pattern to extract data characterizing said pattern for subsequent comparison with data characterizing at least one of plural pattern types to determine a match therebetween, said processing functions being performed selectively in an automatic, continuous succession, and in an interrupted succession with operator interaction requested by the method, in accordance with method determination of satisfactory performance of successive said processing functions, comprising the steps of:

storing data preestablished classification types of said patterns, automatically extracting classification defining data from a given pattern, comparing the extracted and the stored classification defining data to determine a degree of match therebetween, establishing a required degree of match to determine satisfactory performance of said matching function and responsive to the degree of match determined by said compring steps to identify a preestabished classification type for which the degree of match is satisfied as the classification type of the said given pattern, and to request operator interaction when the said required degree of match is not satisfied, selectively displaying the given pattern in accordance with an operator interaction request, and providing means manually operable by an operator in response to an operator interaction request for extracting classification defining data from the displayed, said given pattern, and enabling said comparing step to perform the function of automatic classification of the pattern by comparing the manually extracted classification defining data for the said given pattern with the stored classification defining data to identify the classification type of the said given pattern, said classification defining data including triradii points, core points, and contour line and wherein said preestablished classification types include predetermined numbers and combinations of respective ones of aid triradii points an core points and wherein there is further provided the step of responding selectively to the number and combinations of respective ones of said triradii and core points extracted from a given pattern which do not correspond to those of preestablished classification types of patterns to determine an unsatisfactory performance of the classification an thereby to request operator interaction 7. An interactive method as recited in claim 6, wherein:

said selective displaying step displays, in response to an operator interaction request, each of the said triradii points, core points and contour lines automatically extracted from the said given pattern, and said manually operable means provides selectively for correction and supplementation of the said triradii points, core points and contour lines in accordance with manual extraction from the displayed pattern, thereby to enable the comparing step to compare the selectively corrected and supplemented classification defining data extracted from the given pattern with the stored said classification type defining data.

8. An interactive method for identifying an unknown pattern by comparison with stored patterns, each such pattern being characterized uniquely by a minutiae pattern and a configuration of contour lines, wherein an automatic portion of said method comprises the steps of:

scanning an unknown pattern;

automatically extracting minutiae data describing said minutiae pattern from said scanned pattern;

storing said extracted minutiae data;

storing the minutiae data of each of a plurality of previously identified patterns in addressable locations;

selectively addressing and retrieving said stored minutiae date;

automatically comparingsaid extracted minutiae data with retrieved minutiae data corresponding to selected ones of said plurality of patterns in succession and producing a match signal when said compared data machines within predetermined limits;

indicating the identity of said corresponding pattern for each match signal;

generating a first output signal when no match signals are produced; and generating a second output signal when more than a predetermined number of match signals are produced;

said interactive system further comprises the steps of;

providing interactive communication between said automatic portion of said method and a human operator, wherein said step of interactive communication includes the step of requesting operator verification of said automatically extracted minutiae data when said first or second output signals are generated;

selectively displaying said automatically extracted minutiae data, said unknown pattern, said retrieved minutiae data corresponding to said selected ones of said plurality of patterns for which a match signal is produced; and entering correct minutiae data and deleting incorrect extracted minutiae data in storage; and instructing said automatic portion of said method to automatically compare said corrected extracted minutiae data with said retrieved minutiae data corresponding to said selected ones of said plurality of patterns.

9. An interactive method as in claim 8, wherein said steps of extracting minutiae data includes the steps of defining a reference coordinate system and presenting said extracted minutiae data in an X, Y, $\theta$ format, where X and Y indicate coordinate locations of each extracted minutia with respect to said defined coordinate system and $\theta$ indicates the angular orientation of each extracted minutia with respect to said defined coordinate system;

said step of storing said previously identified minutiae data is performed by storing said previously identified data in an X, Y, $\theta$ format;

said step of comparing includes the steps of automatically converting said extracted minutiae data and said retrieved minutiae data into an RIV format, wherein each minutia is represented in terms of its surrounding minutiae in a surrounding neighborhood of a predetermined size; and said steps of comparing includes the steps of matching each minutia of said unknown pattern represented in an RIV format with each minutia of a selected previously identified pattern represented in an RIV format and producing a pluraliy of neighborhood comparison signals indicating the relative closeness of match and relative coordinate displacement between minutia neighborhoods of the compared patterns, and developing output signals indicative of the relative closeness of match and the relative coordinate displacement of the compared patterns.

10. An interactive method as in claim 9, wherein said automatic portion of said method further includes the steps of:

extracting contour data from said scanned pattern corresponding to said configuration of contour lines;

classifying said unknown pattern into one of a predetermined number of classification types defined by reference pattern contour configurations and thereby producing a classification type output signal;

said step of storing said previously identified minutiae data is performed by defining classification bins corresponding to said predetermined number of classification types, said previously, identified minutiae data being stored in corresponding classification bins according to the classification type of each previously identified pattern; and said step of addressibg and retrieving is performed by receiving said classification type output signal and addressing a corresponding classification bin to retrieve stored minutiae data from said addressed classification bin.

11. An interactive method as in claim 10, wherein said step of scanning includes the steps of imaging said unknown pattern and converting said image into a binary bit stream of electrical signals in a line scan format representing said unknown pattern;

said method further includes the step of window scanning said binary bit stream for producing a window scan address;

said step of automatically extracting minutiae data includes the steps of providing preprogrammed means responsive to said window scan address for detecting the occurrence of minutiae in said represented pattern, and providing means responsive to said programmed means for determining the location of said detected minutiae with respect to said defined coordinate system; and said step of storing said extracted minutiae data stores the location coordinate values for each of the extracted minutiae.

12. An interactive system for performing a succession of processing functions in relation to an unknown pattern to extract minutiae data therefrom uniquely identifying the pattern for subsequent comparison with minutiae data corresponding extracted from at least one known such pattern to determine a match therebetween, said processing functions being performed selectively in an automatic, continuous succession, and in an interrupted succession with operator interaction requested by the system, as a function of system determination of satisfactory performance of each said processing function, comprising:

means for storing said minutiae data of said at least one known such pattern, means for comparing the extracted and the stored minutiae data to determine a degree of match therebetween, means establishing a required degree of match to determine satisfactory performance of said matching function and responsive to the degree of match determined by said comparing means to request operator interaction when said required degree of match is not satisfied, and to identify the given pattern as the known pattern for which the required degree of match is satisfied, means for selectively displaying the given pattern in response to an operator interaction request and for selectively displaying the automatically extracted minutiae data in superposed relationship thereon, and manually operable means for selectively correcting and supplementing the automatically extracted minutiae data to enable said comparing means to automatically compare the selectively corrected and supplemented minutiae data extracted from said given pattern with said stored minutiae data.

13. An interactive system as recited in claim 12, wherein:

said storing means stores minutiae data corresponding to plural said known patterns, said comparing means compares the automatically extracted minutiae data with the stored minutiae data for each of said stored patterns and produces a corresponding output indicating the degree of match therebetween, and said determining means compares the number of said matches with a predetermined number thereof to determine satisfactory performance of said minutiae data matching function when the number of matches does not exceed said predetermined number, and requests operator interaction when the number of matches exceeds said predetermined number, and said manually operable means provides for selective display of the minutiae data of each of said stored patterns in superposed relationship with the extracted minutiae data of the given said pattern, in succession, to permit operator evaluation of the unsatisfactory matching function.

14. An interactive system for performing a succession of processing functions in relation to an unknown pattern to extract data characteristizing said pattern for subsequent comparison with data characterizing at least one of plural pattern types to determine a match therebetween, said processing functions being performed selectively in an automatic, continuous succession, and in an interrupted succession with operator interaction requested by the system, in accordance with system determination of satisfactory performance of successive said processing functions, comprising:

means for storing data defining preestablished classification types of said patterns, means for automatically extracting classification defining data from a given pattern, means for comparing the extracted and the stored classification defining data to determine a degree of match therebetween, means establishing a required degree of match to determine satisfactory performance of said matching function and responsive to the degree of match determined by said comparing means to identify a preestablished classification type for which the degree of match is satisfied as the classification type of the said given pattern, and to request operator interaction when the said required degree of match is not satisfied, means for selectively displaying the given pattern in accordance with an operator interaction request, and means manually operable by an operator in response to an operator interaction request for extracting classification defining data from the displayed, said given pattern, said enabling said comparing means to perform the function of automatic classification of the pattern by comparing the manually extracted classification defining data for the said given pattern with the stored classification defining data to identify the classification type of the said given pattern.

15. An interactive system as recited in claim 14, wherein:

said selective display means further displays the automatically extracted classification defining data in accordance with the operator interaction request, and said manually operable means is selectively operable to correct and to complete the displayed, automatically extracted classification defining data.

16. An interactive system for performing a succession of processing functions in relation to an unknown pattern to determine the classification type thereof as one of plural, known classification types, and to identify the unknown pattern as a known, stored pattern of the same, determined classification type, said processing functions being performed selectively in an automatic, continuous succession and in an interrupted succession with operator interaction requested by the system, in accordance with system determination of satisfactory performance or unsatisfactory performance, respectively, of each said processing function, comprising:

means for storing data defining preestablished classification types of said patterns, means for automatically extracting classification defining data from a given pattern, means for comparing the extracted and the stored classification defining data to determine a degree of match therebetween, means establishing a required degree of match to determine satisfactory performance of said matching function and responsive to the degree of match determined by said comparing means to identify a preestablished classification type for which the degree of match is satisfied as the classification type of the said given pattern, and to request operator interaction when the said required degree of match is not satisfied, means for selectively displaying the given pattern in accordance with an operator interaction request, means manually operable by an operator in response to an operator interaction request for extracting classification defining data from the displayed, said given pattern, and enabling said comparing means to perform the function of automatic classification of the pattern by comparing the manually extracted classification defining data for the given pattern with the stored classification defining data to identify the classification type of the said given pattern, means for storing minutiae data of known said patterns of different classification types, means responsive to the identified classification type of the unknown pattern for selecting the stored minutiae data of known said patterns of the said identified classification type from said storing means, means for comparing the extracted minutiae data and the stored minutiae data for each said pattern of the said selected, identified classification type to determine the corresponding degrees of match therebetween, means establishing a required degree of match to determine satisfactory performance of said matching function and responsive to the degree of match determined by said comparing means to request operator interaction when said required degree of match is not satisfied, and to identify the given pattern as the known pattern for which the required degree of match is satisfied, means for selectively displaying the given pattern in response to an operator interaction request and for selectively displaying the automatically extracted minutiae data in superposed relationship thereon, and manually operable means for selectively correcting and supplementing the automatically extracted minutiae data to enable said comparing means to automatically compare the selectively corrected and supplemented minutiae data extracted from said given pattern with said stored minutiae data.

17. An interactive system for performing a succession of processing functions in relation to an unknown pattern to extract data characterizing said pattern for subsequent comparison with data characterizing at least one of plural pattern types to determine a match therebetween, said processing functions being performed selectively in an automatic continuous succession, and in an interrupted succession with operator interaction requested by the system, in accordance with system determination of satisfactory performance of successive said processing functions, comprising:

means for storing data defining preestablished classification types of said patterns, means for automatically extracting classification defining data from a given pattern, means for comparing the extracted and the stored classification defining data to determine a degree of match therebetween, means establishing a required degree of match to determine satisfactory performance of said matching function and responsive to the degree of match determined by said comparing means to identify a preestablished classification type for which the degree of match is satisfied as the classification type of said given pattern, and to request operator interaction when the said required degree of match is not satisfied, means for selectively displaying the given pattern in accordance with an operator interaction request, and means manually operable by an operator in response to an operator interaction request for extracting classification defining data from the displayed, said given pattern, and enabling said comparing means to perform the function of automatic classification of the pattern by comparing the manually extracted classification defining data for the said given pattern with the stored classification defining data to identify the classification type of the said given pattern, said selective displaying means selectively displaying the manually extracted classification defining data and, simultaneously and in superposed relationship, the stored classification defining data for a given classification type, and said manually operable means including means for selectively displaying said stored classification defining data corresponding to plural different preestablished classification types to enable manual comparison of the manually extracted classification defining data with the stored data defining the plural preestablished classification types.

18. An interactive system for performing a succession of processing functions in relation to an unknown pattern to extract data characterizing said pattern for subsequent comparison with data characterizing at least one of plural pattern types to determine a match therebetween, said processing functions being performed selectively in an automatic, continuous succession, and in an interrupted succession with operator interaction requested by the system, in accordance with system determination of satisfactory performance of successive said processing functions, comprising:

means for storing data defining preestablished classification types of said patterns, means for automatically extracting classification defining data from a given pattern, means for comparing the extracted and the stored classification defining data to determine a degree of match therebetween, means establishing a required degree of match to determine satisfactory performance of said matching function and responsive to the degree of match determined by said comparing means to identify a preestablished classification type for which the degree of match is satisfied as the classification type of the said given pattern, and to request operator interaction when the said required degree of match is not satisfied, means for selectively displaying the given pattern in accordance with an operator interaction request, and means manually operable by an operator in response to an operator interaction request for extracting classification defining data from the displayed, said given pattern, and enabling said comparing means to perform the function of automatic classification of the pattern by comparing the manually extracted classification defining data for the said given pattern with the stored classification defining data to identify the classification type of the said given pattern, said classification defining data including triradii points, core points, and contour lines and wherein said preestablished classification types include predetermined numbers and combinations of respective ones of said triradii points and core points, and wherein there is further provided means responsive selectively to the number and combinations of respective ones of said triradii and core points extracted from a given pattern which do not correspond to those of preestablished classification types of patterns to determine an unsatisfactory performance of the classification function and thereby to request operator interaction.

19. An interactive system as recited in claim 18, wherein:

said selective displaying means displays, in response to an operator interaction request, each of the said triradii points, core points and contour lines automatically extracted from the said given pattern, and said manually operable means provides selectively for correction and supplementation of the said triradii points, core points and contour lines in accordance with manual extraction from the displayed pattern, thereby to enable the comparing means to compare the selectively corrected and supplemented classification defining data extracted from the given pattern with the stored said classification type defining data.

20. An operator interactive system for identifying an unknown pattern by comparison with stored patterns, each such pattern being characterized uniquely by a minutiae pattern and a configuration of contour lines, wherein an automatic portion of said system comprises:

means for scanning an unknown pattern;

means for automatically extracting minutiae data describing said minutiae pattern from said scanned pattern;

first means for storing said extracted minutiae data;

second means for storin the minutiae data of each of a plurality of previously identified patterns in addressable locations;

means for selectively addressing and retrieving said minutiae data stored in said second storing means;

means for automatically comparing said extracted minutiae data stored in said first storing means with retrieved minutiae data corresponding to selected ones of said plurality of patterns in succession and producing a match signal when said compared data matches within predetermined limits;

means responsive to said comparing means for indicating the identity of said corresponding pattern for each match signal; and means responsive to said comparing means and said addressing means for generating a first output signal when no match signals are produced and generating a second output signal when more than a predetermined number of match signals are produced;

said system also includes means selectively connected to said scanning means, said first storing means, said second storing means and to said first and second output signal generating means, and interfacing said automatic portion and a human operator for providing interactive communication between said automatic portion and said operator;

said interactive means being responsive to said first and second output signals for requesting operator verification of said automatically extracted minutiae data;

said interactive means including means for displaying images and means manually operable by said operator to command said system to selectively display said automatically extracted minutiae data on said display means, to display said unknown pattern, to display said retrieved minutiae data corresponding to said selected ones of said plurality of patterns for which a match signal is produced by said comparing means, to enter correct minutiae data and delete incorrect minutiae data in said first storing means as determined by said operator, and to instruct said automatic comparison means to compare said corrected extracted minutiae data with said retrieved minutiae data corresponding to said selected ones of said plurality of patterns.

21. A system as in claim 20, wherein said extracting means defines a reference coordinate system and presents said extracted minutiae data in an X, Y, $\theta$ format, wherein X and Y indicate coordinate locations of each detected minutia with respect to said defined coordinate system and $\theta$ indicates the angular orientation of each detected minutia with respect to said defined coordinate system;

said second storing means stores said retrievable minutiae data in an X, Y, $\theta$ format;

said comparing means includes means for automatically converting said minutiae data from said first storing means and said retrieved minutiae data from said second storing means into an RIV format, wherein each minutia is represented in terms of its surrounding minutiae in a surrounding neighborhood of a predetermined size; and said comparing means also includes means for matching each minutia of said unknown pattern represented in an RIV format with each minutia of a selected previously identified pattern represented in an RIV format and producing a plurality of neighborhood comparison signals indicating the relative closeness of match and relative coordinate displacement between minutia neighborhoods of the compared patterns, and means responsive to the neighborhood comparison signals for developing output signals indicative of the relative closeness of match and the relative coordinate displacement of the compared patterns.

22. A system as in claim 21, wherein said automatic portion further comprises;

means for extracting contour data from said scanned pattern corresponding to said configuration of contour lines;

means receiving said extracted contour data for classifying said unknown pattern into one of a predetermined number of classification types defined by reference pattern contour configurations and producing a classification type output signal;

said second storing means defines classification bins corresponding to said predetermined number of classification types, said previously identified minutiae data being stored in corresponding classification bins according to the classification type of each previously identified pattern; and said addressing and retrieving means receives said classification type output signal from said classifying means for addressing said second storing means at a corresponding classification bin and retrieves stored minutiae data from said addressed classification bin.

23. A system as in claim 22, wherein said scanning means includes means for imaging said unknown pattern and means for converting said image into a binary bit stream of electrical signals in a line scan format representing said unknown pattern;

said system further includes means for window scanning said binary bit stream for producing a window scan address;

said automatic minutiae data extracting means includes preprogrammed means responsive to said window scan address for detecting the occurrence of minutiae in said represented pattern, means responsive to said preprogrammed means for determining the location of said detected minutiae with respect to said defined coordinate system, said first storing means stores the location coordinate values for each of the detected minutiae.

24. A system as in claim 23, wherein said scanning means is a television camera and said pattern in a latent fingerprint.

25. A system as in claim 23, wherein said contour data extracting means includes preprogrammed means responsive to said window scan address for reading out corresponding local angle values greater than zero when said window scanning means produces a window scan address corresponding to a contour line of said represented pattern being in said window and for reading out a zero value when said window scanning means produces a scan address which does not correspond to a contour line of said represented pattern being in said window.

26. A system as in claim 25, wherein said contour data extracting means includes means for automatically averaging said local angle values read out from said preprogrammed means over predetermined areas of said represented pattern, means receiving said averaged local angle values for generating a flow angle value for each predetermined area of said represented pattern, means for storing said flow angle values as contour data in addressable locations, and means for addressing said flow angle storing means in accordance with each predetermined area of said represented pattern.

27. A system as in claim 26, wherein said window scanning means includes a first serial-in/parallel-out three bit register connected to receive said binary bit stream, a first serial-in/serial-out full line delay register connected to receive said binary bit stream, a second serial-in/parallel-out three bit register connected to receive the output of said first full line delay register, a second serial-in/serial-out full line delay register connected to receive the output of said first full line delay register, and a third serial-in/parallel-out three bit register connected to receive the output of said second full line delay register, wherein said first, second and third three bit registers form a three by three bit scanning window which advances one bit by one bit over said binary bit stream in said line scan format and provides said window scan address nine bits in length.

28. A system as in claim 25, wherein said classifying means includes means for window scanning said contour data by sequentially sampling each stored local angle value and a predetermined number of its surrounding local angle values;
means responsive to said sampled contour data for determining the occurrence and location of any singularity point in said represented pattern;
means responsive to said singularity point location means for producing a third output signal when more than a predetermined number of singularity points are located;
said interactive means being responsive to said third output signal for requesting operator correction of said located singularity points;
said manually operable means further provides for said operator to command said system to display said singularity points at said determined locations and to enter the correct location of singularity points as determined by said operator.

29. A system as in claim 28, wherein
said classifying means includes means responsive to said singularity point determining means for producing curve tracings corresponding to those of said contour lines extending from each located singularity point;
means for storing reference curve tracings corresponding to a plurality of said reference pattern contour configurations;
means for comparing said produced curve tracings with each of said stored reference curve tracings and producing a corresponding comparison value signal for each comparison.

30. A system as in claim 29, wherein said classifying means further includes means responsive to said comparison value signals for determining said classification type when a comparison value signal is within a predetermined value and producing a corresponding classification type output signal, said classification type detecting means produces a fourth output signal when no comparison value signals are within said predetermined value;
said interactive means being responsive to said fourth output signal for requesting operator verification of said produced curve tracings.

31. A system as in claim 30, wherein said contour data window scanning means includes a 7 by 7 byte buffer having a center cell for sequentially sampling each said stored flow angle value and 48 cells surrounding said center cell, corresponding to said predetermined number, for sampling said predetermined number of surrounding angle values;
said singularity point determining means includes means for correlating the average angle values sampled by said surrounding cells for each angle value sampled by said center cell with respect to a predetermined number of reference angles defined as extending from said center cell and producing a correlation value for each of said predetermined number of reference values at each angle value sampled by said center cell,
means receiving said correlation values for determining peaks in said correlation values, the number of said correlation value peaks and identifying each peak correlation value by its corresponding reference angle value,
means for storing said number of correlation value peaks for each angle value sampled by said center cell in locations corresponding to said predetermined areas of said represented pattern, and
means for storing said reference angle values identified as corresponding to each of said correlation value peaks in locations corresponding to said predetermined areas of said represented pattern.

32. A system as in claim 31, wherein said singularity point determining means further includes means for sequentially scanning said numbers stored in said number of peaks storing means and means responsive to said number of peaks scanning means for eliminating all numbers in said number of peaks storing means which are not equal to 1 or 3 and allowing said numbers equal to 1 or 3 to remain.

33. A system as in claim 32, wherein said system includes means for automatically distinguishing said scanned pattern from its background, determining those of said predetermined areas in which said background occurs in said scanned pattern and producing corresponding background cancelling signals; and means for gating said background cancelling signals to said number of peaks storing means and eliminating all numbers therein which are stored in locations corresponding to said areas of determined background.

34. A system as in claim 33, wherein said singularity point determining means further includes means for simultaneously scan sampling each cell location and two predetermined adjacent cell locations of said number of peaks storing means, means responsive to said scan sampling means at each sampled cell location for comparing sampled values at each sampled cell location and its corresponding two adjacent cell locations and producing cancellation signals each time said sampled value from each said sampled cell location is different from either of said sampled values from its corresponding two adjacent cell locations; and means for applying said cancellation signals to said number of peaks storing means to eliminate numbers stored in each cell location therein which differs in value from either of its corresponding two predetermined adjacent cell locations to reduce the size of clusters of numbers of equal value and eliminate spurious numbers stored in said number of peaks storing means.

35. A system as in claim 34, wherein said singularity point determining means further includes means responsive to said cancellation signal applying means for single cell sample scanning said number of peaks storing means;

means responsive to said single cell sampling means for producing a singularity point location signal when said number sampled thereby has a value of 1 or 3, wherein said location signal has a value corresponding to the address location of the corresponding cell location in said number of peaks storing means incremented by a +1 value in both row and column portions thereof;

means for storing said singularity point location signal; and means for incrementing said address to said number of peaks storing means for said single cell sample scanning means by +3 in both the row and column portions thereof.

* * * * *

UNITED STATES PATENT AND TRADEMARK OFFICE
CERTIFICATE OF CORRECTION

PATENT NO. : 4,047,154
DATED : September 6, 1977
INVENTOR(S) : V.A. Vitols et al It is certified that error appears in the above-identified patent and that said Letters Patent are hereby corrected as shown below:

Col. 36, line 24 after "data" insert ---defining---.

Col. 36, line 55 delete [aid] and insert ---said---.

Col. 36, line 55 delete [an] and insert ---and---.

Col. 36, line 62 after "classification" insert ---function---; delete /an/ and insert ---and---.

Col. 37, line 27 delete [comparingsaid] and insert ---comparing said---.

Col. 37, line 31 delete [machines] and insert ---matches---.

Col. 37, line 64 delete [where] and insert ---wherein---.

Col. 38, line 57 delete [programmed] and insert ---preprogrammed---.

Col. 41, line 61 after "of" insert ---the---.

Col. 43, line 31 delete [storin] and insert ---storing---.

Col. 45, line 11 delete [in] and insert ---is---.

Signed and Sealed this

Sixth Day of June 1978

[SEAL]

Attest:

RUTH C. MASON
Attesting Officer

DONALD W. BANNER
Commissioner of Patents and Trademarks